(12) United States Patent
Ghoroghchian et al.

(10) Patent No.: US 8,808,748 B2
(45) Date of Patent: Aug. 19, 2014

(54) BIODEGRADABLE NANOPARTICLES AS NOVEL HEMOGLOBIN-BASED OXYGEN CARRIERS AND METHODS OF USING THE SAME

(75) Inventors: P. Peter Ghoroghchian, Philadelphia, PA (US); Eric Ostertag, Lexington, KY (US)

(73) Assignee: Vindico Nanobio Technology Inc., Lexington, KY (US)

( * ) Notice: Subject to any disclaimer, the term of this patent is extended or adjusted under 35 U.S.C. 154(b) by 288 days.

(21) Appl. No.: 13/090,076

(22) Filed: Apr. 19, 2011

(65) Prior Publication Data
US 2011/0256225 A1 Oct. 20, 2011

Related U.S. Application Data

(60) Provisional application No. 61/326,222, filed on Apr. 20, 2010, provisional application No. 61/430,628, filed on Jan. 7, 2011.

(51) Int. Cl.
*A61K 9/14* (2006.01)
*A61K 38/00* (2006.01)

(52) U.S. Cl.
USPC .............................. 424/489; 514/2; 977/915

(58) Field of Classification Search
None
See application file for complete search history.

(56) References Cited

U.S. PATENT DOCUMENTS 7,417,118 B2 * 8/2008 Kai et al. ...................... 530/350
7,998,458 B2 * 8/2011 Sung et al. ................... 424/1.69

OTHER PUBLICATIONS

Rameez et al.,"Biocompatible and Biodegradable Polymersome Encapsulated Hemoglobin: A Potential Oxygen Carrier", Bioconjugate Chem. 19: 1025-1032 (2008).*
Zhao et al., "Preparation of hemoglobin-loaded nano-sized particles with porous structure as oxygen carrier", Biomaterials 28: 1414-1422 (2007).*
International Search Report & Written Opinion issued in PCT Application No. PCT/US2011/033190, mailed on Jan. 18, 2012.
Zhao, Jian, et al. "Preparation of hemoglobin-loaded nano-sized particles with porous structure as oxygen carriers": Biomaterials 28 (2007); pp. 1414-1422.
Xu, Fang, et al. "Long-circulation of hemoglobin-loaded polymeric nanoparticles as oxygen carriers with modulated surface charges"; International Journal of Pharmaceuticals 377 (2009); pp. 199-206.
Piras, Anna Maria, et al. "Polymeric nanoparticles for hemoglobin-based oxygen carriers"; Biochimica et Biophysica Acta 1784 (2008); pp. 1454-1461.
Chang, Thomas Ming Swi; "Blood substitutes based on nanobiotechnology"; Trends in Biotechnology, vol. 24, No. 8 (2006); pp. 372-377.

"Cancer Facts & Figures 2010" by American Cancer Society © 2010.
Feldmann, Horst J., et al. "Blood Flow and Oxygenation Status of Human Tumors"; Strahlenther Onkol © 1999; vol. 175, No. 1, pp. 1-9.
Harrison, Louis B., et al. "Hypoxia and Anemia: Factors in Decreased Sensitivity to Radiation Therapy and Chemotherapy?"; The Oncologist © 2004; vol. 9, pp. 31-40.
Harrison, Louis B., et al. "Impact of Tumor Hypoxia and Anemia on Radiation Therapy Outcomes"; The Oncologist © 2002; vol. 7, pp. 492-508.
Mundt, Arno J., et al. "Race and Clinical Outcome in Patients with Carcinoma of the Uterine Cervix Treated with Radiation Therapy"; Gynecologic Oncology © 1998; vol. 71, pp. 151-158, Article No. GO985203.
Takeshi, Kodaira, et al. "Definitive Radiotherapy Combined with High-Dose-Rate Brachytherapy for Stage III Carcinoma of the Uterine Cervix: Retrospective Analysis of Prognostic Factors Concerning Patient Characteristics and Treatment Parameters"; Int. J. Radiation Oncology Biol. Phys. © 1998; vol. 41, No. 2, pp. 319-327.
Rockwell, Sara, et al. "Hypoxia and Radiation Therapy: Past History, Ongoing Research, and Future Promise"; Curr Mol Med. © May 2009; vol. 9, No. 4, pp. 442-458.
Carlson, D.J., et al. "Towards Temporal Optimization of Radiation Fractionation: The Kinetic Effects of Tumor Hypoxia, DNA Damage Repair, and Tumor Cell Repopulation"; Proceedings of the 51st Annual ASTRO Meeting © 2009; No. 2968.
Brown, J. Martin "The Hypoxic Cell: A Target for Selective Cancer Therapy"; Cancer Research © 1999; vol. 59, pp. 5863-5870; //cancerres.aacrjournals.org/content/59/23/5863.
Dietz, Andreas, et al. "Rise of Oxygenation in Cervical Lymph Node Metastasis During the Initial Course of Radiochemotherapy"; Otolaryngology—Head and Neck Surgery © 1999, vol. 121, pp. 789-796.
Evans, S.M., et al. "Evaluation of the Concept of "Hypoxic Fraction" as a Descriptor of Tumor Oxygenation Status"; Oxygen Transport to Tissue XVIII © 1997, pp. 215-225.
Teicher, Beverly A. "Physiologic Mechanisms of Therapeutic Resistance—Blood Flow and Hypoxia"; Drug Resistance in Clinical Oncology and Hematology © Apr. 1995, vol. 9, No. 2, pp. 475-506.
Kaelin, Jr., William G. "ROS: Really Involved in Oxygen Sensing"; Cell Metabolism © Jun. 2005, pp. 357-358.

(Continued)

*Primary Examiner* — Anand Desai
(74) *Attorney, Agent, or Firm* — The Marbury Law Group, PLLC

(57) ABSTRACT

Compositions of matter and methods for making, storing and administering artificial blood substitutes. Artificial blood substitutes may have oxygen carriers that encapsulate an oxygen-binding compound in a polymer vesicle. Oxygen-binding compounds may include hemoglobin, myoglobin, or other oxygen binding compounds having characteristics similar to hemoglobin. Oxygen carriers may include nanoparticles, polymers and/or polymersomes comprising of poly (ethylene oxide)-block-poly(ε-caprolactone) (PEO-b-PCL) and related diblock copolymers of poly(ethylene oxide)-block-poly(γ-methyl ε-caprolactone) (PEO-b-PMCL). The oxygen carriers may have tunable oxygen-binding capacities, uniform and appropriately small size distributions, and human bloodlike viscosities and oncotic properties.

30 Claims, 6 Drawing Sheets

(56) References Cited

OTHER PUBLICATIONS

Alarcon, Rodolfo, et al. "Hypoxia Induces p53 Accumulation through MDM2 Down-Regulation and Inhibition of E-6-mediated Degradation"; Cancer Research © 1999; vol. 59, pp. 6046-6054; //cancerres.aacrjournals.org/content/59/24/6046.

Graeber, Thomas G., et al. "Hypoxia-mediated Selection of Cells with Diminished Apoptotic Potential in Solid Tumours"; Nature © Jan. 1996; vol. 379, pp. 88-91.

Brizel, David M., et al. "Oxygenation of Head and Neck Cancer: Changes During Radiotherapy and Impact on Treatment Outcome"; Radiotherapy and Oncology © 1999; vol. 53, pp. 113-117.

Brizel, David M., et al. "Tumor Hypoxia Adversely Affects the Prognosis of Carcinoma of the Head and Neck"; Int. J. Radiation Oncology Biol. Phys. © 1997; vol. 38, No. 2, pp. 285-289.

Fyles, Anthony W., et al. "Oxygenation Predicts Radiation Response and Survival in Patients with Cervix Cancer"; Radiotherapy and Oncology © 1998; vol. 48, pp. 149-156.

Hockel, Michael, et al. "Intratumoral pO2 Predicts Survival in Advanced Cancer of the Uterine Cervix"; Radiotherapy and Oncology © 1993; vol. 26, pp. 45-50.

Hockel, Michael, et al. "Association Between Tumor Hypoxia and Malignant Progression in Advanced Cancer of the Uterine Cervix"; Cancer Research © 1996; vol. 56, pp. 4509-4515; //cancerres.aacrjournals.org/content/56/19/4509.

Hockel, Michael, et al. "Tumor Oxygenation: A New Predictive Parameter in Locally Advanced Cancer of the Uterine Cervix"; Gynecologic Oncology © 1993; vol. 51, pp. 141-149.

Knocke, Tomas-Hendrik, et al. "Intratumoral pO2-Measurements as Predictive Assay in the Treatment of Carcinoma of the Uterine Cervix"; Radiotherapy and Oncology © 1999; vol. 53, pp. 99-104.

Rofstad, E.K., et al. "Hypoxia-induced Treatment Failure in Advanced Squamous Cell Carcinoma of the Uterine Cervix is Primarily Due to Hypoxia-induced Radiation Resistance Rather than Hypoxia-induced Metastasis"; British Journal of Cancer © 2000; vol. 83, No. 3, pp. 354-359.

Rudat, Volker, et al. "Repeatability and Prognostic Impact of the Pretreatment pO2 Histography in Patients with Advanced Head and Neck Cancer"; Radiotherapy and Oncology © 2000; vol. 57, pp. 31-37.

Stadler, Peter, et al. "Influence of the Hypoxic Subvolume on the Survival of Patients with Head and Neck Cancer"; Int. J. Radiation Oncology Biol. Phys. © 1999; vol. 44, No. 4, pp. 749-754.

Karar, Jayashree, et al. "Modulating the Tumor Microenvironment to Increase Radiation Responsiveness"; Cancer Biology & Therapy © Nov. 2009; vol. 8, Issue 21, pp. 1994-2001.

Bache, M. et al. "Detection and Specific Targeting of Hypoxic Regions within Solid Tumors: Current Preclinical and Clinical Strategies"; Current Medicinal Chemistry © 2008; vol. 15, pp. 322-338.

Stadler, Peter, et al. "Changes in Tumor Oxygenation During Combined Treatment with Split-Course Radiotherapy and Chemotherapy in Patients with Head and Neck Cancer"; Radiotherapy and Oncology © 1998; vol. 48, pp. 157-164.

Ahn, G-One, et al. "Targeting Tumors with Hypoxia-activated Cytotoxins"; Frontiers in Bioscience © May 2007; vol. 12, pp. 3483-3501.

Nagasawa, Hideko, et al. "Design of Hypoxia-Targeting Drugs as New Cancer Chemotherapeutics"; Biol. Pharm. Bulletin © 2006; vol. 29, No. 12, pp. 2335-2342.

Ferris, Robert L. "Hypoxia in Head and Neck Cancer: How Much, How Important?"; Head & Neck © Jul. 2005; pp. 622-638.

Wouters, B.G., et al. "Hypoxia as a Target for Combined Modality Treatments"; European Journal of Cancer © 2002; vol. 38, pp. 240-257.

Kondo, Akira, et al. "Hypoxia-induced Enrichment and Mutagenesis of Cells that Have Lost DNA Mismatch Repair"; Cancer Research © 2001; vol. 61, pp. 7603-7607; httpp://cancerres.aacrjournals.org/content/61/20/7603.

Grigsby, Perry W., et al. "Irridation With or Without Misonizadole for Patients with Stages IIIB and IVA Carcinoma of the Cervix: Final Results of RTOG 80-05"; Int. J. Radiation Oncology Biol. Phys. © 1999; vol. 44, No. 3, pp. 513-517.

Lee, Ding-Jen, et al. "Results of an RTOG Phase III Trial (RTOG 85-27) Comparing Radiotherapy Plus Etanidazole with Radiotherapy Alone for Locally Advanced Head and Neck Carcinomas"; Int. J. Radiation Oncology Biol. Phys. © 1995; vol. 32, No. 3, pp. 567-576.

Lee, Ding-Jen, et al. A Phase I/II Study of the Hypoxic Cell Sensitizer Misonidazole as an Adjunct to High Fractional Dose Radiotherapy in Patients with Unresectable Squamous Cell Carcinoma of the Head and Neck; A RTOG Randomized Study (#79-04).

Overgaard, Jens "Sensitization of Hypoxic Tumour Cells—Clinical Experience"; Int. J. Radiation Oncology Biol. Phys. © 1989; vol. 56, No. 5, pp. 801-811.

Overgaard, Jens, et al. "Misonidazole Combined with Radiotherapy in the Treatment of Carcinoma of the Uterine Cervix"; Int. J. Radiation Oncology Biol. Phys. © 1989; vol. 16, pp. 1069-1072.

Overgaard, Jens, et al. "Misonidazole Combined with Split-Course Radiotherapy in the Treatment of Invasive Carcinoma of Larynx and Pharynx: Report from the Dahanca 2 Study"; Int. J. Radiation Oncology Biol. Phys. © 1989; vol. 16, pp. 1065-1068.

Wasserman, Todd H., et al. "Clinical Trials with Etanidazole (SR-2508) by the Radiation Therapy Oncology Group (RTOG)"; Radiotherapy and Oncology © 1991; vol. 20, pp. 129-135.

Fenton, B.M., et al. "Enhancement of Tumor Perfusion and Oxygenation by Carbogen and Nicotinamide during Single- and Multifraction Irradiation"; Radiation Research © Jan. 2000; vol. 153, No. 1, pp. 75-83.

Eisbruch, Avraham, et al. "Bromodeoxyuridine Alternating with Radiation for Advanced Uterine Cervix Cancer: A Phase I and Drug Incorporation Study"; Journal of Clinical Oncology © 1999; vol. 17, No. 1, pp. 31-40.

Rischin, Danny, et al. "Tirapazamine, Cisplatin, and Radiation Versus Cisplatin and Radiation for Advanced Suamous Cell Carcinoma of the Head and Neck (TROG 02.02, HeadSTART): A Phase III Trial of the Trans-Tasman Radiation Oncology Group"; Journal of Clinical Oncology © Jun. 2010; vol. 28, No. 18, pp. 2989-2995.

Fogh, Shannon, et al. "Phase I Trial Using Patupil (Epothilone B) and Concurrent Radiotherapy for Central Nervous System Malignancies"; Int. J. Radiation Oncology Biol. Phys. © 2010; vol. 77, No. 4, pp. 1009-1016.

De La Fouchardiere, Christelle, et al. "Phase I Study of Daily Irinotecan as a Radiation Sensitizer for Locally Advanced Pancreatic Cancer"; Int. J. Radiation Oncology Biol. Phys. © 2010; vol. 77, No. 2, pp. 409-413.

Williams, Kaye J. "In Vivo Activation of the Hypoxia-targeted Cytotoxin AQ4N in Human Tumor Xenografts"; Mol Cancer Ther © 2009; vol. 8, pp. 3266-3275.

Hay, Michael P. "DNA-Targeted 1, 2, 4-Benzotriazine 1,4-Dioxides: Potent Analogues of the Hypoxia-Selective Cytotoxin Tirapazamine"; J. Med. Chem. © 2004; vol. 47, pp. 475-488.

Shibamoto, Yuta, et al. "In Vivo Evaluation of a Novel Antitumor Prodrug, 1-(2'-Oxopropyl)-5-Fluorouracil (OFU001), Which Releases 5-Fluorouracil Upon Hypoxic Irradiation"; Int. J. Radiation Oncology Biol. Phys. © 2001; vol. 49, No. 2, pp. 407-413.

Koch, C.J., et al. "Pharmacokinetics of EF5 [2-(2-nitro1-H-imidazol-1-yl)-N-(2,2,3,3,3-pentafluoropropyl) acetamide] in Human Patients: Implications for Hypoxia Measurements In Vivo by 2-nitroimidazoles"; Cancer Chemother Pharmacol © 2001; vol. 48, pp. 177-187.

Roberts, Kenneth B., et al. "Interim Results of a Randomized Trial of Mitomycin C as an Adjunct to Radical Radiotherapy in the Treatment of Locally Advanced Squamous-Cell Carcinoma of the Cervix"; Int. J. Cancer (Radiat. Oncol. Invest) © 2000; vol. 90, pp. 206-223.

Papadopoulou, Maria V., et al. "4-[3-(2-Nitro-1-Imidazolyl)propylamino]-7-chloroquinoline Hydrochloride (NLCQ-1), a Novel Bioreductive Compound as a Hypoxia-Selective Cytotoxin"; Oncology Research © 2000; vol. 12, pp. 185-192.

Papadopoulou, Maria V., et al. "4-[3-(2-Nitro-1-Imidazolyl)propylamino]-7-chloroquinoline Hydrochloride (NLCQ-1), a Novel Bioreductive Agent as Radiosensitizer In Vitro and In Vivo: Comparison with Tirapazamine"; Oncology Research © 2000; vol. 12, pp. 325-333.

(56) References Cited

OTHER PUBLICATIONS

Craighead, Peter S., et al. "A Phase I/II Evaluation of Tirapazamine Administered Intravenously Concurrent with Cisplatin and Radiotherapy in Women with Locally Advanced Cervical Cancer"; Int. J. Radiation Oncology Biol. Phys. © 2000; vol. 48, No. 3, pp. 791-795.
Weitman, Steven, et al. "Evidence of Enhanced In Vivo Activity Using Tirapazamine with Paclitaxel and Paraplatin Regimens Against the MV-522 Human Lung Cancer Xenograft"; Cancer Chemother Pharmacol © 1999; vol. 43, pp. 402-408.
Treat, Joseph, et al. "Tirapazamine with Cisplatin in Patients with Advanced Non-Small-Cell Lung Cancer: A Phase II Study"; Journal of Clinical Oncology © 1998; vol. 16, No. 11, pp. 3524-3527.
Siemann, Dietmar W., et al. "Potentiation of Cisplatin Activity by the Bioreductive Agent Tirapazmine", Radiotherapy and Oncology © 1998; vol. 47, pp. 215-220.
Lee, Ding-Jen, et al. "Concurrent Tirapazamine and Radiotherapy for Advanced Head and Neck Carcinomas: A Phase II Study"; Int. J. Radiation Oncology Biol. Phys. © 1998, vol. 42, No. 4, pp. 811-815.
Harrison, Louis B., et al. "A Prospective Phase II Trial of Concomitant Chemotherapy and Radiotherapy with Delayed Accelerated Fractionation in Unresectable Tumors of the Head and Neck"; Head & Neck © Sep. 1998; pp. 497-503.
Gatzemeier, U., et al. "Tirapazamine-Cisplatin: The Synergy"; British Journal of Cancer © 1998; vol. 77; No. 4, pp. 15-17.
Brown, J. Martin, et al. "Tirapazamine: Laboratory Data Relevant to Clinical Activity"; Anti-Cancer Drug Design © 1998; vol. 13, pp. 529-539.
Haffty, Bruce G., et al. "Chemotherapy as an Adjunct to Radiation in the Treatment of Squamous Cell Carcinoma of the Head and Neck: Results of the Yale Mitomycin Randomized Trials"; Journal of Clinical Oncology © Jan. 1997; vol. 15, No. 1, pp. 268-276.
Adelstein, David J. "A Phase III Randomized Trial Comparing Concurrent Chemotherapy and Radiotherapy with Radiotherapy Alone in Resectable Stage III and IVE Squamous Cell Head and Neck Cancer: Preliminary Results"; Head & Neck © Oct. 1997; pp. 567-575.
Sartorelli, Alan C., et al. "Mitomycin C: A Prototype Bioreductive Agent"; Oncology Research © 1994; vol. 6, Nos. 10/11, pp. 501-508.
Dobrowsky, W. "Mitomycin C, 5-Fluorouracil and Radiation in Advanced, Locally Recurrent Rectal Cancer"; The British Journal of Radiology © 1992; vol. 65, pp. 143-147.
Sivanesaratnam, V., et al. "Mitomycin C Adjuvant Chemotherapy After Wertheim's Hysterectomy for Stage IB Cervical Cancer"; Cancer © 1989; vol. 64, pp. 798-800.
Keyes, Susan R., et al. "Enhancement of Mitomycin C Cytotoxicity to Hypoxic Tumor Cells by Dicoumarol In Vivo and In Vitro"; Cancer Research © 1985; vol. 45, pp. 213-216; //cancerres.aacrjournals.org/content/45/1/213#related-urls.
Keyes, Susan R., et al. "Porfiromycin as a Bioreductive Alkylating Agent with Selective Toxicity to Hypoxic EMT6 Tumor Cells In Vivo and In Vitro"; Cancer Research © 1985; vol. 45, pp. 3642-3645; ://cancerres.aacrjournals.org/content/45/8/3642.
Overgaard, Jens, et al. "Modification of Hypoxia-Induced Radioresistance in Tumors by the Use of Oxygen and Sensitizers"; Seminars in Radiation Oncology © Jan. 1996; vol. 6, No. 1, pp. 10-21.
Aquino-Parsons, C., et al. "Carbogen Inhalation in Cervical Cancer: Assessment of Oxygenation Change"; Gynecologic Oncology © 1999; vol. 74, pp. 259-264.
Bernier, Jacques, et al. "ARCON: accelerated radiotherapy with carbogen and nicotinamide in head and neck squamous cell carcinomas. The experience of the Co-operative Group of Radiotherapy of the European Organization for Research and Treatment of Cancer (EORTC)"; Radiotherapy and Oncology © 2000; vol. 55, pp. 111-119.
Bussink, Johan, et al. "Clinical Outcome and Tumour Microenvironmental Effects of Accelerated Radiotherapy with Carbogen and Nicotinamide"; ACTA Oncologica © 1999; vol. 38, No. 7, pp. 875-882.

Hoskin, Peter J., et al. "Hypoxic Radiosensitizers in Radical Radiotherapy for Patients with Bladder Carcinoma"; American Cancer Society © 1999; pp. 1322-1328.
Miralbell, Raymond, et al. "Accelerated Radiotherapy, Carbogen, and Nicotinamide in Glioblastoma Multiforme: Report of European Organization for Research and Treatment of Cancer Trial 22933"; J Clin Oncol. © Oct. 1999; vol. 17, No. 10, pp. 3143-3149.
Saunders, M., et al. "Clinical Results of Hypoxic Cell Radiosensitisation from Hyperbaric Oxygen to Accelerated Radiotherapy, Carbogen and Nicotinamide"; Br J Cancer Suppl. © Jul. 1996; vol. 27, pp. S271-S278.
Stuben, Georg, et al. "The Effect of Combined Nicotinamide and Carbogen Treatments in Human Tumour Xenografts: Oxygenation and Tumour Control Studies"; Radiotherapy and Oncology © 1998; vol. 48, pp. 143-148.
Zhan, Hong Wei, et al. "Effect of Carbogen on Tumour Oxygenation and 32P-Colloid Interstitial Irradiation Response"; Med Sci Monit © 2010; vol. 16, No. 1, pp. BR11-BR16.
Yu, Minghua, et al. "Oxygen Carriers and Cancer Chemo- and Radiotherapy Sensitization: Bench to Bedside and Back"; Cancer Treatment Reviews © 2007; vol. 33, pp. 757-761.
Hoogsteen, I.J. "The Hypoxic Tumour Microenvironment, Patient Selection and Hypoxia-modifying Treatments"; Clinical Oncology © 2007; vol. 19, pp. 385-396.
Shasha, Daniel "The Negative Impact of Anemia on Radiotherapy and Chemoradiation Outcomes"; Seminars in Hematology © Jul. 2001; vol. 38, No. 3, pp. 8-15.
Shasha, Daniel, et al. "Once-Weekly Dosing of Epoetin-α Increases Hemoglobin and Improves Quality of Life in Anemic Cancer Patients Receiving Radiation Therapy Either Concomitantly or Sequentially with Chemotherapy"; American Cancer Society—Cancer © 2003; vol. 98, Issue 5, pp. 1072-1079.
Henke, Michael, et al. "Erythropoietin for Patients Undergoing Radiotherapy: A Pilot Study"; Radiotherapy and Oncology © 1999; vol. 50, pp. 185-190.
McGee, Mackenzie C., et al. "Improved Intratumoral Oxygenation through Vascular Normalization Increases Glioma Sensitivity to Ionizing Radiation"; Int J Radiation Oncology Biol Phys. © Apr. 2010; vol. 76, No. 5, pp. 1537-1545.
Katz, David, et al. "On the Path to Seeking Novel Radiosensitizers"; Int J Radiation Oncology Biol Phys. © 2009; vol. 73, No. 4, pp. 988-996.
Gali-Muhtasib, Hala, et al. "Quinoxaline 1,4-dioxides are Novel Angiogenesis Inhibitors that Potentiate Antitumor Effects of Ionizing Radiation". International Journal of Oncology © 2004; vol. 24, No. 5, pp. 1121-1131.
Ordway, George A., et al. "Myoglobin: An Essential Hemoprotein in Striated Muscle"; The Journal of Experimental Biology © 2004; vol. 207, pp. 3441-3446.
Wittenberg, Jonathan B. "Myoglobin Function Reassessed"; The Journal of Experimental Biology © 2003; vol. 206, pp. 2011-2020.
Kooyman, G. L., et al. "The Physiological Basis of Diving to Depth: Birds and Mammals"; Annual Review of Physiology © Mar. 1998; vol. 60, pp. 19-32.
Hochachka, P.W. "The Metabolic Implications of Intracellular Circulation"; PNAS; Oct. 26, 1999; vol. 96, No. 22, pp. 12233-12239.
Conley, Kevin E., et al. "Myoglobin Content and Oxygen Diffusion: Model Analysis of Horse and Steer Muscle"; The American Physiological Society © 1996; pp. C2027-C2036.
Galluzzo, Maria, et al. "Prevention of Hypoxia by Myoglobin Expression in Human Tumor Cells Promotes Differentiation and Inhibits Metastasis"; The Journal of Clinical Investigation © Apr. 2009; vol. 119, No. 4, pp. 865-866.
Dusenbery, Kathryn E., et al. "Erythropoietin increases hemoglobin during radiation therapy for cervical cancer"; Int J Radiat Oncol Biol Phys. © Jul. 1994; vol. 30, No. 29, pp. 1079-1084.
Lavey, Robert S., et al. "Erythropoietin increases hemoglobin in cancer patients during radiation therapy"; International Journal of Radiation Oncology * Biology * Physics © Dec. 1993; vol. 27, Issue 5, pp. 1147-1152.
Overgaard, Jens., et al. "A randomized double-blind phase III study of nimorazole as a hypoxic radiosensitizer of primary radiotherapy in supraglottic larynx and pharynx carcinoma. Results of the Danish

(56) References Cited

OTHER PUBLICATIONS

Head and Neck Cancer Study (DAHANCA) Protocol 5-85"; Radiotherapy & Oncology (1998); vol. 46, Issue: 2, pp. 135-146.

Lim, Sun Ha, et al. "Effect of Combination of Anticancer Agents and Nitroimidazoles on the Survival of Human Hepatocellular Carcinoma Cells under Hypoxic Conditions"; J Korean Surg Soc © 2009; vol. 76, pp. 337-347.

Rosenthal, David I., "A Phase I Single-Dose Trial of Gadolinium Texaphyrin (Gd-Tex), a Tumor Selective Radiation Sensitizer Detectable by Magnetic Resonance Imaging"; Clinical Cancer Research © 1999; vol. 5, pp. 739-745.

Von Pawel, Joachim, et al. "Tirapazamine Plus Cisplatin Versus Cisplatin in Advanced Non-Small-Cell Lung Cancer: A Report of the International CATAPULT I Study Group"; Journal of Clinical Oncology © 2000; vol. 18, No. 6, pp. 1351-1359.

Flogel, Ulrich, et al., Myoglobin Tames Tumor Growth and Spread; J. Clinical Investigation; vol. 119; No. 4; Apr. 209; pp. 766-768.

Bunn, H. F., "The Role of Hemoglobin Based Blood Substitutes in Transfusion Medicine"; Hemoglobin Based Blood Substitutes; 1995; pp. 433-439.

Gottschalk, Andre, et al., "Influence of the Hemoglobin Solution HBOC-201 on Tissue Oxygenation in the Rat R1H-Tumor"; Artificial Cells, Blood Substitutes, and Biotechnology; vol. 33; 2005; pp. 379-389.

Gundersen, Sharon I., et al., "Hemoglobin-Based Oxygen Carrier Enhanced Tumor Oxygenation: A Novel Strategy for Cancer Theraphy"; Biotechnol. Prog; vol. 24; 2008; pp. 1353-1364.

Palaparthy, Rameshraja, et al., "Current Aspects in Pharmacology of Modified Hemoglobins"; Adv. Drug. Delivery Reviews; vol. 40; 2000; pp. 185-198.

Rowinsky, Eric K., "Novel Radiation Sensitizers Targeting Tissue Hypoxia"; Oncology; Supp. No. 5; Oct. 1999; pp. 61-70.

Teicher, Beverly A., et al., "Effect of a Bovine Hemoglobin Preparation on the Response of the FSaIIC Fibrosarcoma to Chemotherapeutic Alkylating Agents"; J. Cancer Res. Clin. Oncol.; vol. 118; 1992; pp. 123-128.

Teicher, Beverly A., et al., "Effect of Hemoglobin Solution on the Response of Intercranial and Subcutaneous 9L Tumors to Antitumor Alkylating Agents;" Cancer Chemother Pharmacol; vol. 33; 1993; pp. 57-62.

Teicher, Beverly A., et al., "Oxygenation of Tumors by a Hemoglobin Solution"; J. Cancer Res. Clin. Oncol; vol. 120; 1993; pp. 85-90.

Christian, David A., et al., "Polymersome Carriers: From Self-Assembly to siRNA and Protein Therapeutics"; European J. of Pharmaceutics and Biopharmceutics; vol. 71; 2009; pp. 463-474.

Levine, Dalia Hope., et al., "Polymersomes: A New Multi-Functional Tool for Cancer Diagnosis and Therapy;" Methods; vol. 46; 2008; pp. 25-32.

Letchford, Kevin, et al., "A Review of the Formation and Classification of Amphiphilic Block Copolymer Nanoparticulate Structures: Micelles, Nanospheres, Nanocapsules and Polymersomes"; European J. of Pharmaceutics and Biopharmaceutics; vol. 65; 2007. pp. 259-269.

Discher, Bohdana M., et al., "Polymer Vesicles in Various Media"; Current Opinion in Colloid & Interface Science; vol. 5; 2000; pp. 125-131.

Discher, Dennis E., et al., "Emerging Applications of Polymersomes in Delivery: From Molecular Dynamics to Shrinkage of Tumors"; Prog. Polym. Sci; vol. 32; 2007; pp. 838-857.

Discher, Bohdana M., et al., "Polymersomes: Tough Vesicles Made from Diblock Copolymers"; Science; vol. 284; May 14, 1999; pp. 1142-1146.

O'Neil, Conlin P., et al., "A Novel Method for the Encapsulation of Biomolecules into Polymersomes via Direct Hydration"; Langmuir; vol. 25; Issue 16; 2009; pp. 9025-9029.

Lee, James C-M., et al., "Preparation, Stability, and In Vitro Performance of Vesicles Made with Diblock Copolymers"; Biotechnology and Bioengineering; vol. 73; No. 2; Apr. 20, 2001; pp. 135-145.

Ghoroghchian, P. Peter; "Bioresorbable Vesicles Formed Through Spontaneous Self-Assembly of Amphiphilic Poly(ethylene oxide)-block-polycaprolactone"; Macromolecules; vol. 7; Issue 39(5); 2006; pp. 1673-1675.

Kim, Younghoon, et al., "Polymersome Delivery of siRNA and Antisense Oligonucleotides"; J. Controlled Release; vol. 134; 2009; pp. 132-140.

Hearnden, Vanessa, et al., "Diffusion Studies of Nanometer Polymersomes Across Tissue Engineered Human Oral Mucosa"; Pharm. Research; vol. 26; No. 7; Jul. 2009; pp. 1718-1728.

Meng, Fenghua, et al., Biodegradable Polymersomes as a Basic for Artificial Cells: Encapsulation, Release and Targeting; J. Controlled Release; vol. 101; 2005; pp. 187-198.

Photos, Peter J., et al., "Polymer Vesicles in Vivo: Correlations with PEG Molecular Weight"; J. Controlled Release; vol. 90; 2003; pp. 323-334.

Ghoroghchian, P. Peter, et al., "Quantitative Membrane Loading of Polymer Vesicles"; Soft Matter; vol. 2; 2006; pp. 973-980.

Ghoroghchian, P. Peter, et al., "Near-Infrared-Emissive Polymersomes: Self-Assembled Soft Matter for in Vivo Optical Imaging" PNAS: vol. 102; No. 8; Feb. 22, 2005; pp. 2922-2927.

Bermudez, H., et al., "Effect of Bilayer Thickness on Membrane Bending Rigidity"; Langmuir; vol. 20; 2004; pp. 540-543.

Bermudez, Harry, et al., "Molecular Weight Dependence of Polymersome Membrane Structure, Elasticity, and Stability"; Macromolecules; vol. 35; 2002; pp. 8203-9208.

Massignani, Marzia, et al., "Controlling Cellular Update by Surface Chemistry, Size, and Surface Topology at the Nanoscale"; small; vol. 5; No. 21; 2009; pp. 2424-2432.

Blanazs, Adam, et al., "Tailoring Macromolecular Expression at Polymersome Surfaces"; Adv. Funct. Mater.; vol. 10; 2009; pp. 2906-2914.

Van Dongen, Stijn F.M., et al., "A Block Copolymer for Functionalisation of Polymersome Surfaces"; Macromol. Rapid Commun; vol. 29; 2008; pp. 321-325.

Christian, Natalie A., et al., Tat-functionalized Near-Infrared Emissive Polymersomes for Dendritic Cell Labeling; Bioconjugate Chem.; vol. 18; 2007; pp. 31-40.

Binder, Wolfgang H., et al., "Guiding the Location of Nanoparticles into Vesicular Structures: A Morphological Study"; Phys. Chem. Chem. Phys; vol. 9; 2007; pp. 6435-6441.

Lin, John L., et al., "Adhesion of Antibody-Functoinalized Polymersomes"; Langmuir; vol. 22; 2006; pp. 3975-3979.

Lin, John L., et al., The Effect of Polymer Chain Length and Surface Density on the Adhesiveness of Functionalized Polymersomes; Langmuir; vol. 20; 2004; pp. 5493-5500.

Pangu, Gautam D., et al., "Ultrasonically Induced Release From Nanosized Polymer Vesicles"; Macromol. Biosci.; vol. 10; 2010; pp. 546-554.

Kim, Min Sang, et al., "Biodegradable and pH-Sensitive Polymersome With Tuning Permeable Membrane for Drug Delivery Carrier"; Chem. Commun.; vol. 46; 2010; pp. 4481-4483.

Chen, Wei, et al., "pH Sensitive Degradable Polymersomes for Triggered Release of Anticancer Drugs: A comparative Study with Micelles"; J. Controlled Release; vol. 142; 2010; pp. 40-46.

Robbins, Gregory P., et al., "Photoinitiated Destruction of Composite Porphyrin—Protein Polymersomes"; J. Am. Chem. Soc; vol. 131; 2009; pp. 3872-3874.

Kim, Kyoung Taek, et al., "A Polymersome Nanoreactor With Controllable Permeability Induced by Stimuli-Responsive Block Copolymers"; Adv. Mater.; vol. 21; 2009; pp. 2787-2791.

Sanson, C., et al., "Temperature Responsive Poly(trimethylene Carbonate)-block-poly(L-glutamic acid) Copolymer: Polymersomes Fusion and Fission"; Soft Matter; vol. 6; 2010; pp. 1722-1730.

Castillo, Reina Veronica, et al., "Crystallization Kinetics and Morphology of Biodegradable Double Crystalline PLLA-b-PCL Diblock Copolyers; Macromolecules; vol. 43; 2010; pp. 4149-4160.

Wang, Feng., et al., "Biodegradable Vesicular Nanocarriers Based on Poly(ε-caprolactone)-block-poly(ethyl ethylene phosphate) for drug delivery"; Polymer; vol. 50; 2009; pp. 5048-5054.

Schatz, Christophe, "Polysaccharide-block-polypeptide Copolymer Vesicles: Towards Synthetic Viral Capsids"; Angew. Chem. Int. Ed.; vol. 48; 2009. pp. 2572-2575.

(56) References Cited

OTHER PUBLICATIONS

Rabotyagova, Olena S., et al., "Self-Assembly of Genetically Engineered Spider Silk Block Copolymers;" Biomacromolecules; vol. 10; 2009; pp. 229-236.
Katz, Joshua S., et al., "Membrane Stabilization of Biodegradable Polymersomes;" Langmuir; vol. 25; Issue 8; 2009; pp. 4429-4434.
Bromley, Elizabeth H.C., et al., "Peptide and Protein Building Blocks for Synthetic Biology: From Programming Miomolecules to Self-Organized Biomolecular Systems"; ACS Chem. Biology; vol. 3; No. 1; 2007; pp. 38-50.
Najafi, Farhood, et al., Biodegradable Micelles/Polymersomes from Fumaric/Sebacic Acids and Poly(ethylene glocol); Biomaterials; vol. 24; 2003; pp. 1175-1182.
Rameez, Shahid, et al., "Large Scale Production of Vesicles by Hollow Fiber Extrusion: A Novel Method for Generating Polymersome Encapsulated Hemoglobin Dispersions"; Langmuir; vol. 26; Issue 7; 2010; pp. 5279-5285.
Shum, Ho Cheung, et al., "Microfluidic Fabrication of Monodisperse Biocompatible and Biodegradable Polymersomes with Controlled Permeability"; J. Am. Chem. Soc; vol. 130; 2008; pp. 9543-9549.
Yildiz, M. E., et al., "Formation and Characterization of Polymersomes Made by a Solvent Injection Method"; Polym. Adv. Technol; vol. 18; 2007; pp. 427-432.
Dewirst, Mark W., et al., "Relationships Between Cycling Hypoxia, HIF-1, Angiogenesis and Oxidative Stress"; Radiation Research; vol. 172; Issue 6; 2009; pp. 653-665.
Palmer, Gregory M., et al., "Non-Invasive Monitoring of Intra-Tumor Drug Concentration and Therapeutic Response Using Optical Spectroscopy"; J. Controlled Release; vol. 142; 2010; pp. 457-464.
Dewhirst, Mark W., et al., "Utility of Functional Imaging in Prediction or Assessment of Treatment Response and Prognosis Following Thermotheraphy"; Int. J. Hyperthermia; vol. 26; Issue 3; 2010; pp. 283-293.
Zhang, Guoqing, et al., "A Dual-Emissive-Materials Design Concept Enables Tumour Hypoxia Imaging"; Nature Materials; vol. 8; Sep. 2009 pp. 747-751.
Palmer, Gregory M. et al., "Quantitative Diffuse Reflectance of Fluorescence Spectroscopy: A Tool to Monitor Tumor Physiology in Vivo;" J. Biomed Opt; vol. 14; Issue 2; 2009; p. 024010.
Hardee, Matthew E., et al., "Novel Imaging Provides New Insights into Mechanisms of Oxygen Transport in Tumors"; Curr. Mol. Med; vol. 9; Issue 4; May 2009; pp. 435-441.
Dewhirst, Mark W. et al., "Cycling Hypoxia and Free Radicals Regulate Angiogenesis and Radiotherapy Response"; Nature Reviews | Cancer; vol. 8; Jun. 2008; pp. 425-438.
Sorg, Brian S. et al., "Hyperspectral Imaging of Hemoglobin Saturation in Tumor Microvasculature and Tumor Hypoxia Development;"; J. of Biomedical Optics; vol. 10; Issue 4; 2005; p. 44004.
Dewhirst, Mark W., et al., "Exploring the Role of HIF-1 in Early Angiogenesis and Response to Radiotheraphy"; Radiotherapy and Oncology; vol. 83; 2007; pp. 249-255.
Moeller, B. J., et al., HIF-1 and Tumour Radiosensitivity; British J. of Cancer; vol. 95; 2006; pp. 1-5.
Moeller, Benjamin J., et al. "Pleiotropic Effects of HIF-1 Blockade on Tu mor Radiosensitivity"; Cancer Cell; vol. 8; Aug. 2005; pp. 99-110.
Arifin, Dian R., et al., "Polymersome Encapsulated Hemoglobin: A Novel Type of Oxygen Carrier"; Biomacromolecules; vol. 6; 2005; pp. 2172-2181.
Rameez, Shahid, et al., "Biocompatible and Biodegradable Polymersome Encapsulated Hemoglobin: A Potential Oxygen Carrier"; Bioconjugate Chem.; vol. 19; 2008. pp. 1025-1032.
Ghoroghchian, P. Peter, et al., "In Vivo Fluorescence Imaging: A Personal Perspective"; WIREs Nanomedicine and Nanobiotechnology; vol. 1; Mar./Apr. 2009; pp. 156-167.
Duncan, Timothy V., et al., "Ultrafast Excited-State Dynamics of Nanoscale Near-Infrared Emissive Polymersomes"; J. Am. Chem. Soc; vol. 130; 2008; pp. 9773-9784.
Ghoroghchian, P. Peter, et al., "Controlling Bulk Optical Properties of Emissive Polymersomes Through Intramembranous Polymer-Fluorophore Interactions"; Chem. Mater; vol. 19(6); Mar. 20, 2007; pp. 1309-1318.
Ghoroghchian, P. Peter, et al., "Broad Spectral Domain Fluorescence Wavelength Modulation of Visible and Near-Infrared Emissive Polymersomes"; J. Am. Chem. Soc; vol. 127; 2005; pp. 15388-15390.
Christian, Natalie A., et al., "In Vivo Dendritic Cell Tracking Using Flourescence Lifetime Imaging and Near-Infrared-Emissive Polymersomes"; Mol. Imaging Biol; vol. 11; 2009; pp. 167-177.
Hearnden, V., et al., "Penetration of Polymersome Drug and Gene Delivery Nanoparticles iInto in Vitro Models of Head and Neck Cancer and Tissue Engineered Oral Mucosa"; Oral Oncology Supplement 3; Oral Abstracts; 2009; pp. 56-122.
Li, Shuliang, et al., "Self-Assembled Poly(butadiene)-b-Poly(ethylene oxide) Polymersomes as Paclitaxel Carriers"; Biotechnol. Prog.; vol. 23; 2007; pp. 278-285.
Ahmed, Fariyal, et al., "Biodegradable Polymersomes Loaded with Both Paclitaxel and Doxorubicin Permeate and Shrink Tumors, Inducing Apoptosis in Proportion to Accumulated Drug"; J. Controlled Release; vol. 116; 2006; pp. 150-158.
Zhang, Ziaolan et al., "Key Parameters Affecting the Initial Leaky Effect of Hemoglobin-Loaded Nanoparticles as Blood Substitutes"; J. Mater Sci: Mater Med; vol. 19; 2008; pp. 2463-2470.
Dewhirst, M.W., et al., "Microvascular Studies on the Origins of Perfusion-Limited Hypoxia"; British Journal of Cancer; vol. 74; Suppl. XXVII; 1996; pp. S247-S251.
Zupancich, John A., et al., "Aqueous Dispersions of Poly(ethylene oxide)-b-poly(γ-methyl-ϵ-caprolactone) Block Copolymers"; Macromolecules; vol. 39; 2006; pp. 42886-42888.
Hahn, Jason S., et al., "Stroma-Free Human Hemoglobin A Decreases R3230Ac Rat Mammary Adenocarcinoma Blood Flow and Oxygen Partial Pressure"; Radiation Research; vol. 147; No. 2; Feb. 1997; pp. 185-194.
Arifin, Dian R., et al., "Determination of Size Distribution and Encapsulation Efficiency of Liposome-Encapsulated Hemoglobin Blood Substitutes Using Asymmetric Flow Field-Flow Fractionation Coupled with Multi-Angle Statis Light Scattering"; Biotechnol. Prog.; vol. 19; 2003; pp. 1798-1811.
Sakai, Hiromi, et al., "NO and CO Binding P rofiles of Hemoglobin Vesicles as Artificial Oxygen Carriers"; Biochimica et Biophysica Acta; vol. 1784; 2008; pp. 1441-1447.
Frauenfelder, H., et al., Myoglobin: The Hydrogen Atom of Biology and a Paradigm of Complexity; PNAS; vol. 100; No. 15; Jul. 22, 2003; pp. 8615-8617.
Herold, Susanna, et al., "Kinetic and Mechanistic Studies of the NO•-Mediated Oxidation of Oxymyoglobin and Oxyhemoglobin"; Biochemistry; vol. 40; 2001; pp. 3385-3395.
Niehaus, G. Ulrich, et al., "Ligand Binding to Heme Proteins: The Effect of Light on Ligand Binding in Myoglobin," Biochemistry; vol. 33; 1994; pp. 13413-13430.
Ansari, Anjum, "Conformational Relaxation and Ligand Binding in Myoglobin," Biochemistry; vol. 33; 1994; pp. 5128-5145.
Mourant, Judith R., et al., "Ligand Binding to Heme Proteins: II. Transitions in the Heme Pocket of Myoglobin"; Biophysical Journal; vol. 65; Oct. 1993; pp. 1496-1507.
Kanner, Joseph et al., "Nitric Oxide as an Antioxidant," Archives of Biochemistry and Biophysics; vol. 289; No. 1; Aug. 15, 1991; pp. 130-136.
Chance, Britton, et al., "Annual Rev. Biophys. Biophys. Chem"; Univ. Kentucky; vol. 20; Dec. 15, 2011; pp. 1-30, <www.annualreviews.org>.
Chance, Britton, et al., "Time-Resolved Spectroscopy of Hemoglobin and Myoglobin in Resting and Ischemic Muscle," Analytical Biochemistry; vol. 174; 198; pp. 698-707.
Privalov, P. L., et al., "Cold Denaturation of Myoglobin," J. Mol. Biol.; 1986; vol. 190, pp. 487-498.
Helcke, G. A., et al., "Electron Resonance Studies of Haemoglobin Derivatives. III. Line-Width and g-Value Measurements of Acid-Met Myoglobin and of Met Myoglobin Azide Derivatives"; Proceedings of the Royal Society of London; Series B; Biological Sciences; vol. 169; No. 1016; Feb. 27, 1968; pp. 275-288.

(56) References Cited

OTHER PUBLICATIONS

Moeller, Benjamin J., et al., "Hypoxia and Radiotheraphy: Opportunities for Improved Outcomes in Cancer Treatment", Cancer Metastasis Rev; vol. 26, 2007, pp. 241-248.
Kong, Garheng, et al., "Characterization of the Effect of Hyperthermia on Nanoparticle Extravasation from Tumor Vasculature"; Cancer Research; vol. 61; Apr. 1, 2001; pp. 3027-3032.
Kong, Garheng, et al., "Hyperthermia Enables Tumor-Specific Nanoparticle Delivery: Effect of Particle Size"; Cancer Research; vol. 60, Aug. 15, 2000; pp. 4440-4445.

Moeller, Benjamin J., et al., "Raising the Bar. How HIF-1 Helps Determine Tumor Radiosensitivity"; Cell Cycle; vol. 3:9; Sep. 2004; 1107-1110.
Hammadi, Amar, et al., "Stimulation of iNOS Expression and Apoptosis Resistance in B-cell Chronic Lymphocytic Leukemia (B-CLL) cells through engagement of Toll-like Receptor 7 (TLR-7) and NF-κB activation"; Nitric Oxide; vol. 19, 2008; pp. 138-145.
International Preliminary Report on Patentability issued in PCT Application No. PCT/US2011/033190, mailed on Nov. 1, 2012.

\* cited by examiner

T= 37° C

N = 4 samples at each data point

Individual data points for each sample vary by less than 10% of the value displayed at each time interval

BIODEGRADABLE NANOPARTICLES AS NOVEL HEMOGLOBIN-BASED OXYGEN CARRIERS AND METHODS OF USING THE SAME

RELATED APPLICATIONS

This application claims the benefit of priority to U.S. Provisional Application No. 61/326,222, entitled "Biodegradable Polymersomes as Novel Hemoglobin-Based Oxygen Carriers and Methods of Using the Same" filed Apr. 20, 2010; and U.S. Provisional Application No. 61/430,628, entitled "Biodegradable Polymersomes as Novel Hemoglobin-Based Oxygen Carriers and Methods of Using the Same" filed Jan. 7, 2011, the entire contents of both of which are hereby incorporated by reference.

GOVERNMENT SUPPORT

This invention was made using funds from the National Institute of Health (Study ID#1R43HL103388-01). The Government has certain rights in this invention.

FIELD OF INVENTION

The various embodiments include compositions and methods for synthesis and delivery of synthetic oxygen carriers including oxygen-binding compounds compartmentalized in biodegradable polymer vesicles (e.g., polymersomes).

BACKGROUND OF THE INVENTION

Currently, there is a shortage in the number of red blood cell (RBC) units available for blood transfusions. Donated human red blood cells (currently the only source for these transfusions) do not adequately meet current demands and are unlikely to meet future demands. For example, in the United States, 14 million red blood cell units are made available for transfusions each year, and an annual deficit of 1 million units still exists. Internationally, the deficit is around 200 million units annually. In the future, these deficits may become even more severe, as the current deficit projections do not take into account the more acute need for blood in cases of mass civilian casualties, such as natural disasters, terrorist attacks and wars.

The shortage in red blood cell units and the lack of suitable substitutes results in many preventable deaths. For example, more than 530,000 women die each year during pregnancy or childbirth, with hemorrhage being the leading cause of death (accounting for up to 44% of maternal deaths in some areas of sub-Saharan Africa). Many of these deaths could be prevented with the proper supply of red blood cell units or with a proper substitute for red blood cell transfusions.

While the current deficits are in part due to a shortage in the number of blood donors, a number of other factors also contribute to the current crisis. Several of these factors relate to the pool of available donated human red blood cells being limited by existing obstacles to safe transfusion. For example, red blood cell units may carry infectious diseases and many multi-level proactive interventional programs of stringent red blood cell donor screening and expensive nucleic acid testing procedures have been implemented to protect recipients. With each new emerging disease, new diagnostic tests are performed, further limiting the available donor pool and further increasing costs. In addition, donated human red blood cells contain proteins and cytokines that may cause reactions in up to 2% of transfusions with symptoms ranging in severity from mild allergic reactions to severe shock and even death. Also, red blood cell transfusions may lead to various metabolic conditions (e.g. hyperkalemia, hypocalcemia and alkalosis), and multiple red blood cell transfusions may exert an immunosuppressive effect on the recipient, increasing risk of hospital-acquired infections.[1] These potential complexities further increase costs associated with donor red blood cell transfusions.

In addition to the above-mentioned obstacles to safe transfusion, costs are also increased due to requirements for cross-matching donor and recipient red blood cell units before transfusion, as well as the short storage life (typically 15 days) and expensive storage requirements (e.g., must be kept at 2-3° C., special storage solutions are required to extend red blood cell life to 42 days, etc.) of red blood cell units.[2] While there have been many recent improvements in technology, the collection and storage of donated red blood cells remains a difficult and expensive task. There is a need for a less expensive and more effective alternative to donated human red blood cell transfusions.

A list of publications referenced in this disclosure follows, each of which is incorporated by reference for the cited portions of their respective disclosures:

1. L. M. Napolitano, Crit. Care Clin, 25: 279-301 (2009).
2. W. J. Williams, E. Beutler, A. J. Erslev, R. W. Rundles, Hematology. McGraw-Hill Book Company, New York (1977).
3. T. Standl, Transfus. Med. Hemother., 21: 262-268 (2004).
4. A. I. Alayash, Nature, 3: 152-159 (2004).
5. T. M. S. Chang, Crit. Care Med., 32: 612-613 (2004).
6. B. T. Kjellstrom, J. Intern. Med., 253: 495-497 (2003).
7. Y. O. Schumacher, M. Ashenden, Sports Med., 34: 141-150 (2004).
8. K. C. Lowe, E. Ferguson, J. Intern. Med., 253: 498-507 (2003).
9. H. G. Klein, Oncology, 16: 147-151 (2002).
10. S. E. Hill, Can. J. Anesth., 48: S32-S40 (2001).
11. R. M. Winslow, J. Intern. Med., 253: 508-517 (2003).
12. E. Niiler, Nature Biotechnol., 20: 962-963 (2002).
13. E. Maevsky, G. Ivanitsky, L. Bogdanova, O. Axenova, N. Karmen, E. Zhiburt, R. Senina, S. Pushkin, I. Maslennikov, A. Orlov I. Marinicheva, Art. Cells, Blood Subs., and Biotech., 33: 37-46 (2005).
14. P. E. Keipert, Adv. Exp. Med. Biol., 540: 207-213 (2003).
15. C. P. Stowell, Curr. Opin. Hematol., 9: 537-543 (2002).
16. J. G. Riess, Chem. Rev., 101: 2797-2919 (2001).
17. A. S. Rudolph, A. Sulpizio, P. Hieble, V. MacDonald, M. Chavez, G. Feuerstein, J. Applied Phys., 82: 1826-1835 (1997).
18. E. Moore, J. Am. Coll. Surgeons, 196: 1-17 (2003).
19. T. M. S. Chang, Trends Biotechnol., 17: 61-67 (1999).
20. H. Sakai, K. Tomiyama, K. Sou, S. Takeoka, E. Tsuchida, Bioconjugate Chem., 11: 425-432 (2000).
21. W. T. Phillips, R. W. Klipper, V. D. Awasthi, A. S. Rudolph, R. Cliff, V. Kwasiborski, B. A. Goins, J. Pharmacol. Exp. Ther., 288: 665-670 (1999).
22. R. O. Wright, B. Magnani, M. W. Shannon, A. D. Woolf, Ann. of Emergency Med., 28: 499-503 (1996).
23. Y. Teramura, H. Kanazawa, H. Sakai, S. Takeoka, E. Tsuchida, Bioconjugate Chem., 14: 11711176 (2003).
24. S. Takeoka, H. Sakai, T. Kose, Y. Mano, Y. Seino, H. Nishide, E. Tsuchida, Bioconjugate Chem., 8: 539-544 (1997).
25. R. M. Winslow, Drug Delivery Rev. 40: 131-142 (2000).
26. R. M. Winslow, Annu. Rev. Med. 50: 337-353 (1999).
27. T. M. S. Chang, Crit. Care Med. 32: 612-613 (2004).

28. T. M. S. Chang, Curr. Opin. Invest. Drugs, 3: 1187-1190 (2002).
29. H. Sakai, S. Takeoka, S. I. Park, T. Kose, H. Nishide, Y. Izumi, A. Yoshizu, K. Kobayashi, E. Tsuchida, Bioconjugate Chem., 8: 23-30 (1997).
30. M. C. Farmer, B. P. Gaber, Methods Enzymol. 149: 184-200 (1987).
31. A. S. Rudolph, R. W. Klipper, B. A. Goins, W. T. Phillips, Proc. Natl. Acad. Sci. U.S.A. 88: 097610980 (1991).
32. D. Bhadra; S. Bhadra; P. Jain; N. K. Jain, Pharmazie, 57:5-29 (2002).
33. H. Sakai; A. G. Tsai; S. I. Park, S. Takeoka, H. Nishide, E. Tsuchida; M. Intaglietta, J. Biomed. Mater. Res. 40: 66-78 (1997).
34. K. Nakai, A. Usuba, T. Ohta, M. Kuwabara, Y. Nakazato, R. Motoki, T. A. Takahashi, Artif. Organs 22: 320-325 (1998).
35. M. Antonietti, S. Forster, Adv. Mater. 15: 1323-1333 (2003).
36. W. T. Phillips, R. W. Klipper, V. D. Awasthi; A. S. Rudolph; R. Cliff, V. Kwasiborski, B. A. Goins, J. Pharmacol. Exp. Ther. 288: 665-670 (1999).
37. S. M. Moghimi, J. Szebeni, J. Prog. Lipid Res. 42: 463-478 (2003).
38. B. M. Discher, Y. Y. Won, D. S. Ege, J. C. Lee, F. S. Bates, D. E. Discher, D. A. Hammer, Science 284: 1143-1146 (1999).
39. P. P. Ghoroghchian, G. Li; D. H. Levine, K. P. Davis, F. S. Bates, D. A. Hammer, M. J. Therien, Macromolecules 39(5): 1673-1675 (2006).
40. J. M. Lee, H. Bermudez, B. M. Discher, M. A. Sheehan, Y. Y. Won, F. S. Bates, D. E. Discher, Biotechnol. and Bioengg. 73(2): 135-145 (2001).
41. G. P. Robbins, M. Jimbo, J. Swift, M. J. Therien, D. A. Hammer, I. J. Dmochowski, J. Am. Chem. Soc. 131 (11): 3872-3874 (2009).
42. S. M. Moghimi, A. C. Hunter, J. C. Murray, Pharmacol. Rev. 53:283-318 (2001).
43. H. Otsuka, Y. Nagasaki, K. Kataoka, Adv. Drug Delivery Rev. 55: 403-419 (2003).
44. C. Allen, J. N. Han, Y. S. Yu, D. Maysinger, A. Eisenberg, A. J. Controlled Release 63: 275-286 (2000).
45. V. R. Sinha, K. Bansal, R. Kaushik; R. Kumria, A. Trehan, Int. J. Pharm. 278: 1-23 (2004).
46. Y. Y. Won, A. K. Brannon, H. T. Davis, F. S. Bates, J. Phys. Chem. B 106: 3354-3364 (2002).
47. H. Bermudez, A. K. Brannan, D. A. Hammer, F. S. Bates, D. E. Discher, Macromolecules 35: 8203-8208 (2002).
48. P. J. Photos, L. Bacakova, B. Discher, F. S. Bates, D. E. Discher, J. Contr. Release 90: 323-334 (2003).
49. D. E. Discher, A. Eisenberg, Science 297: 967-973 (2002).
50. D. R. Arifin, A. F. Palmer, Biotechnol. Prog. 19: 1798-1811 (2003).
51. D. R. Arifin, A. F. Palmer, Biomacromolecules 6 (4): 2172-2181 (2005).
52. S. Rameez, H. Alosta, A. F. Palmer, Bioconjugate Chem. 19:1025-1032 (2008).
53. J. Zupancich, F. S. Bates, M. A. Hillmyer, Macromolecules 39:4286-4288 (2006).
54. H. Jansson, J. Swenson, J. Chem. Phys 128: 245104: 1-7 (2008).
55. H. Sakai, A. Sato, K. Masuda, S. Takeoka, E. Tsuchida, J. Biol. Chem. 283 (3): 1508-1517 (2008).
56. K. Nakai, T. Ohta, I. Sakuma, K. Akama, Y. Kobayashi, S. Tokuyama, A. Kitabatake, Y. Nakazato, T. A. Takahashi, S. Sekiguchi, J. Cardiovasc. Pharmacol. 28: 115-123 (1996).
57. H. Sakai, K. Hamada, S. Takeoka, H. Nishide, E. Tsuchida, Polymer Adv. Technol. 7: 639-644 (1996).
58. S. Kaneda, T. Ishizuka, H. Goto, T. Kimura, K. Inaba, H. Kasukawa, Artificial Organs 33(2):146-152 (2009).
59. H. Sakai, A. Sato, P. Sobolewski, S. Takeoka, J. A. Frangos, K. Kobayashi, M. Intaglietta, E. Tsuchida, Biochim. et Biophys. Acta 1784: 1441-1447 (2008).
60. S. Usami, H. H. Chen, Y. Zhao, S. Shien, R. Skalak, Ann. Biomed. Eng., 21, 77-83 (1993).
61. D. K. Brunk, D. A. Hammer, Biophys J. 72: 2820-2833 (1997).
62. O. S. Finikova, A. Y. Lebedev, A. Aprelev, T. Troxler, F. Gao, C. Garnacho, S. Muro, R. M. Hochstrasser, S. A. Vinogradov, Chemphyschem. 9(12):1673-1679 (2008).
63. S. Sakadzi, S. Yuan, E. Dilekoz, S. Ruvinskaya, S. A., Vinogradov, C. Ayata, D. A. Boas, Appl Opt. 48(10): D169-77 (2009).

SUMMARY OF THE INVENTION

The various embodiments provide compositions and methods for making, storing and administering oxygen carriers having an oxygen-binding compound encapsulated in a polymer vesicle such as a polymersome. The various embodiments provide compositions and methods for making, storing and administering artificial blood substitutes that may include hemoglobin, myoglobin, or other oxygen binding compounds. The oxygen carriers of the various embodiments may include polymersomes comprising of poly(ethylene oxide)-block-poly(ε-caprolactone) (PEOb-PCL) and/or related diblock copolymers of poly(ethylene oxide)-block-poly(γ-methyl ε-caprolactone) (PEO-b-PMCL) for effective oxygen delivery, including tunable oxygen-binding capacities, uniform and appropriately small size distributions, human bloodlike viscosities and oncotic properties, as well as ease of mass production and affordable storage.

In some embodiments, the invention relates to a polymersome comprising at least one biocompatible polymer and at least one biodegradable polymer. In some embodiments, the invention relates to a composition comprising a polymersome comprising polyethylene oxide, wherein the weight fraction of polyethylene oxide is from about 10 to about 20 percent of the total weight of the block copolymer. In some embodiments, the composition comprises a polymersome wherein the biocompatible polymer is chosen from: poly(ethylene oxide), poly(ethylene glycol), or a combination thereof; and wherein the biodegradable polymer is chosen from poly(ε-caprolactone), poly(γ-methyl ε-caprolactone), or a combination thereof. In some embodiments, the polymersome comprises a diblock copolymer comprising at least one biocompatible polymer and at least one biodegradable polymer. In some embodiments, the polymersome comprises a triblock copolymer comprising at least one biocompatible polymer and at least one biodegradable polymer. In some embodiments, the polymersome comprises a biodegradable polymer, wherein the biodegradable polymer is a block copolymer of poly(ethylene oxide) and poly(γ-methyl)ε-caprolactone; wherein the polyethylene oxide has a number average molecular weight from about 1.0 to about 4.0 kiloDaltons, and wherein the weight fraction of polyethylene oxide is from about 17 to about 28 percent of the total weight of the block copolymer. In some embodiments, the polymersome comprises a biodegradable polymer, wherein the biodegradable polymer is a block copolymer of poly(ethylene oxide) and poly(ε-caprolactone); and wherein the polyethylene oxide has a number average molecular weight from about 1.0 kD to about 4.0 kD. In some embodiments, the polymersome comprises polyethylene oxide, wherein the weight fraction of polyethylene oxide is from about 10 to about 20 percent of the total weight of the block copolymer. In some embodiments, the polymersome comprises a biodegradable polymer, wherein the biodegradable polymer is a block copolymer of poly(ethylene oxide) and poly(ε-caprolactone); and wherein the polyethylene oxide has a number average molecular weight from about 1.0 kD to about 4.0 kD; and wherein the weight fraction of polyethylene oxide is from about 10 to about 20 percent of the total weight of the block copolymer. In some embodiments, the polymersome comprises a biodegradable polymer, wherein the biodegradable polymer is a block copolymer of poly(ethylene oxide) and poly(ε-caprolactone); wherein the weight fraction of polyethylene oxide is from about 18 to about 28 percent of the total weight of the block copolymer. In some embodiments, the polymersome comprises a biodegradable polymer, wherein the biodegradable polymer is a block copolymer wherein at least one block is poly(ethylene oxide) and one block is poly (ε-caprolactone), and wherein the polyethylene oxide has a number average molecular weight from about 1.5 to about 3.8 kD, and wherein the weight fraction of polyethylene oxide is from about 10 to about 30 percent of the total weight of the block copolymer. In some embodiments, the polymersome comprises a biodegradable polymer, wherein the biodegradable polymer is a block copolymer wherein at least one block is poly(ethylene oxide) or poly(ethylene glycol) wherein the weight fraction of poly(ethylene oxide) or poly(ethylene glycol) is from about 30 to about 50 percent of the total weight of the copolymer. In some embodiments, the polymersome comprises a diblock copolymer, wherein at least one polymer block comprises poly(γ-methyl ε-caprolactone) with a number average molecular weight that is from about 4 kiloDaltons to about 10 kiloDaltons. wherein the polymersome comprises at least one diblock copolymer comprising poly(ethylene oxide)) and poly(ε-caprolactone), wherein the poly(ethylene oxide)) has a number average molecular weight that is about 2 kiloDaltons and the poly(ε-caprolactone) has a number average molecular weight that is about 12 kiloDaltons. In some embodiments, the polymersome comprises at least one diblock copolymer comprising poly(ethylene oxide)) and poly(ε-caprolactone), wherein the poly(ethylene oxide)) has a number average molecular weight that is about 1.8 kiloDaltons to about 1.9 kiloDaltons and the poly(ε-caprolactone) has a number average molecular weight that is about 8 kiloDaltons to about 9.5 kiloDaltons.

In some embodiments, the invention relates to a pharmaceutical composition that comprises an oxygen carrier, and, optionally, a pharmaceutically acceptable carrier. In some embodiments, the invention relates to a pharmaceutical composition comprising the oxygen carrier of any of the disclosed embodiments herein. In some embodiments, the pharmaceutical composition comprises an oxygen carrier for treatment or prevention of reduced tissue oxygenation in an effective amount for a subject in need thereof. In some embodiments, the pharmaceutical composition comprises an oxygen carrier for increasing the rate of wound healing in an effective amount for a subject in need thereof. In some embodiments, the pharmaceutical composition comprises an oxygen carrier for treatment or prevention of an immunologic, rheumatologic, oncologic or inflammatory condition in an effective amount for a subject in need thereof. In some embodiments, the pharmaceutical composition comprises an oxygen carrier for treatment or prevention of cellular dysplasia, hyperplasia, malignant cancer, or tumor growth in an effective amount for a subject in need thereof.

In some embodiments, the invention relates to kits comprising a composition, pharmaceutical composition or polymersome disclosed herein.

In some embodiments, the invention relates to a method of manufacturing am effective amount of a medicament comprising the compositions, pharmaceutical compositions or polymersomes disclosed herein for use in treatment or prevention of immunologic, rheumatologic, oncologic or inflammatory condition. In some embodiments, the invention relates to a method of manufacturing am effective amount of a medicament comprising the compositions, pharmaceutical compositions or polymersomes disclosed herein for use in treatment or prevention of oxygen deficiency or ischemia. In some embodiments, the invention relates to a method of manufacturing am effective amount of a medicament comprising the compositions, pharmaceutical compositions or polymersomes disclosed herein for use in treatment or prevention of cellular dysplasia, hyperplasia, malignant cancer, or tumor growth. In some embodiments, the invention relates to a method of manufacturing am effective amount of a medicament comprising the compositions, pharmaceutical compositions or polymersomes disclosed herein for use in increasing the rate of wound healing.

Various embodiments provide a composition of matter having an oxygen carrier that includes plurality of polymers and an oxygen-binding compound. The oxygen carrier may be a polymer vesicle, a nanoparticle-based vesicle and/or a polymersome. The oxygen carrier may include a poly(peptide), a poly(saccharide) and/or a poly(nucleic acid).

In various embodiments, the oxygen-binding compound may included within the polymer vesicle, the nanoparticle-based vesicle and/or polymersome. The oxygen-binding compound may be a naturally occurring protein, a recombinant protein, a recombinant polypeptide, a synthetic polypeptide, a chemical synthesized by an animal, a synthetic small molecule, a carbohydrate, a nucleic acid, a lipid or a polymer. The oxygen-binding compound may be a compound derived from one or more of a naturally occurring protein, a recombinant protein, a recombinant polypeptide, a synthetic polypeptide, a chemical synthesized by an animal, a synthetic small molecule, a carbohydrate, a nucleic acid, a lipid and/or a polymer. The oxygen-binding compound may be hemoglobin and/or a derivative of hemoglobin.

At least one of the plurality of polymers may be a biodegradable polymer. At least one of the plurality of polymers may be a biocompatible polymer. The biocompatible polymer may be poly(ethylene oxide) and/or poly(ethylene glycol). The biodegradable polymer may be poly(ε-caprolactone), poly(γ-methyl ε-caprolactone) and/or a block copolymer of poly(ethylene oxide) and poly(ε-caprolactone). The poly (ethylene oxide) may have an number-average molecular weight from about 1.5 kiloDalton to about 4.0 kiloDalton. The weight fraction of the poly(ethylene oxide) may be from about 11 to about 20 percent of the total weight of the block copolymer.

In various embodiments, the biodegradable polymer may be a block copolymer of poly(ethylene oxide) and poly(γ-methyl ε-caprolactone), the poly(ethylene oxide) may have a number-average molecular weight from about 1.5 kiloDalton to about 4.0 kiloDalton, and a weight fraction of poly(ethylene oxide) may be from about 18 to about 28 percent of the total weight of the block copolymer. In some embodiments, the poly(ethylene oxide) may have a number-average molecular weight from about 1.5 to about 3.8 kiloDalton and a weight fraction from about 10 to about 30 percent of the total weight of the block copolymer.

In various embodiments, at least one of the plurality of polymers may be a block copolymer of which at least one polymer block is poly(ethylene oxide) or poly(ethylene glycol) having a weight fraction from about 30 to about 50 percent of the total weight of the copolymer. In various embodiments, at least one of the plurality of polymers may be a block copolymer of which at least one polymer block is poly(ε-caprolactone) having a weight fraction from about 50 to about 70 percent of the total weight of the copolymer. In various embodiments, at least one of the plurality of polymers may be a block copolymer of which at least one polymer block is poly(γ-methyl ε-caprolactone) having a weight fraction from about 50 to about 70 percent of the total weight of the copolymer. In various embodiments, at least one of the plurality of polymers is a diblock copolymer of which at least one polymer block comprises poly(ε-caprolactone) with a number-average molecular weight from about 9 kiloDalton to about 23 kiloDalton.

In various embodiments, the number-average molecular weight may be from about 9.5 kiloDalton to about 22.2 kiloDalton. In various embodiments, at least one of the plurality of polymers may be a diblock copolymer of which at least one polymer block comprises poly(γ-methyl ε-caprolactone) having a number-average molecular weight from about 4 kiloDalton to about 10 kiloDalton. In an embodiment, the number-average molecular weight may be from about 4.8 kiloDalton to about 9.5 kiloDalton.

In various embodiments, at least one of the plurality of polymers may be a diblock copolymer comprising poly(ethylene oxide) and poly(ε-caprolactone). The poly(ethylene oxide) may have a number-average molecular weight of about 2 kiloDalton and the poly(ε-caprolactone) may have a number-average molecular weight of about 12 kiloDalton. The poly(ethylene oxide) may have a number average molecular weight that is from about 1.8 kiloDalton to about 1.9 kiloDalton and the poly(ε-caprolactone) may have a number average molecular weight that is from about 8 kiloDalton to about 9.5 kiloDalton.

In various embodiments, the composition may include oxygen dispersed within the polymers of the oxygen carrier, oxygen dispersed within an aqueous core of the oxygen carrier, and/or a ligand conjugated to the surface of the oxygen carrier. In various embodiments, the composition may include at least one pharmaceutically active agent. The pharmaceutically active agent may be contained within the oxygen carrier. In an embodiment, the pharmaceutically active agent may be optionally contained within the oxygen carrier.

In various embodiments, the oxygen carrier may include an allosteric effector. In various embodiments, the oxygen carrier may have a diameter from about 50 nm to about 5 μm. The oxygen carrier may have a membrane thickness from about 5 nm to about 30 nm. The oxygen carrier may have a multiblock copolymer layer structure comprising multiblock copolymer chains having hydrophilic and hydrophobic blocks. Two or more of the copolymer chains may be covalently bonded to one another.

In various embodiments, the polymersomes may have an aqueous interior, hydrophobic polymersome membrane and/or a hydrophilic surface. The allosteric effector may be compartmentalized within the aqueous interior, hydrophobic polymersome membrane and/or hydrophobic membrane of the polymersome. The allosteric effector may be a naturally occurring molecule, a recombinant molecule, a synthetic molecule and/or a polymer. The allosteric effector may modify oxygen-binding through hydrogen ions, carbon dioxide, and/or 2,3-bisphosphoglycerate. The pharmaceutically active agent may be compartmentalized within the aqueous interior, hydrophobic polymersome membrane and/or hydrophobic membrane of the polymersome.

In various embodiments, the oxygen-binding compound may be covalently linked to the hydrophilic surface of the polymersome. A pharmaceutically active agent may be covalently linked to the hydrophilic surface of the polymersome. An allosteric effector may be covalently linked to the hydrophilic surface of the polymersome.

In various embodiment, the copolymer layer structure may be bilayer. In various embodiments, the oxygen carrier may be biodegradable. The oxygen carrier may include at a hydrophilic block polymer. The hydrophilic block polymer may be poly(ethylene oxide), poly(acrylic acid), poly(ethylene glycol), or any combination thereof. The hydrophilic block polymer may be poly(caprolactone), poly(methylcaprolactone), poly(menthide), poly(lactide), poly(glycolide), poly(methylglycolide), poly(dimethylsiloxane), poly(isobutylene), poly(styrene), poly(ethylene), poly(propylene oxide), or any combination thereof.

Various embodiments provide a method of manufacturing a composition that includes an oxygen carrier. An organic solution comprising a plurality of polymers may be prepared and the organic solution may be exposing to a plastic, polytetrafluoroethylene, or glass surface. The organic solution may be dehydrated on the plastic, polytetrafluoroethylene, or glass surface to create a film of polymers. The film of polymers may be rehydrated in an aqueous solution having an oxygen-binding molecule. The polymers may be cross-linked in the aqueous solution via chemical modification. The oxygen-binding molecule may be hemoglobin. The aqueous solution may include an allosteric effector, a pharmaceutically active agent, or a combination thereof. Cross-linking the polymers in the aqueous solution via chemical modification may include cross-linking the polymers via a photoactive chemical and UV light. Cross-linking the polymers in the aqueous solution via chemical modification may include cross-linking the polymers via a chemical modification of 2,2-dimethoxy-2-phenylacetophenone. Cross-linking the polymers in the aqueous solution via chemical modification may include lyophilizing the polymers after cross-linking. The polymers may be purified through a polycarbonate filter with a pore size of between about 50 kiloDaltons and about 1 million kiloDaltons.

The organic solution may include a biocompatible polymer. The organic solution may include a biodegradable polymer. The biocompatible polymer may be poly(ethylene oxide) and/or poly(ethylene glycol). The biodegradable polymer may be poly(ε-caprolactone) and/or poly(γ-methyl ε-caprolactone). The organic solution may include a block copolymer in which at least one block is poly(ε-caprolactone). The weight fraction of poly(ε-caprolactone) may be from about 50 to 70 percent of the total weight of the copolymer. The organic solution may include a block copolymer in which at least one block is poly(γ-methyl ε-caprolactone). The weight fraction of poly(γ-methyl ε-caprolactone) may be from about 50 to 70 percent of the total weight of the copolymer. The organic solution may include a diblock copolymer having at least one biocompatible polymer and at least one biodegradable polymer. The diblock biocompatible polymer may be poly(ethylene oxide) and/or poly(ethylene glycol) and the diblock biodegradable polymer may be poly(ε-caprolactone) and/or poly(γ-methyl ε-caprolactone).

In various embodiments, the organic solution may include a triblock copolymer having a biocompatible polymer and/or a biodegradable polymer. The triblock biocompatible polymer may include poly(ethylene oxide) and/or poly(ethylene glycol) and the triblock biodegradable polymer may include poly(ε-caprolactone) and/or poly(γ-methyl ε-caprolactone).

In various embodiments, the organic solution may include a block copolymer in which at least one block is poly(ethylene oxide) and one block is poly (γ-methyl ε-caprolactone), the poly(ethylene oxide) having a number-average molecular weight between about 1.5 and about 3.8 kiloDalton. The poly(ethylene oxide) may have a weight fraction between about 10 and about 30 percent of the total weight of the block copolymer. The poly(ethylene oxide) may have a weight fraction between about 30 and about 50 percent of the total weight of the block copolymer. The organic solution may include a diblock copolymer and at least one polymer block of poly(ε-caprolactone) with a number-average molecular weight that is from about 9 kiloDalton to about 23 kiloDalton. The organic solution may include a diblock copolymer and at least one polymer block comprising poly(ε-caprolactone) with a number-average molecular weight that is from about 9.5 kiloDalton to about 22.2 kiloDalton. The organic solution may include a diblock copolymer and at least one polymer block comprising poly(γ-methyl ε-caprolactone) with a-number average molecular weight that is from about 4 kiloDalton to about 10 kiloDalton. The organic solution may include a diblock copolymer and at least one polymer block comprising poly(γ-methyl ε-caprolactone) with a-number average molecular weight that is from about 4.8 kiloDalton to 9.5 kiloDalton. The organic solution may include a diblock copolymer comprising poly(ethylene oxide) and poly(ε-caprolactone). The poly(ethylene oxide) may have a number-average molecular weight that is about 2 kiloDalton and the poly(ε-caprolactone) may have a number-average molecular weight that is about 12 kiloDalton. The poly(ethylene oxide) may have a number-average molecular weight that is between about 1.8 kiloDalton and about 1.9 kiloDalton and the poly (ε-caprolactone) may have a number-average molecular weight that is between about 8 kiloDalton and about 9.5 kiloDalton.

In various embodiments, the method of manufacturing a composition may includes rehydrating the dried oxygen carrier in an aqueous solution having a pharmaceutically acceptable salt and/or administering the oxygen carrier to a subject in need thereof. The oxygen carrier may be administered intravenously, via inhalation, topically, per rectum, per the vagina, transdermally, subcutaneously, intraperitoneally, intrathecally, intramuscularly, or orally.

Various embodiments provide a method of treating a subject. An oxygen carrier composition comprising a plurality of polymers and an oxygen-binding compound may be administrated to the subject. The oxygen carrier may administered intravenously, via inhalation, topically, per rectum, per the vagina, transdermally, subcutaneously, intraperitoneally, intrathecally, intramuscularly, or orally.

Various embodiments provide a kit that includes a pharmaceutical composition comprising an oxygen carrier. The oxygen carrier may include a plurality of polymers and an oxygen-binding compound. The kit may include an implement for administering the oxygen carrier intravenously, via inhalation, topically, per rectum, per the vagina, transdermally, subcutaneously, intraperitoneally, intrathecally, intramuscularly, or orally.

Various embodiments provide a kit that includes a first container and a second container. The first container may include an oxygen carrier. The second container may include a rehydration mixture. The oxygen carrier may be lyophilized or dried.

Various embodiments provide a pharmaceutical composition including the above-mentioned oxygen carriers and/or polymersomes. The pharmaceutical composition may include pharmaceutically active agent in an effective amount to treat or prevent a disease or disorder in a subject. The pharmaceutical composition may include any of the above-mentioned compositions, oxygen carriers and/or polymersomes for treatment or prevention of reduced tissue oxygenation in an effective amount for a subject in need thereof. The pharmaceutical composition may include any of the above-mentioned compositions, oxygen carriers and/or polymersomes for increasing the rate of wound healing in an effective amount for a subject in need thereof. The pharmaceutical composition may include any of the above-mentioned compositions, oxygen carriers and/or polymersomes for treatment or prevention of an immunologic, rheumatologic, oncologic or inflammatory condition in an effective amount for a subject in need thereof. The pharmaceutical composition may include any of the above-mentioned compositions, oxygen carriers and/or polymersomes for treatment or prevention of cellular dysplasia, hyperplasia, malignant cancer, or tumor growth in an effective amount for a subject in need thereof.

Various embodiments provide a method of releasing a pharmaceutically active agent from within the oxygen-carrier and/or polymersomes. A polymersome and/or oxygen carrier may be exposed to a physiological stimulus or a stimulus equivalent to a physiological condition in a subject. The stimulus may be an acidic environment, an osmotic gradient, oxidative or reductive stress, or heat.

Various embodiments provide a method for treating to preventing benign or malignant tumor growth in a subject in need thereof by administering the oxygen carrier and/or polymersomes.

Various embodiments provide a method of treating or preventing low oxygenation of tissues in a subject in need thereof bye administering the oxygen carrier and/or polymersomes.

Various embodiments provide a method of stimulating wound healing tissues in a subject in need thereof by administering the oxygen carrier and/or polymersomes to a subject in need thereof.

BRIEF DESCRIPTION OF THE DRAWINGS

The accompanying drawings, which are incorporated herein and constitute part of this specification, illustrate example aspects of the invention, and together with the general description given above and the detailed description given below, serve to explain the features of the invention.

DETAILED DESCRIPTION OF THE INVENTION

Figure 1:
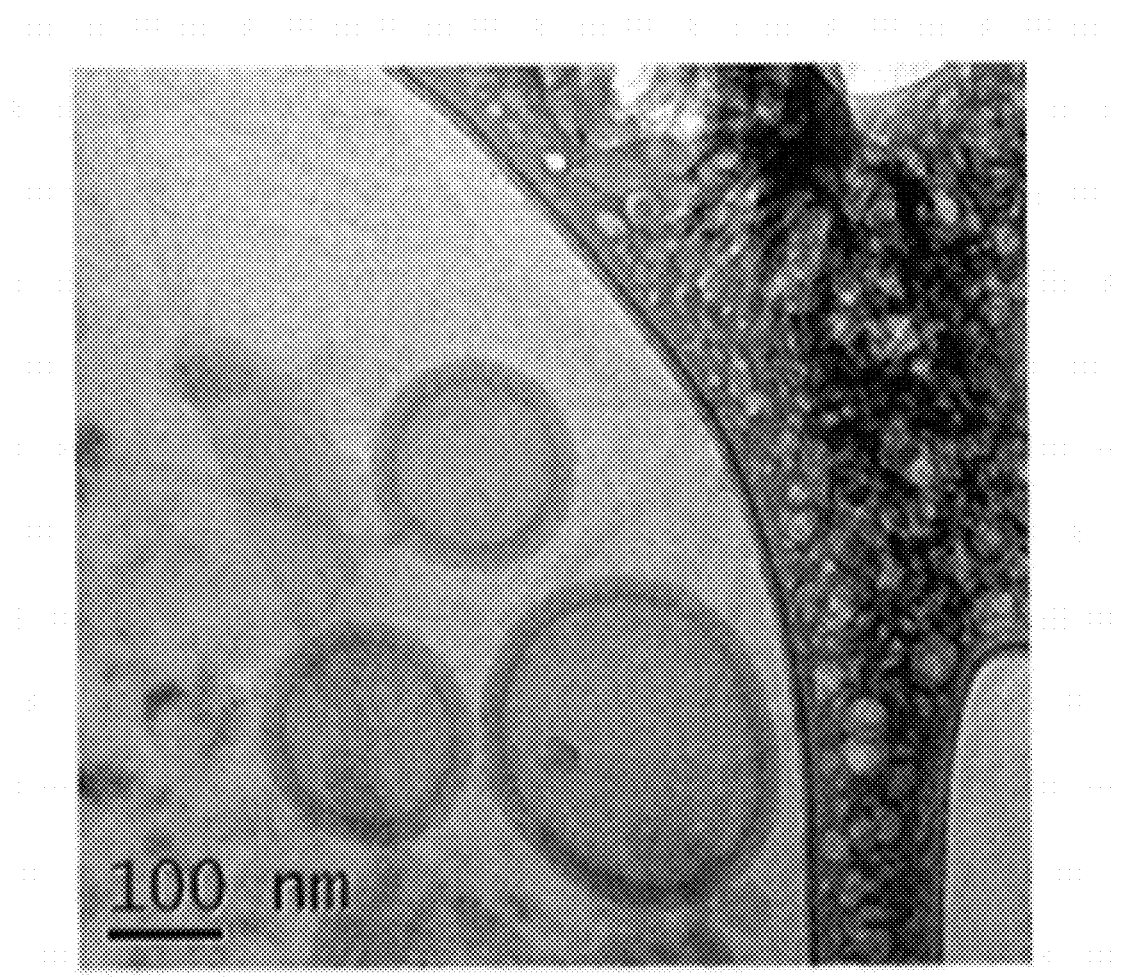
FIG. 1 is a cryogenic transmission electron micrograph of PEO(2K)-b-PCL(12K)-based polymersomes in de-ionized water (5 mg/ml) that illustrates the membrane core thickness of the vesicles as being 22.5±2.3 nanometer.

The present invention may be understood more readily by reference to the following detailed description taken in connection with the accompanying figures and examples, which form a part of this disclosure. It is to be understood that the various embodiments are not limited to the specific devices, methods, applications, conditions or parameters described and/or shown herein, and that the terminology used herein is for the purpose of describing particular embodiments by way of example only and is not intended to be limiting.

It is to be appreciated that certain features that are, for clarity, described herein in the context of separate embodiments, may also be provided in combination in a single embodiment. Conversely, various features that are, for brevity, described in the context of a single embodiment, may also be provided separately or in any sub-combination. Further, reference to values stated in ranges include each and every value within that range.

As used in this specification and the appended claims, the singular forms "a," "an," and "the" include plural referents unless the content clearly dictates otherwise.

The word "about" is used herein when referring to a measurable value such as an amount, a temporal duration, and the like, and is meant to encompass variations of ±20%, ±10%, ±5%, ±1%, or ±0.1% from the specified value, as such variations are appropriate to perform the disclosed methods.

When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

The word "plurality" is used herein to mean more than one.

The terms "subject" and "patient" are used interchangeably herein to refer to human patients, whereas the term "subject" may also refer to any animal. It should be understood that in various embodiments, the subject may be a mammal, a non-human animal, a canine and/or a vertebrate.

The term "monomeric units" is used herein to mean a unit of polymer molecule containing the same or similar number of atoms as one of the monomers. Monomeric units, as used in this specification, may be of a single type (homogeneous) or a variety of types (heterogeneous).

The term "polymers" is used according to its ordinary meaning of macromolecules comprising connected monomeric molecules. Polymers of the invention may comprise any number of combinations of different hydrophilic and hydrophobic blocks. In some embodiments, the hydrophilic and hydrophobic blocks are chosen from at least one of the following: hydrophilic biocompatible poly(ethylene oxide) (PEO) coupled to various hydrophobic aliphatic poly(anhydrides), poly(nucleic acids), poly(esters), poly(ortho esters), poly(peptides), poly(phosphazenes) and poly(saccharides), including but not limited by poly(lactide) (PLA), poly(glycolide) (PLGA), poly(lactic-co-glycolic acid) (PLGA), poly (ε-caprolactone) (PCL), and poly(trimethylene carbonate) (PTMC).

The term "amphiphilic substance" is used herein to mean a substance containing both polar (water-soluble) and hydrophobic (water-insoluble) groups.

The term "in vivo delivery" is used herein to refer to delivery of a biologic by routes of administration such as topical, transdermal, suppository (rectal, vaginal), pessary (vaginal), intravenous, oral, subcutaneous, intraperitoneal, intrathecal, intramuscular, intracranial, inhalational, oral, and the like.

The term "an effective amount" is used herein to refer to an amount of a compound, material, or composition effective to achieve a particular biological result such as, but not limited to, biological results disclosed, described, or exemplified herein. Such results may include, but are not limited to, the effective reduction of symptoms associated with any of the disease states mentioned herein, as determined by any means suitable in the art.

The term "membrane" is used herein to mean a spatially distinct collection of molecules that defines a 2-dimensional surface in 3-dimensional space, and thus separates one space from another in at least a local sense.

The term "pharmaceutically active agent" is used herein to refer to any a protein, peptide, sugar, saccharide, nucleoside, inorganic compound, lipid, nucleic acid, small synthetic chemical compound, or organic compound that appreciably alters or affects the biological system to which it is introduced.

The term "drug delivery" is used herein to a method or process of administering a pharmaceutical compound to achieve a therapeutic effect in humans or animals.

The term, "delivery vehicles" is used herein to refer to agents with no inherent therapeutic benefit but when combined with an agent for the purposes of drug delivery result in modification of the pharmaceutical compounds solution concentration, bioavailability, absorption, distribution and elimination for the benefit of improving product efficacy and safety, as well as patient convenience and compliance.

The term "carrier" is used herein to refer to describe the use of a delivery vehicle to incorporate a pharmaceutically active agent for the purposes of drug delivery.

The term "oxygen-binding compound" is used herein to refer to refer to any molecule or macromolecule that associates with oxygen.

The term "oxygen carrier" is used herein to refer to a synthetic or partially synthetic drug delivery vehicle or set of macromolecules comprising oxygen or having a high affinity for oxygen, an example of which is hemoglobin.

The term "allosteric effector" is used herein to refer to a molecule that modulates the rate or amount of oxygen binding to or releasing from of an oxygen carrier.

The term "homopolymer" is used herein to refer to a polymer derived from one monomeric species of polymer.

The term "copolymer" is used herein to refer to a polymer derived from two (or more) monomeric species of polymer, as opposed to a homopolymer where only one monomer is used. Since a copolymer includes at least two types of constituent units (also structural units), copolymers may be classified based on how these units are arranged along the chain.

The term "block copolymers" is used herein to refer to a copolymer that comprises two or more homopolymer subunits linked by covalent bonds in which the union of the homopolymer subunits may require an intermediate non-repeating subunit, known as a junction block. Block copolymers with two or three distinct blocks are referred to herein as "diblock copolymers" and "triblock copolymers," respectively.

The term "areal strain" is used herein to refer to the change in the surface area of a particle under an external force or tension divided by the original surface area of the particle prior to application of said external force or tension (denoted by "A" and expressed as %).

The term "critical lysis tension" or "Tc" is used herein to refer to the tension at which a particle ruptures when subject to an external force as measured by micropipette aspiration and expressed as milliNewtons/meter (mN/m).

The term "critical areal strain" or "Ac" is used herein to refer to the areal strain realized by the oxygen carrier or polymersome at the critical lysis tension.

The term "hemoglobin loading capacity" is used herein to refer to a measurement of a hemoglobin-based oxygen carrier and may be defined as the weight of hemoglobin within the oxygen carrier divided by the total weight of carrier. The term "hemoglobin loading efficiency" is used herein to refer to a measurement of a hemoglobin-based oxygen carrier and may be defined as the weight of hemoglobin that is encapsulated and/or incorporated within a carrier suspension divided by the weight of the original hemoglobin in solution prior to encapsulation (expressed as a %).

The term a "unit dose" is used herein to refer to a discrete amount of the pharmaceutical composition comprising a predetermined amount of the active ingredient.

The term "vesicle" is used herein to refer to a fluid filled sac. In some embodiments the vesicle is a sac comprising an amphiphillic substance. In some embodiments, the sac is a nanoparticle-based vesicle, which refers to a vesicle with a size or dimensions in the nanometer range. In some embodiments, a polymer vesicle is a vesicle that is manufactured with one or more polymers.

As mentioned above, the collection and storage of donated red blood cells for transfusion is a difficult and expensive task. Artificial blood substitutes are a potential alternative to donor blood and provide several advantages over human donor blood. For example, artificial blood substitutes may be: designed to be free of human red blood cell antigens (i.e., can be administered to individuals possessing any blood group type);[3] readily mass-produced with guaranteed sterility (eliminating the possibility of infectious transmittal or the need for infectious blood screening);[4] designed to have longer storage lifetimes and require less stringent storage conditions than donor blood;[3, 5] and produced at lower costs (e.g., by avoiding the screening and storage costs currently associated with human donor blood units).[3, 5, 6]

The various embodiments provide compositions and methods for developing oxygen carriers which may be used, for example, as artificial blood substitutes that may include hemoglobin, myoglobin, or other oxygen binding compounds.

In order to be an adequate replacement for donor blood, an ideal artificial blood substitute should replicate blood's ability to transport oxygen to tissues. For example, an ideal artificial blood substitute should be an oxygen therapeutic. An ideal synthetic oxygen therapeutic (i.e., oxygen-carrying artificial blood substitutes) should have normal physiological oxygen-binding properties, be uniform and small size so as to both afford long circulation lifetimes and safe clearance from body, have human bloodlike viscosity and oncotic pressure characteristics so as to preserve shear forces in the microcirculation and enable plasma expansion in the resuscitation of patients, have tunable oxygen release parameters for tissues experiencing normal or low oxygenation, and be free of infectious disease risks associated with intravenous administration.

Various embodiments provide an oxygen-carrying artificial blood substitute that has normal physiological oxygen-binding properties, is uniform and small size, has human bloodlike viscosity and oncotic pressure characteristics, has tunable oxygen release parameters, and is resistant to infectious diseases.

Heretofore, oxygen therapeutics have been based on two types of molecules capable of transporting oxygen: perfluorocarbons (PFCs) and hemoglobin (Hb). Perfluorocarbons are synthetic, inert fluorinated hydrocarbons capable of storing large amounts of dissolved oxygen.[7, 8] However, due to the linear relationship between the amount of oxygen dissolved in the fluid phase of perfluorocarbons dispersions, and the partial pressure of oxygen (pO2) in solution, high concentrations of dissolved oxygen are available for diffusion only at high pO2s.[8] Moreover, perfluorocarbons are immiscible in water and need to be emulsified before being administered to patients.[7, 8]

A number of PFC-based oxygen therapeutics have been attempted and/or are known. Fluosol DA (Green Cross Corporation, Japan) was a first generation commercially available PFC preparation aimed at elucidating blood flow mechanisms for angioplasty.[9, 10] It was removed from the market in 1994 due to adverse physiological reactions encountered by patients during clinical trials. Second generation PFC products include Oxyfluor™ (HemaGen/PFC, USA), Oxygent™ (Alliance Pharmaceutical Corporation, USA), and Perftoran™ (SPC-Perftoran, Russia). The development of Oxyfluor™ was terminated after phase I clinical trials due to several side effects that limited its potential administered dose.[11] Oxygent™ was associated with an increased incidence of stroke in coronary bypass patients and its clinical trials were terminated.[12] Perftoran™ has been approved for human use only in Russia since 1999 and in Mexico since 2005.[13] Other PFC products in development include Pher-O2™ (Sanguine Corp., USA) and Oxycyte™ (Synthetic Blood International, USA).[14]

As an alternative to perfluorocarbons, artificial blood substitutes may utilize hemoglobin (Hb) for safe and effective oxygen delivery. Hemoglobin is an oxygen-transporting protein in human red blood cells. Hemoglobin can be obtained with commercial grade purity from both human and animal sources, and methods to extract hemoglobin from human as well as bovine red blood cells (as a convenient and compatible replacement to human hemoglobin) have been previously developed and optimized, and are known in the art. For example, a rigorous, multi-level filtration set-up consisting of glass wool filtration followed by passage through a four-stage hollow fiber apparatus has been utilized to purify and concentrate extracted hemoglobin. The purity of both bovine and human hemoglobin derived from this set-up has been shown, through sodium dodecyl sulfate polyacrylamide gel (SDS-PAGE) electrophoresis, to be greater than 96%, with methemoglobin (metHb) levels of these hemoglobin solutions always being below 3%. The availability of hemoglobin makes it an attractive oxygen carrying protein for use in the artificial blood substitute of the various embodiments. In some embodiments, purification of hemoglobin is performed by the methods described in Elmer, et al., *Journal of Chromotography B*, 879, (2011); 131-138, which is herein incorporated by reference in its entirety. In some embodiments, purification of hemoglobin is performed by the methods described in Elmer, et al., *Biotechnology and Bioengineering*, (106), May 1, 2010, which is herein incorporated by reference in its entirety. In some embodiments, purification of hemoglobin is performed by the methods described in Buehler, et al., *Biomaterials*, 37 (2010); 3723-3735, which is herein incorporated by reference in its entirety.

Hemoglobin consists of two pairs of globin dimers held together by non-covalent bonds to form a larger four subunit (tetrameric) hemoglobin molecule. The oxygen binding capacity of tetrameric hemoglobin depends on the presence of a non-protein unit called the heme group (i.e., one molecule of hemoglobin can bind with four oxygen molecules). The co-operative binding of oxygen to hemoglobin gives native hemoglobin its characteristic sigmoidal-shaped oxygen dissociation curve and allows oxygen to be bound and released within a narrow physiological range of pO2s (from 40-100 mmHg). This results in approximately 70% increase in oxygen delivery in an active capillary bed compared to the non-cooperative oxygen binding of perfluorocarbons at a given oxygen partial pressure.

While the hemoglobin-based oxygen therapeutics have numerous advantageous over the perfluorocarbons-based oxygen therapeutics, initial studies involving the infusion of cell-free hemoglobin into animals, showed that free hemoglobin results in significant vasoconstriction and kidney damage.[15, 16] Consequently, hemoglobin-based oxygen carriers (HBOCs) require stabilizing the hemoglobin molecule in order to eliminate adverse physiological effects while maintaining the physiological oxygen-transporting ability of native cell-free hemoglobin. The various embodiments provide an oxygen carrier that maintains the physiological oxygen-transporting abilities of native cell-free hemoglobin while avoiding the adverse physiological effects associated with hemoglobin.

Hemoglobin-based oxygen carriers (HBOCs) may be either acellular or cellular oxygen carriers. Acellular HBOCs may be prepared by molecular modification of tetrameric hemoglobin and can be characterized as either "polymeric", "cross-linked" or "recombinant" hemoglobin. Polymeric hemoglobin may be synthesized by intra- and inter-molecular cross-linking of tetrameric hemoglobin; while solely intra-molecular cross-linking of tetrameric hemoglobin produces cross-linked hemoglobin. Recombinant hemoglobin may be synthesized by fusing the two α-subunits of hemoglobin to prevent dissociation of the resulting tetramer into dimers. Tetrameric hemoglobins have further been conjugated with bioinert, water-soluble polymers to form conjugated hemoglobins.

Acellular HBOCs may induce vasoconstriction when transfused into animals due to nitric oxide (NO) sequestration and/or an over-oxygenation auto-regulatory response.[11, 17] Moreover, acellular HBOCs generally demonstrate limited circulatory half-lives (usually less than 12 hours) and are only suitable for short-term applications.[18, 19] Also, acellular Hbs do not deliver oxygen as efficiently as cellular Hbs, may be rapidly converted to an inactive form called methemoglobin (metHb), and can cause an immune reaction if it is not prepared from human blood components.[17, 19]

Several commercial acellular HBOCs are currently in development and are in various stages of clinical trials. For example, Hemopure™ (Biopure Corp., Cambridge, Mass., USA) was approved for clinical use in South Africa and was recently in phase III clinical trials in the US. Biopure Corporation, however, recently underwent liquidation bankruptcy so Hemopure's regulatory status is now uncertain. Poly-Heme™ (Northfield Lab, Evanston, Ill., USA) completed phase III clinical trials but recently failed to win FDA approval. It, like all acellular HBOCs, was observed to induce vasoconstriction when transfused into animals, presumably due to nitric oxide (NO) sequestration and/or an over-oxygenation auto-regulatory response.[11, 17]

Various embodiments circumvent the limitations associated with acellular HBOCs by providing compositions that include oxygen carriers having an oxygen-binding compound encapsulated in a polymer vesicle. In various embodiments, the cellular-based oxygen carrier may encapsulate hemoglobin as the oxygen-binding compound.

Cellular-based HBOCs are artificial hemoglobin-based blood substitutes that encapsulate free hemoglobin molecules inside the aqueous core of semi-permeable membrane shells. The structure of these oxygen carriers may be similar to natural human red blood cells. The membranes of cellular HBOCs protect surrounding tissues and blood components from direct contact with potentially toxic tetrameric hemoglobin. Encapsulation of hemoglobin inside these membrane carriers permits manipulation of the physiochemical properties and circulation lifetimes of cellular based HBOCs.[16] Semi-permeable membranes reduce recognition of encapsulated hemoglobin by the reticuloendothelial system (mononuclear phagocyte system), therefore prolonging the intravascular lifetime of the artificial blood substitute.[16] Surface modification of cellular HBOC membranes can further improve the intravascular persistence and colloidal state of these oxygen carriers.[20, 21] Catalases, reductants, and reductases can be readily coencapsulated with hemoglobin in cellular HBOCs in order to suppress metHb formation, which has notably limited the safety and efficacy of their acellular Hb-based counterparts.[22-24] In the embodiments, hemoglobin is shielded from the immune system within cellular HBOCs, so less expensive animal hemoglobin can potentially be incorporated in HBOCs and used to create safe and effective human clinical blood substitutes.

As mentioned above, the various embodiments circumvent the limitations associated with acellular HBOCs by providing compositions that include oxygen carriers having an oxygen-binding compound encapsulated in a polymer vesicle. In various embodiments, the oxygen carriers may include polymersome. In various embodiments, the oxygen carriers may be a polymersome. In some embodiments, the oxygen carriers or polymersomes may comprise a mixture of oxygen-binding compounds. In various embodiments, the oxygen-binding compound may be hemoglobin. In various embodiments, the oxygen-binding compound may be a chemical synthesized by an animal, a recombinant polypeptide, a synthetic small molecule, a carbohydrate, a nucleic acid or a lipid. In various embodiments, the oxygen-binding compound may be a naturally occurring protein, a recombinant protein, a recombinant polypeptide, a synthetic polypeptide or a polymer. In various embodiments, the oxygen-binding compound may be a compound derived from a naturally occurring protein, a recombinant protein, a recombinant polypeptide, a synthetic polypeptide, a polymer, or any combination thereof.

Since many of the limitations associated with acellular HBOCs may be circumvented by encapsulating hemoglobin in an appropriate carrier, several attempts have been made to encapsulate hemoglobin inside liposomes (self-assembled vesicles made from natural phospholipids).[25-28] It has been demonstrated that liposome-encapsulated hemoglobin (LEH) dispersions exhibit low permeability to polar molecules, are deformable, and can thus easily permeate through capillary blockages; they were thus postulated as potential oxygen carriers in cases of trauma and routine surgery.[29] However, the circulatory half-life of unmodified LEHs is very short (i.e., approximately between 4 and 12 hrs), which has hindered their clinical development.[30, 31] LEH particles are further prone to aggregate and fuse together after several days of in situ storage, diminishing their functionality.[29] The most promising strategy to circumvent these significant limitations relies on the surface modification of LEH particles with polyethylene glycol.[27, 32]

Polyethylene glycol (PEG) is a Food and Drug Administration (FDA) approved biologically inert polymer. PEG's conjugation with liposome-encapsulated hemoglobin (LED) particles has been observed to increase their intravascular persistence, stability, rheology, hemodynamic properties and biocompatibility.[29, 33, 34] However, the shielding effect imparted by PEG is limited by the maximum amount of PEGylated lipids that can be incorporated into the liposome bilayer before phase separation occurs.[35] Maximal LEH surface modification with PEG has been reported to be ~10 mol % (seen by utilizing 5 kDa PEGylated lipids),[36] with the PEG-LEH dispersions exhibiting a circulation half-life (t½) of 24-48 hours in rabbits and 36 hours in rats.[37] Also, the maximum surface concentration of PEG that can be conjugated onto liposome bilayers decreases with increasing PEG molecular weight due to the increasing hydrophilicity of the PEG-lipid. Therefore, there is a physical limit when optimizing the steric shielding, stability and biocompatibility of PEG-LEH dispersions. Additionally, utilizing PEG of <5 kDa molecular weight for LEH conjugation may not effectively prevent complement activation in vivo.[37] Thus, while there are some potential advantages to PEG-LEH-based dispersions, there are also many limitations.

The various embodiments provide an alternative cellular oxygen carrier that builds on the above-mentioned advantages while circumventing the limitations seen with the first generation PEG-LEH dispersions. The various embodiments provide an alternative cellular hemoglobin-based oxygen carrier that may be used to decrease dependence on human red blood cell transfusions. The various embodiments provide compositions of matter and methods to develop an advanced, slowly biodegradable, hemoglobin-based oxygen carrier that utilizes a nanoparticle-based delivery vehicle. Various embodiments leverage polymer vesicles (such as polymersomes) for the encapsulation of the hemoglobin in order to minimize hemoglobin toxicity and degradation by shielding the proteins within nanoparticles. Encapsulation of hemoglobin in polymer vesicles and/or nanoparticle shells protects the hemoglobin from contact with blood and tissues.

Polymersomes[38, 39] are synthetic polymer vesicles that are formed in nanometric dimensions (50 to 300 nm) and exhibit several favorable properties as cellular oxygen carriers. For example, polymersomes belong to the class of bi-layered vesicles that can be generated through self-assembly; can encapsulate hydrophilic compounds such as hemoglobin in their aqueous core;[40, 41] offer several options to be designed from fully biodegradable FDA-approved components; and exhibit no in vitro or acute in vivo toxicities. Polymersomes also exhibit several properties that are superior to liposomes and other nanoparticle-based delivery vehicles that make them effective hemoglobin-based oxygen carriers (HBOCs). For example, depending on the structure of their component copolymer blocks, polymersome membranes may be significantly thicker (~9-22 nm) than those of liposomes (3-4 nm), making them 5-50 times mechanically tougher and at least 10 times less permeable to water than liposomes.[46, 47] The circulatory half-life of polymersomes, with poly(ethylene oxide) (herein "PEO") brushes ranging from 1.2-3.7 kDa, is analogous to that of poly(ethylene glycol)-liposomes (herein "PEG-liposome") of similar sizes (~24-48 hours), and can be specifically tailored by using a variety of copolymers as composite building blocks.[48] Polymersomes have been shown to be stable for several months in situ (and for several days in blood plasma under well-mixed quasi-physiological conditions) without experiencing any changes in vesicle size and morphology.[40, 48] Polymersomes do not show in-surface thermal transitions up to 60° C.[37, 48] Early animal studies on poly(ethylene oxide)-block-poly(ε-caprolactone) (herein "PEO-b-PCL") and poly(ethylene-oxide)-block-poly(butadiene) (herein "PEO-b-PBD") based polymersomes formulations encapsulating doxorubicin have shown no acute or sub-acute toxicities. The production and storage of polymersomes is economical, as polymersomes may be readily produced and stored on a large-scale without requiring costly post-manufacturing purification processes.

The most promising biodegradable polymersome-encapsulated hemoglobin (PEH) formulations are comprised of block copolymers made of the hydrophilic biocompatible poly(ethylene oxide) (herein "PEO") coupled to various hydrophobic aliphatic poly(anhydrides), poly(nucleic acids), poly(esters), poly(ortho esters), poly(peptides), poly(phosphazenes) and poly(saccharides), including but not limited by poly(lactide) (herein "PLA"), poly(glycolide) (herein "PGA"), poly(lactic-co-glycolic acid) (herein "PLGA"), poly(ε-caprolactone) (herein "PCL"), and poly(trimethylene carbonate) (herein "PTMC"). Polymersomes comprised of 100% PEGylated surfaces have been shown to possess improved in vitro chemical stability, augmented in vivo bioavailability and prolonged blood circulatory half-lives.[42, 43] For example, aliphatic polyesters, constituting the polymersomes' membrane portions, are degraded by hydrolysis of their ester linkages in physiological conditions such as in the human body. Because of their biodegradable nature, aliphatic polyesters may be used as implantable biomaterials in drug delivery devices, bioresorbable sutures, adhesion barriers and as scaffolds for injury repair via tissue engineering.[44, 45]

The various embodiments provide compositions of matter and methods for making, storing and administering oxygen carriers that include biodegradable aliphatic polyesters. In various embodiments, the biodegradable aliphatic polyesters is poly(ε-caprolactone) or "PCL". In various embodiments, the biodegradable aliphatic polyesters is poly(γ-methyl ε-caprolactone). In various embodiments, the oxygen carriers utilize poly(ε-caprolactone) as a membrane-forming shell. In various embodiments, the oxygen carriers utilize poly(ε-caprolactone) and/or poly(γ-methyl ε-caprolactone) as a membrane-forming shell.

Compared to the other biodegradable aliphatic polyesters, PCL has several advantageous properties including: high permeability to small drug molecules; maintenance of a neutral pH environment upon degradation; facility in forming blends with other polymers; and suitability for long-term delivery afforded by slow erosion kinetics as compared to PLA, PGA, and PLGA.[45] Utilization of ε-caprolactone (or derivatives such as γ-methyl ε-caprolactone) as the membrane-forming shells in polymersome-encapsulated hemoglobin (PEH) formulations allows the resultant cellular hemoglobin-based oxygen carriers (HBOCs) to have safe and complete in vivo degradation.

In various embodiments, the oxygen carriers and/or polymersomes may be made from poly(ethylene oxide)-block-poly(ε-caprolactone) (PEO-b-PCL) and related diblock copolymers of poly(ethylene oxide)-block-poly(γ-methyl ε-caprolactone) (PEO-b-PMCL). PEO provides the oxygen carriers and/or polymersomes improved in vitro chemical stability, augmented in vivo bioavailability and prolonged blood circulation half-lives. Both PEO-b-PCL and PEO-b-PMCL may afford complete and safe in vivo biodegradation of polymersome membranes via hydrolysis of their ester linkages. In various embodiments, PEO-b-PCL and PEO-b-PMCL polymersomes may be cellular hemoglobin-based oxygen carriers (HBOCs) as they possess all the requisite properties for effective oxygen delivery, including tunable oxygen-binding capacities, uniform and appropriately small size distributions, human bloodlike viscosities and oncotic properties, as well as ease of mass production and affordable storage.

Previously, poly(ethylene oxide)-block-poly(ε-caprolactone) (herein "PEO-b-PCL")-based PEH dispersions have not demonstrated the requisite properties for further development as cellular HBOCs. Their observed hemoglobin encapsulation efficiencies were shown to be quite low, predominantly because the specific PEO-b-PCL formulations may not generate a high yield of vesicles in solution. However, fully biodegradable and bioresorbable polymersomes have been demonstrated to be generated via self-assembly upon aqueous hydration of amphiphilic diblock copolymers of PEO-b-PCL.[39] Over 20 PEO-b-PCL copolymers, varying in molecular weights of the component building blocks, have been tested for the generation of stable bilayered polymersomes. FIG. 1 illustrates that only diblock copolymers of PEO-b-PCL in which the PEO block was X-X kDa and Y-Y % of the polymer mass by weight have demonstrated a consistent and significant yield of stable mono-dispersed polymersomes, with mean particle diameters of <200 nm and membrane thicknesses of 9-22 nm after extrusion through 200-nm pore-cutoff membranes. PEO-b-PCL polymersomes have subsequently been shown to be capable of loading the anti-neoplastic drug doxorubicin (DOX) using an ammonium sulfate gradient.

Figure 2:
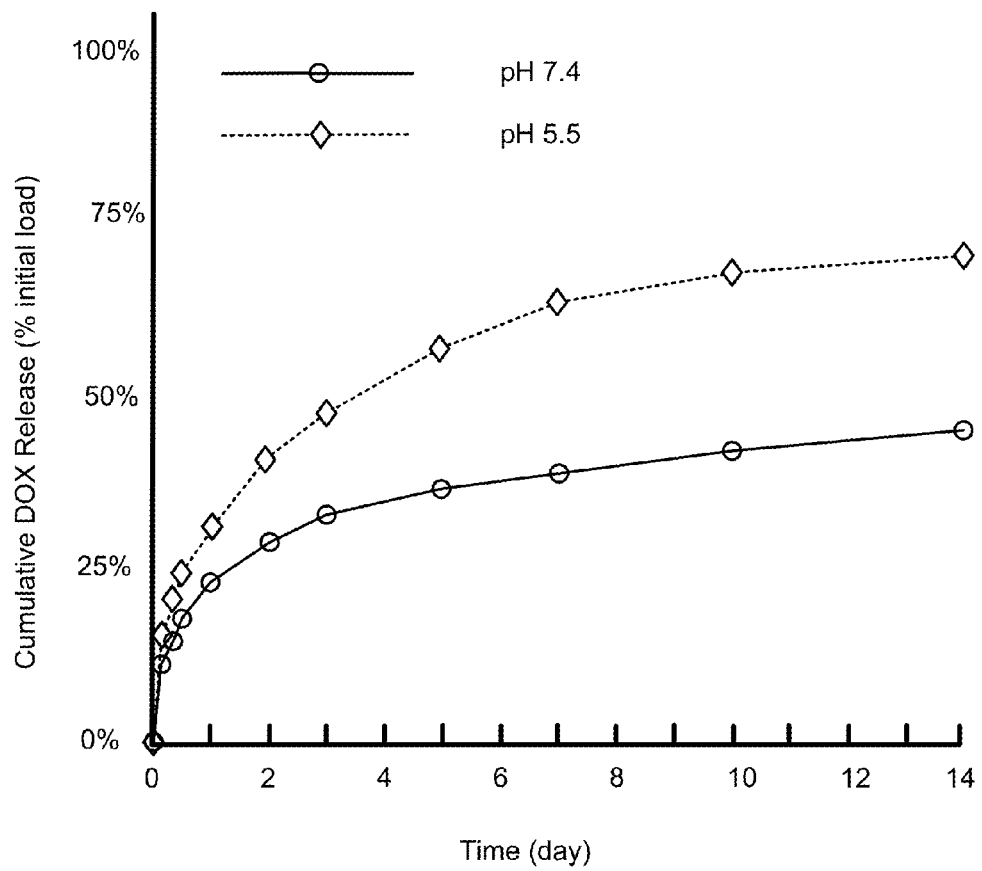
FIG. 2 is a line chart illustrating the cumulative in situ release of doxorubicin, loaded within 200 nm diameter PEO (2K)-b-PCL(12K) based polymersomes, under various physiological conditions (pH 5.5 and 7.4; T=37° C.) as measured fluorometrically over 14 days.

FIG. 2 illustrates the in vitro stability, mechanism of degradation and rate of drug release from DOX-loaded PEO(2 kDa)-b-PCL(12 kDa) polymersomes evaluated as a function of pH over 14 days. FIG. 2 shows that, while the kinetics of release varied under neutral and acidic pH conditions (5.5 and 7.4, at 37° C.), an initial burst release phase (approx. 20% of the initial payload within the first 8 h) was observed at both pH conditions followed by a more controlled, pH-dependent release over the several days. At a pH of 7.4, kinetic release studies show that the encapsulated molecules initially escape the polymersome through passive diffusion of the drug across the intact PCL membrane (days 1-4), and subsequently through hydrolytic matrix degradation of PCL (days 5-14). At a pH of 5.5, however, the dominant mechanism of release, at both short and long times, is acid-catalyzed hydrolysis of the PCL membrane. Notably, these fully-biodegradable polymersomes have a t½ half-life of circulation (24-48 h) that is much shorter than their t½ half-life of release (2 weeks at pH 7.4).

As discussed above, polymers are macromolecules comprising connected monomeric heterogeneous molecules, with the monomeric units being either of a single type (homogeneous) or of a variety of types (heterogeneous). The physical behavior of polymers may be dictated by several factors, including: the total molecular weight; the composition of the polymer (e.g., the relative concentrations of different monomers); the chemical identity of each monomeric unit and its interaction with a solvent; and the architecture of the polymer (e.g., whether it is single chain or branched chains). For example, in PEG, which is a polymer of ethylene oxide (EO), the chain lengths of which, when covalently attached to a phospholipid, optimize the circulation life of a liposome, is known to be in the approximate range of 34-114 covalently linked monomers (EO34 to EO114). In some embodiments, the copolymers comprise a hydrophilic PEO (polyethylene oxide) block and one of several hydrophobic blocks that drive self-assembly of the polymersomes, up to microns in diameter, in water and other aqueous media.

As discussed above, an amphiphilic substance is one containing both polar (water-soluble) and hydrophobic (water-insoluble) groups. To form a stable membrane in water, a potential minimum requisite molecular weight for an amphiphile must exceed that of methanol HOCH3, which is the smallest canonical amphiphile, with one end polar (HO—) and the other end hydrophobic (—CH3). Formation of a stable lamellar phase requires an amphiphile with a hydrophilic group whose projected area is approximately equal to the volume divided by the maximum dimension of the hydrophobic portion of the amphiphile.

In various embodiments, the oxygen carrier, nanoparticle and/or polymersome does not include polyethylene glycol (PEG) as one of its plurality of polymers. In various embodiments, the oxygen carrier, nanoparticle and/or polymersome include least one hydrophilic polymer that is polyethylene glycol (PEG). In various embodiments, the polyethylene glycol (PEG) polymer may vary in molecular weight from about 5 kiloDaltons (kDa) to about 50 kDa in molecular weight.

As mentioned above, the various embodiments provide compositions and methods for developing artificial blood substitutes that may include hemoglobin, myoglobin, or other oxygen binding compounds. The oxygen carriers of the various embodiments may include polymersomes comprising of poly(ethylene oxide)-block-poly(ε-caprolactone) (PEOb-PCL) and related diblock copolymers of poly(ethylene oxide)-block-poly(γ-methyl ε-caprolactone) (PEO-b-PMCL). PEO provides the polymersomes improved in vitro chemical stability, augmented in vivo bioavailability and prolonged blood circulation half-lives. Both PEO-b-PCL and PEO-b-PMCL afford complete and safe in vivo biodegradation of polymersome membranes via hydrolysis of their ester linkages. In an embodiment, the composition may include PEO-b-PCL and PEO-b-PMCL polymersomes having the above-mentioned requisite properties for effective oxygen delivery, including tunable oxygen-binding capacities, uniform and appropriately small size distributions, human bloodlike viscosities and oncotic properties, as well as ease of mass production and affordable storage.

The various embodiments incorporate hemoglobin into a biodegradable polymeric carrier (such as the polymersome) providing a cellular hemoglobin-based oxygen carrier (cellular HBOC) formulation that has the requisite properties to serve as a synthetic blood substitute. In various embodiments, polymersome-encapsulated hemoglobin (PEH) dispersions are used, which exhibit several advantages over other HBOCs. In various embodiments, the biodegradable polymersome-encapsulated hemoglobin (PEH) dispersions may be comprised of diblock copolymers of PEO-b-PCL with a PEO block size from about 1.5 kiloDaltons to about 2 kiloDaltons and with a block fraction of ~10-15% by weight. In other embodiments, the PEH dispersions may be comprised of diblock copolymers of PEO-b-PMCL.

The various embodiments provide methods of synthesizing PEH dispersions that consistently meet the following standard characteristics: average radius between 100-125 nm with polydispersity index<1.1; Hb encapsulation efficiency>50%; weight ratio of Hb:polymer in PEH dispersions>2; metHb level<5%; and viscosity between 3-4 cP. The various embodiments further encompass PEH constructs that meet the following characteristics: tunable P50 between 20-50 mm Hg; co-operativity coefficient>2; at least an order of magnitude smaller NO binding rate constant than that measured for liposome-encapsulated hemoglobin dispersions (LEHs) at similar Hb loading concentrations; excellent stability under different storage and flow conditions as determined by intact morphology, change in average particle diameter<5 nm and unaltered Hb concentration (change<0.5 g/dL) and unchanged metHb level (change<2%).

The various embodiments include the preparation and use of stabilized polymersome-encapsulated hemoglobin (stabilized PEH) dispersions. Polymersomes of the various embodiment PEH may comprise copolymers that are synthesized to include polymerizable groups within either their hydrophilic or hydrophobic blocks. The polymerizable biodegradable polymers may be utilized to form polymersomes that co-incorporate hemoglobin and a water-soluble initiator in their aqueous interiors, or alternatively, by compartmentalizing hemoglobin in their aqueous cavities and a water-insoluble initiator in their hydrophobic membranes.

Figure 3:
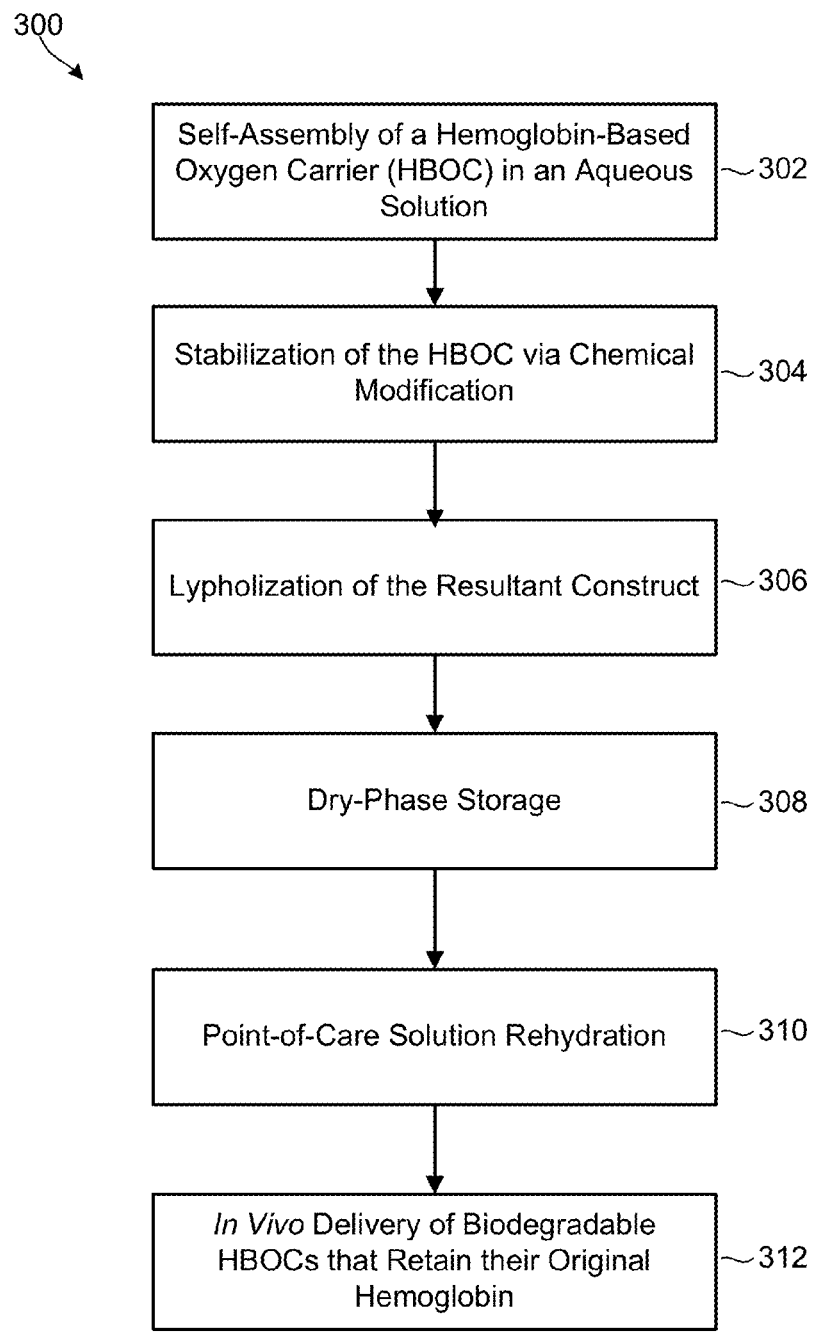
FIG. 3 is a process flow diagram illustrating an embodiment method for the preparation and delivery of a hemoglobin-based oxygen carrier.

FIG. 3 illustrates a method 300 for hemoglobin-based oxygen carrier (HBOC) preparation and delivery. It should be noted that FIG. 3 provides a high-level overview of the method steps and that additional details are provided further below for each step. In step 302 of method 300, the HBOC is self-assembled in aqueous solution. In step 304, the hemoglobin-based oxygen carrier is stabilized via chemical modification. In step 306, the resultant construct is lypholized. In step 308, the resultant construct is stored in dry-phase storage. In step 310, point-of-care solution rehydration is performed. In step 312, biodegradable HBOCs that retain their original hemoglobin are delivered in vivo. As a non-limiting example, polymersome-encapsulated Hb may be prepared and generated via such an HBOC preparation method.

Figure 4:
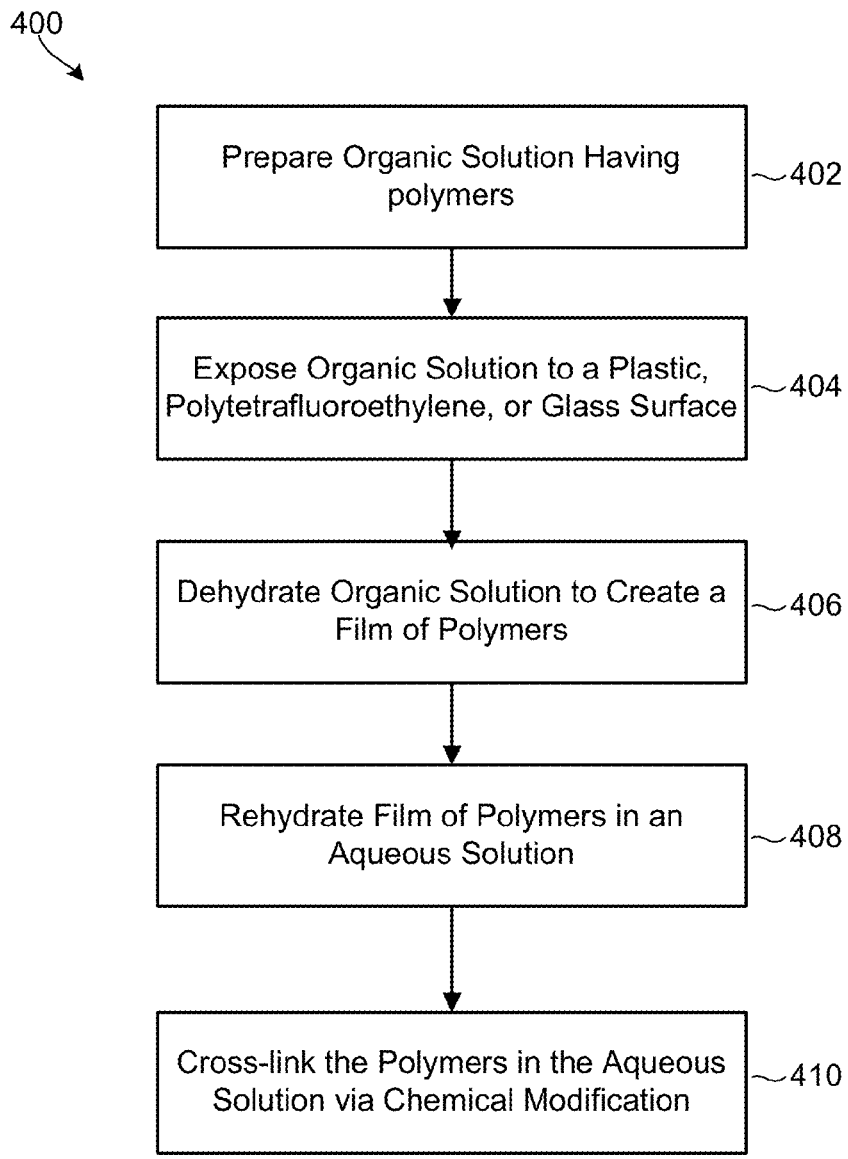
FIG. 4 is a process flow diagram illustrating an embodiment method for preparing a polymersome comprising at least one biocompatible polymer and at least one biodegradable polymer.

FIG. 4 illustrates a method 400 for preparing a polymersome comprising at least one biocompatible polymer and at least one biodegradable polymer. It should be noted that FIG. 4 provides a high-level overview of the method steps and that details for each step are provided further below. In step 402, an organic solution having a plurality of polymers may be prepared. In step 404, the organic solution comprising the plurality of polymers may be exposed to a plastic, polytetrafluoroethylene (i.e., Teflon™)(herein "PTFE"), or glass surface. In step 406, the organic solution may be dehydrated on the plastic, PTFE, or glass surface to create a film of polymers. In step 408, the film of polymers may be rehydrated in an aqueous solution. In step 410, the polymers may be cross-linked in the aqueous solution via chemical modification.

The compositions of the various embodiments may be made by direct hydration methods as described in O'Neil, et. al., Langmuir 2009, 25(16), 9025-9029, the entire contents of which are hereby incorporated by reference. In some embodiments, the compositions comprising one or more embodiments may be made by the hollow fiber extrusion methods disclosed in Rameez, et al., Langmuir, 26 (7); 2010; 5279-5285, the entire contents of which are incorporated herein by reference.

Polymersomes/oxygen carriers of the various embodiments may be made and encapsulated using the following method (step 302). To prepare formulations, 20 total mgs of polymer may be weighed into a 1.5 mL centrifuge tube, heated at 95° C. for 20 min, and mixed. After the samples are cooled to room temperature (15 min minimum), 10 μL of protein solution may be added and diluted with 20, 70, and 900 μL of 10 mmol PBS, pH 7.4, with mixing after each addition. As a control, the polymersomes/oxygen carriers may be formed via dilution with PBS (10, 20, 70, 890 μL of PBS with mixing after each addition) and finally add 10 μL of the protein solution after the formation of the polymersomes/oxygen carriers. In this way, the encapsulation efficiency and loading may be calculated by subtraction. All samples may be prepared in triplicate. Encapsulation efficiencies may be quantified from standard curves generated from the fluorescently labels crosslinked to the polymers of choice under investigation.

In a further embodiment method, polymersomes/oxygen carrier preparation may involve large-scale fractionation of vesiclar particles (step 402). Briefly, a total of 1.25 g of diblock copolymer may be hydrated with 25 mL of 10 mM phosphate buffer (PB) at pH 7.3. Because of the lows solubility of diblock copolymers in PB, the aqueous polymer mixture may be sonicated (e.g., via a Branson Sonifier 450, VWR Scientific, West Chester, Pa.) for 8-10 h at room temperature to yield the stock copolymer solution. The stock copolymer solution may be then mixed with 25 mL of purified Hb(250-300 g/L) to yield a copolymer concentration of 12.5 mg/mL in the Hb copolymer mixture. Empty polymersomes/oxygen carriers may be prepared by diluting the stock copolymer solution in PB, instead of purified Hb solution, to yield a copolymer concentration of 12.5 mg/mL. For the 1 mL volume manual extrusion method (step 404), the Hb-copolymer/copolymer mixture may be extruded 20 times through 200 nm diameter polycarbonate membranes (available from Avanti Polar Lipids Inc., Alabaster, Ala.). However, for the large-scale hollow fiber (HF) extrusion method, the Hb-copolymer/copolymer mixture may be extruded through a 0.2 μm HF membrane (available from Spectrum Laboratories Inc., Rancho Dominguez, Calif.). For both extrusion methods, extruded PEH dispersions may be dialyzed overnight using 300 kDa molecular weight cutoff (hereing "MWCO") dialysis bags (available from Spectrum Laboratories Inc., Rancho Dominguez, Calif.) in PB at 4° C. at a 1:1000 Volume/volume ration (v/v) (extruded PEH/PB) ratio to remove unencapsulated Hb from the vesicular dispersion. An Eclipse asymmetric flow field-flow fractionator (available from Wyatt Technology Corp., Santa Barbara, Calif.) coupled in series to an 18 angle Dawn Heleos multi-angle static light scattering photometer (available from Wyatt Technology Corp., Santa Barbara, Calif.) may be used to measure the size distribution of empty polymersomes/oxygen carriers and PEH particles. The light scattering photometer is equipped with a 30 mW GaAs laser operating at a laser wavelength of 658 nm. Light scattering spectra may be analyzed using the ASTRA software package (available from Wyatt Technology Corp., Santa Barbara, Calif.) to calculate the particle size distribution. The elution buffer may include 10 mM PB at pH 7.3.

To measure the amount of Hb that was encapsulated inside PEH particles, dialyzed PEH dispersions may be lysed using 0.5% v/v Triton X100 (available from Sigma-Aldrich, St. Louis, Mo.) in PB. Lysed PEH samples may be centrifuged at 14 000 rpm for 15 min and the supernatant may be collected for analysis. The concentration of encapsulated Hb obtained after lysing the PEH particles (mg/mL) may be measured using the Bradford method via the Coomassie Plus protein assay kit (available from Pierce Biotechnology, Rockford, Ill.).

As a consequence of the reaction of two or more of the polymerizable groups facilitated by the initiator, stabilized PEH dispersions may be generated via formation of covalent bonds between chains of the copolymers forming the polymersome membranes (step 304). These stabilized PEH constructs may be further dried via well-established lyophilization protocols (step 306) without disrupting the formed polymersome structure or losing the encapsulated hemoglobin. In some embodiments, the polymersomes/oxygen carriers are administered in the aqueous solution. If lyophilized, in some embodiments, the polymersomes/oxygen carriers are reconstituted in an appropriate aqueous solution and administered to a subject (step 312). In some embodiments, lyophilized biodegradable PEH may be stored (step 308) in a dessicator (free of O2) at 4° C. for varying periods of time without polymer or hemoglobin degradation as the dried suspensions are free of aqueous free radicals, protons, etc. The polymersomes/oxygen carriers may be rehydrated at point-of-care (step 310) prior to delivery (step 312).

To generate stabilized polymersomes/oxygen carriers, polymerizable units may be chemically linked to either the hydrophilic or hydrophobic ends of the copolymer after synthesis. One or more crosslinks between multiblock copolymer chains may be formed between the polymerizable units and the hydrophilic or hydrophobic polymers of the various embodiments. These cross-links may be suitably formed by introducing a composition having multiple polymerizable groups to the chains of multiblock copolymer, although in some cases, the multiblock copolymer itself includes multiple polymerizable groups.

Cross-linking between chains of a membrane (step 410) may be achieved via activation of the polymerization reaction by an initiator, which enhances the rigidity of the polymersome composition.

Figure 5:
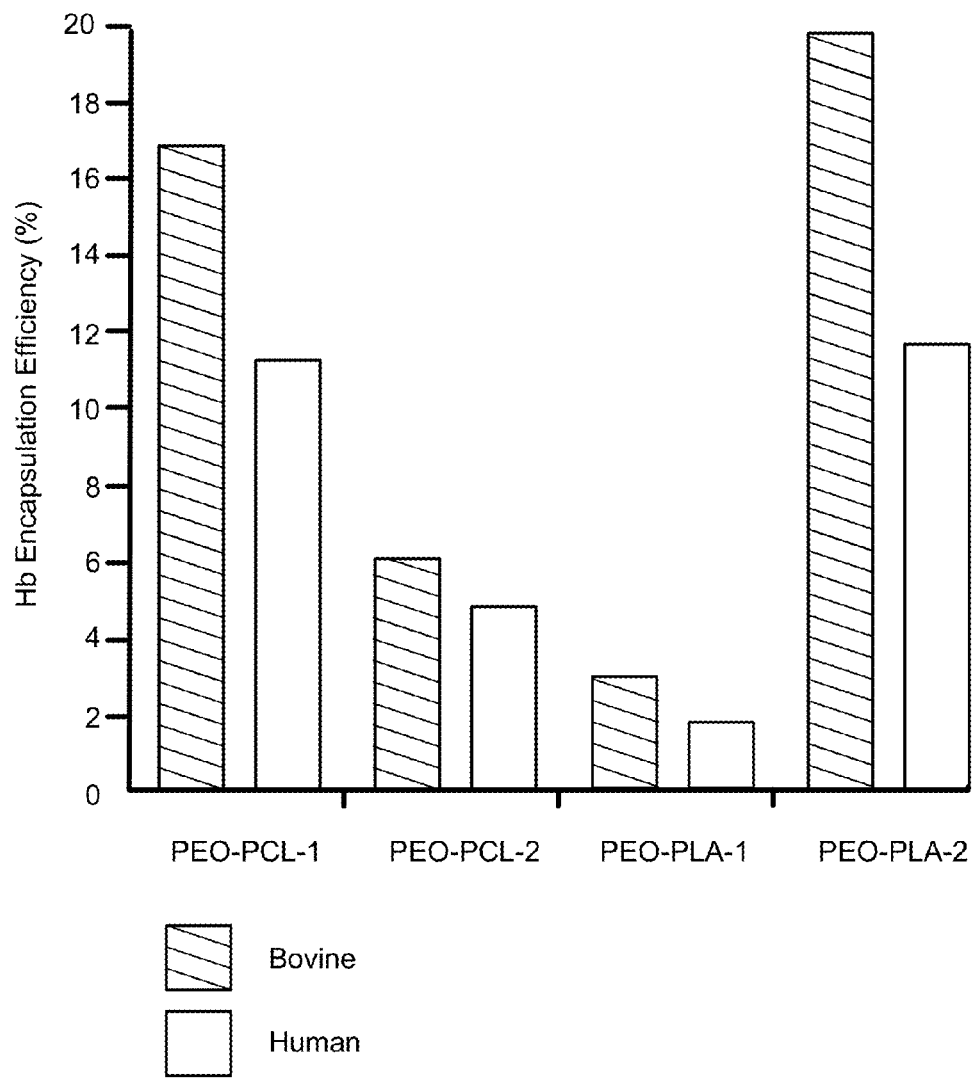
FIG. 5 is a bar chart illustrating the hemoglobin encapsulation efficiencies of four polymersome-encapsulated hemoglobin formulations extruded through 200 nm polycarbonate membranes.

FIG. 5 illustrates the hemoglobin encapsulation efficiencies of four polymersome-encapsulated hemoglobin formulations extruded through 200 nm polycarbonate membranes. Specifically, FIG. 5 illustrates the hemoglobin encapsulation efficiency of PEO-b-PCL-1 (1.65 KDa), PEO-b-PCL-2 (15 KDa), PEO-b-PLA-1 (10 kDa) and PEO-b-PLA-2 (2.45 KDa). As discussed above, the various embodiments provide PEH constructs having an average radius between 100-125 nm with polydispersity index<1.1 and a hemoglobin encapsulation efficiency>50%.

Figure 6:
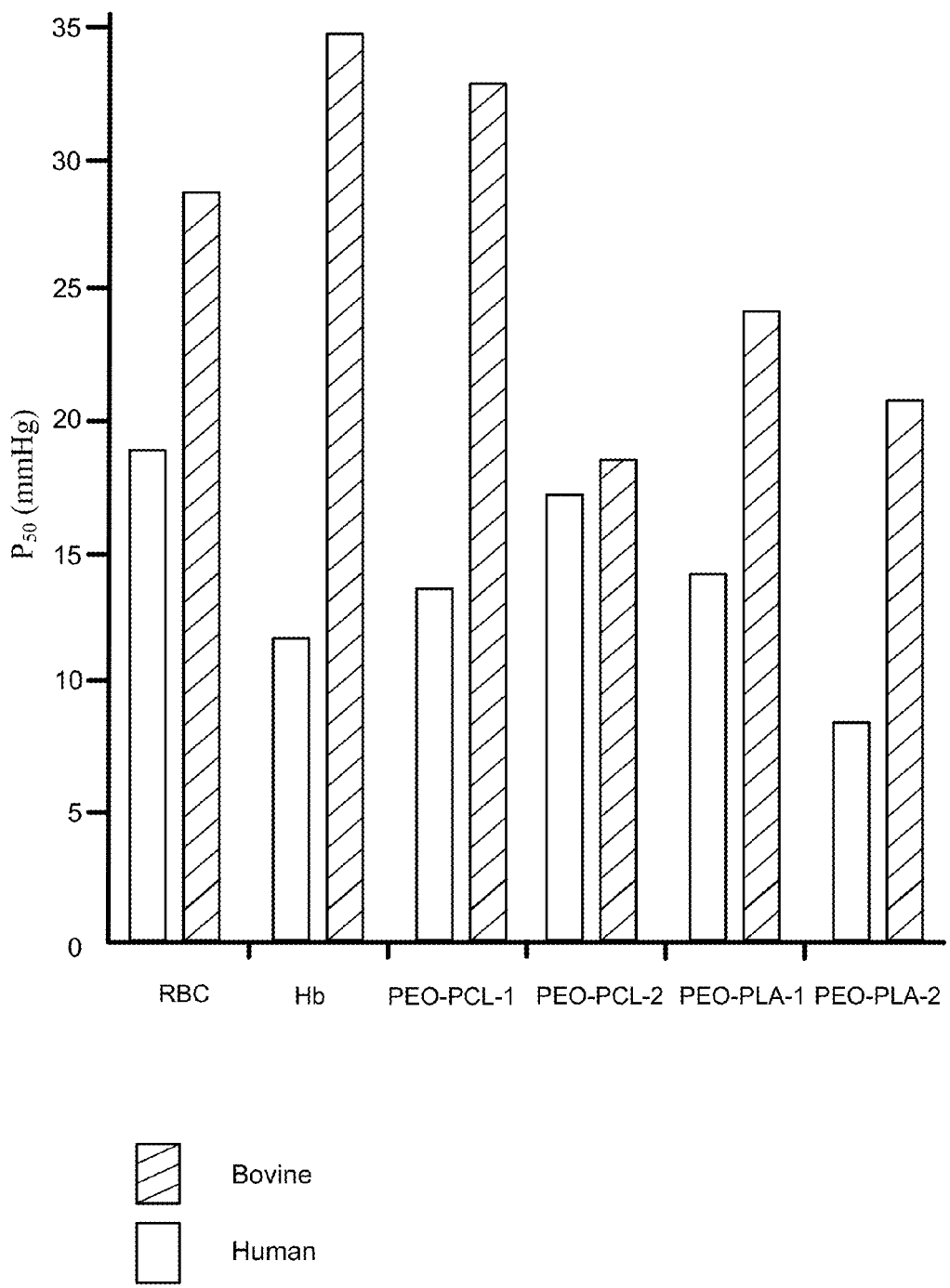
FIG. 6 is a bar chart illustrating the $P_{50}$ (mmHg) of red blood cells, hemoglobin and four polymersome-encapsulated hemoglobin formulations extruded through 200 nm polycarbonate membranes.

FIG. 6 illustrates the $P_{50}$ (mmHg) of red blood cells, hemoglobin and four polymersome-encapsulated hemoglobin formulations (PEO-b-PCL-1 (1.65 KDa), PEO-b-PCL-2(15 KDa), PEO-b-PLA-1 (10 kDa) and PEO-b-PLA-2 (2.45 KDa)) extruded through 200 nm polycarbonate membranes. As mentioned above, the various embodiments provide PEH constructs having a tunable $P_{50}$ between 20-50 mm hemoglobin, co-operativity coefficient>2, and at least an order of magnitude smaller NO binding rate constant than that measured for liposome-encapsulated hemoglobin dispersions (LEHs) at similar hemoglobin loading concentrations.

In some embodiments, the multiple polymerizable groups may be chosen from acrylates, methacrylates, acrylamides, methacrylamides, vinyls, vinyl sulfone units or a combination thereof. In some embodiments, the oxygen carriers or polymersomes comprise the polymerizable groups from about 0 weight (wt) % to about 5 wt % of the total weight of the composition. In some embodiments, the oxygen carriers or polymersomes comprise the polymerizable groups from about 5 wt % to about 10 wt % of the total weight of the composition. In some embodiments, the oxygen carriers or polymersomes comprise the polymerizable groups from about 10 wt % u to about 20 wt % of the total weight of the composition. In some embodiments, the oxygen carriers or polymersomes comprise the polymerizable groups from about 20 wt % to about 30 wt % of the total weight of the composition. In some embodiments, the oxygen carriers or polymersomes comprise the polymerizable groups from about 30 wt % to about 40 wt % of the total weight of the composition. In some embodiments, the oxygen carriers or polymersomes comprise the polymerizable groups from about 40 wt % to about 50 wt % of the total weight of the composition. In some embodiments, the oxygen carriers or polymersomes comprise the polymerizable groups from about 50 wt % to about 60 wt % of the total weight of the composition. In some embodiments, the oxygen carriers or polymersomes comprise the polymerizable groups from about 60 wt % to about 70 wt % of the total weight of the composition. In some embodiments, the oxygen carriers or the polymersomes comprise the polymerizable groups from about 70 wt % up to about 80 wt % of the total weight of the composition. In some embodiments, the oxygen carriers or polymersomes comprise the polymerizable groups from about 80 wt % up to about 90 wt % of the total weight of the composition. In some embodiments, the oxygen carriers or polymersomes comprise the polymerizable groups from about 90 wt % up to about 95 wt % of the total weight of the composition.

In certain embodiments, the polymerizable group may be conjugated to copolymer's hydrophilic block made from either poly(ethylene oxide), poly(ethylene glycol), poly (acrylic acid), and the like. In other embodiments, the polymerizable group may be conjugated to the copolymer's hydrophobic block made from either poly(ε-caprolactone), poly(γ-methyl ε-caprolactone), poly(menthide), poly(lactide), poly(glycolide), poly(methylglycolide), poly(dimethylsiloxane), poly(isobutylene), poly(styrene), poly(ethylene), poly(propylene oxide), etc.

The initiator may be a molecule that generates/reacts to heat, light, pH, solution ionic strength, osmolarity, pressures, etc. In some embodiments, the initiator may be photoreactive and cross-links the polymers of the oxygen carrier or polymersome via exposure to ultraviolet light.

In various embodiments, the compositions may be prepared without the use of organic solvents.

The compositions of the various embodiments may include polymersomes comprising poly(ethylene oxide)-block-poly (ε-caprolactone) copolymers that have been modified with an acrylate moiety at the hydrophobic block terminus. In some embodiments, the oxygen carriers or polymersomes may comprise crosslinked polymers formed between the poly(ε-caprolactone) terminus and a diacrylate using a UV initiator, such as 2,2-dimethoxy-2-phenylacetophenone (DMPA). In some embodiments, DMPA is compartmentalized in the polymersome membrane during polymersome assembly while hemoglobin occupies the internal aqueous compartment of the carrier.

The composition of the various embodiments may also comprise polymersomes or oxygen carriers that have increased degradative half-lives. Circulation times of oxygen carrier and polymersomes may be generally limited to hours (or up to one day) because of either rapid clearance by the mononuclear phagocytic system (MPS) of the liver and spleen, or by excretion.

The most common lamellae-forming amphiphiles may have a hydrophilic volume fraction between 20 and 50%. In some embodiments, the hydrophilic volume fraction of the oxygen carriers, nanoparticles and/or polymersomes is up to about 20%. In some embodiments, the hydrophilic volume fraction of the oxygen carriers, nanoparticles and/or polymersomes is up to about 19%. In some embodiments, the hydrophilic volume fraction of the oxygen carriers, nanoparticles and/or polymersomes is up to about 18%. In some embodiments, the hydrophilic volume fraction of the oxygen carriers, nanoparticles and/or polymersomes is up to about 17%. In some embodiments, the hydrophilic volume fraction of the oxygen carriers, nanoparticles and/or polymersomes is up to about 16%. In some embodiments, the hydrophilic volume fraction of the oxygen carriers, nanoparticles and/or polymersomes is up to about 15%. In some embodiments, the hydrophilic volume fraction of the oxygen carriers, nanoparticles and/or polymersomes is less than 20%. In some embodiments, the hydrophilic volume fraction of the oxygen carriers, nanoparticles and/or polymersomes is from about 1% to about 20%. It should be noted that the ability of amphiphilic and super-amphiphilic molecules to self-assemble can be largely assessed, without undue experimentation, by suspending the synthetic super-amphiphile in aqueous solution and looking for lamellar and vesicular structures as judged by simple observation under any basic optical microscope, cryogenic transmission electron microscope, or through the scattering of light.

The effective amount of the composition may depend on any number of variables, including, the species, breed, size, height, weight, age, overall health of the subject, the type of formulation, the mode or manner of administration, the type and/or severity of the particular condition being treated, or the need to modulate the activity of the molecular pathway induced by association of the analog to its receptor. The appropriate effective amount can be routinely determined by those of skill in the art using routine optimization techniques and the skilled and informed judgment of the practitioner and other factors evident to those skilled in the art.

A therapeutically effective dose of the oxygen carriers of the various embodiments may provide partial or complete biological activity as compared to the biological activity of a patient's or subject's physiologically mean, median or minimum tissue oxygenation. A therapeutically effective dose of the oxygen carriers of the various embodiments may provide a complete or partial amelioration of symptoms associated with a disease, disorder or ailment for which the subject is being treated.

The oxygen carriers of the various embodiments may delay the onset or lower the chances that a subject develops one or more symptoms associated with the disease, disorder, or ailment for which the subject is being treated. In some embodiments, an effective amount is the amount of a compound required to treat or prevent a consequence resulting from low or poor tissue oxygenation. In the various embodiments, the effective amount of active compound(s) used for therapeutic treatment of conditions caused by or contributing to low or poor tissue oxygenation varies depending upon the manner of administration, the age, body weight, and general health of the patient.

Soluble amphiphiles, proteins, ligands, allosteric effectors, oxygen binding compounds can bind to and/or intercalate within a membrane. Such a membrane may also be semipermeable to solutes, sub-microscopic in its thickness (d), and result from a process of self-assembly or directed assembly. The membrane can have fluid or solid properties, depending on temperature and on the chemistry of the amphiphiles from which it is formed. At some temperatures, the membrane can be fluid (having a measurable viscosity), or it can be solid-like, with an elasticity and bending rigidity. The membrane can store energy through its mechanical deformation, or it can store electrical energy by maintaining a transmembrane potential. Under some conditions, membranes can adhere to each other and coalesce (fuse).

As mentioned above, in various embodiments, hemoglobin may be used as the oxygen-binding compound. In some embodiments, the oxygen-binding compound is a one, two, or three monomeric subunits of hemoglobin. In some embodiments, the oxygen-binding compound is protein with oxygen binding properties that are similar to hemoglobin. In some embodiments, the oxygen-binding compound is genetically- or chemically-modified hemoglobin or an oxygen binding protein isolated from another species that possesses gaseous binding characteristics that are similar to human hemoglobin. In some embodiments, the oxygen-binding compound is modified myoglobin. In some embodiments, the oxygen-binding compound is a one, two, or three monomeric subunits of myoglobin. In some embodiments, the oxygen-binding compound is chosen from a protein, small molecule, polypeptide, nucleic acid molecule, or any combination thereof. In some embodiments, the oxygen-binding compound is a protein. In some embodiments, the oxygen-binding compound is a polypeptide. In some embodiments, the oxygen-binding compound is a polypeptide with a genetically or chemically modified heme group. In some embodiments, the oxygen-binding compound is a small molecule comprising a heme group.

In some embodiments, the oxygen carrier transports an effective amount of oxygen in order to treat a subject or to prevent a subject from suffering from a disease or disorder in which their blood does not carry or release sufficient levels of oxygen to tissues. In some embodiments the oxygen carrier comprises an effective amount of oxygen in order to treat or prevent the spread of cancer in a subject in need thereof. In some embodiments, the oxygen carrier comprises an effective amount of oxygen in order to promote wound healing in a subject in need thereof.

In some embodiments, the allostreic effector is 2,3-Bisphosphoglycerate or an isomer derived therefrom. Allosteric effectors such as 2,3Bisphosphoglycerate may increase the offload of oxygen from the oxygen carrier or polymersome of the various embodiments to a tissue or cell that is deoxygenated within a subject.

As mentioned above, critical lysis tension (Tc) is the tension at which a particle ruptures when subject to an external force, as measured by micropipette aspiration and expressed as milliNewtons/meter (mN/m). The change in critical lysis tension of an oxygen carrier or polymersome may be measured before and after loading of the oxygen carrier, nanoparticle and/or polymersome with hemoglobin, another oxygen-binding compound, or a mixture of one or more oxygen-binding compounds.

In various embodiments, the oxygen carriers, nanoparticles and/or polymersomes have a change of critical lysis tension of no more than 20%. In various embodiments, the oxygen carriers, nanoparticles and/or polymersomes have a change of critical lysis tension of no more than 19%. In various embodiments, the oxygen carriers, nanoparticles and/or polymersomes have a change of critical lysis tension of no more than 18%. In various embodiments, the oxygen carriers, nanoparticles and/or polymersomes have a change of critical lysis tension of no more than 17%. In various embodiments, the oxygen carriers, nanoparticles and/or polymersomes have a change of critical lysis tension of no more than 16%. In various embodiments, the oxygen carriers, nanoparticles and/or polymersomes have a change of critical lysis tension of no more than 15%. In various embodiments, the oxygen carriers, nanoparticles and/or polymersomes have a change of critical lysis tension of no more than 14%. In various embodiments, the oxygen carriers, nanoparticles and/or polymersomes have a change of critical lysis tension of no more than 13%. In various embodiments, the oxygen carriers, nanoparticles and/or polymersomes have a change of critical lysis tension of no more than 12%. In various embodiments, the oxygen carriers, nanoparticles and/or polymersomes have a change of critical lysis tension of no more than 11%. In various embodiments, the oxygen carriers, nanoparticles and/or polymersomes have a change of critical lysis tension of no more than 10%. In various embodiments, the oxygen carriers, nanoparticles and/or polymersomes have a change of critical lysis tension from about 5% to about 10%. In various embodiments, the oxygen carriers, nanoparticles and/or polymersomes may have a change of critical lysis tension from about 10% to about 15%. In various embodiments, the oxygen carriers, nanoparticles and/or polymersomes have a change of critical lysis tension from about 15% to about 20%. In various embodiments, the oxygen carriers, nanoparticles and/or polymersomes have a change of critical lysis tension from about 1% to about 5%.

As mentioned above, critical areal strain (Ac) is the areal strain realized by the oxygen carriers, nanoparticles and/or polymersomes at the critical lysis tension. In various embodiments, the oxygen carriers, nanoparticles and/or polymersomes have a critical areal strain from about 20% to about 50%. In various embodiments, the oxygen carriers, nanoparticles and/or polymersomes have a critical areal strain from about 20% to about 25%. In various embodiments, the oxygen carriers, nanoparticles and/or polymersomes have a critical areal strain from about 25% to about 30%. In various embodiments, the oxygen carriers, nanoparticles and/or polymersomes have a critical areal strain from about 30% to about 35%. In various embodiments, the oxygen carriers, nanoparticles and/or polymersomes have a critical areal strain from about 35% to about 40%. In various embodiments, the oxygen carriers, nanoparticles and/or polymersomes have a critical areal strain from about 40% to about 45%. In various embodiments, the oxygen carriers, nanoparticles and/or polymersomes have a critical areal strain from about 45% to about 50%.

As mentioned above, a "hemoglobin loading capacity" is a measurement of a hemoglobin-based oxygen carrier and is defined as the weight of hemoglobin within the oxygen carrier divided by the total weight of carrier. In some embodiments, the oxygen carrier or polymersomes have a hemoglobin loading capacity of greater than about 15. In some embodiments, the oxygen carrier or polymersomes have a hemoglobin loading capacity of greater than 20. In some embodiments, the oxygen carrier or polymersomes have a hemoglobin loading capacity of greater than 25. In some embodiments, the oxygen carrier or polymersomes have a hemoglobin loading capacity of greater than 26. In some embodiments, the oxygen carrier or polymersomes have a hemoglobin loading capacity of greater than 27. In some embodiments, the oxygen carrier or polymersomes have a hemoglobin loading capacity of greater than 28. In some embodiments, the oxygen carrier or polymersomes have a hemoglobin loading capacity of greater than 29. In some embodiments, the oxygen carrier or polymersomes have a hemoglobin loading capacity of greater than 30.

As mentioned above, a "hemoglobin loading efficiency" is a fundamental measurement of a hemoglobin-based oxygen carrier and is defined as the weight of hemoglobin that is encapsulated and/or incorporated within a carrier suspension divided by the weight of the original hemoglobin in solution prior to encapsulation (expressed as a %). In some embodiments, the oxygen carrier or polymersomes have a hemoglobin loading efficiency of greater than about 10%. In some embodiments, the oxygen carriers, nanoparticles and/or polymersomes have a hemoglobin loading efficiency of greater than about 11%. In some embodiments, the oxygen carriers, nanoparticles and/or polymersomes have a hemoglobin loading efficiency of greater than about 12%. In some embodiments, the oxygen carriers, nanoparticles and/or polymersomes have a hemoglobin loading efficiency of greater than about 13%. In some embodiments, the oxygen carriers, nanoparticles and/or polymersomes have a hemoglobin loading efficiency of greater than about 14%. In some embodiments, the oxygen carriers, nanoparticles and/or polymersomes have a hemoglobin loading efficiency of greater than about 15%. In some embodiments, the oxygen carriers, nanoparticles and/or polymersomes have a hemoglobin loading efficiency of greater than about 16%. In some embodiments, the oxygen carriers, nanoparticles and/or polymersomes have a hemoglobin loading efficiency of greater than about 17%. In some embodiments, the oxygen carriers, nanoparticles and/or polymersomes have a hemoglobin loading efficiency of greater than about 18%. In some embodiments, the oxygen carriers, nanoparticles and/or polymersomes have a hemoglobin loading efficiency of greater than about 19%. In some embodiments, the oxygen carriers, nanoparticles and/or polymersomes have a hemoglobin loading efficiency of greater than about 20%. In some embodiments, the oxygen carriers, nanoparticles and/or polymersomes have a hemoglobin loading efficiency of greater than about 21%. In some embodiments, the oxygen carriers, nanoparticles and/or polymersomes have a hemoglobin loading efficiency of greater than about 22%. In some embodiments, the oxygen carriers, nanoparticles and/or polymersomes have a hemoglobin loading efficiency of greater than about 23%. In some embodiments, the oxygen carriers, nanoparticles and/or polymersomes have a hemoglobin loading efficiency of greater than about 24%. In some embodiments, the oxygen carriers, nanoparticles and/or polymersomes have a hemoglobin loading efficiency of greater than about 25%. In some embodiments, the oxygen carriers, nanoparticles and/or polymersomes have a hemoglobin loading efficiency of greater than about 26%. In some embodiments, the oxygen carriers, nanoparticles and/or polymersomes have a hemoglobin loading efficiency of greater than about 27%. In some embodiments, the oxygen carriers, nanoparticles and/or polymersomes have a hemoglobin loading efficiency of greater than about 28%. In some embodiments, the oxygen carriers, nanoparticles and/or polymersomes have a hemoglobin loading efficiency of greater than about 29%. In some embodiments, the oxygen carriers, nanoparticles and/or polymersomes have a hemoglobin loading efficiency of greater than about 30%.

In some embodiments, the oxygen carriers, nanoparticles and/or polymersomes have a hemoglobin loading efficiency from about 10% to about 35%. In some embodiments, the oxygen carriers, nanoparticles and/or polymersomes have a hemoglobin loading efficiency from about 15% to about 35%. In some embodiments, the oxygen carriers, nanoparticles and/or polymersomes have a hemoglobin loading efficiency from about 18% to about 35%. In some embodiments, the oxygen carriers, nanoparticles and/or polymersomes have a hemoglobin loading efficiency from about 20% to about 35%. In some embodiments, the oxygen carriers, nanoparticles and/or polymersomes have a hemoglobin loading efficiency from about 22% to about 35%. In some embodiments, the oxygen carriers, nanoparticles and/or polymersomes have a hemoglobin loading efficiency from about 24% to about 35%. In some embodiments, the oxygen carriers, nanoparticles and/or polymersomes have a hemoglobin loading efficiency from about 26% to about 35%. In some embodiments, the oxygen carriers, nanoparticles and/or polymersomes have a hemoglobin loading efficiency from about 28% to about 35%. In some embodiments, the oxygen carriers, nanoparticles and/or polymersomes have a hemoglobin loading efficiency from about 30% to about 35%.

In various embodiments, the polymersome-hemoglobin solution is administered to a subject. The subject may be a mammal, a non-human animal, a canine and/or a vertebrate.

The various embodiments may include a polymersomes or oxygen carriers with varying sizes. In some embodiments, the oxygen carrier, nanoparticle and/or polymersome includes a roughly spherical shape and has a diameter of about 5 nm to about 1 μm. In some embodiments, the polymersome or oxygen carrier has a diameter of about 5 nm to about 25 nm. In some embodiments, the polymersome or oxygen carrier has a diameter of about 10 nm to about 20 nm. In some embodiments, the polymersome or oxygen carrier has a diameter of about 20 nm to about 30 nm. In some embodiments, the polymersome or oxygen carrier has a diameter of about 30 nm to about 40 nm. In some embodiments, the polymersome or oxygen carrier has a diameter of about 40 nm to about 50 nm. In some embodiments, the polymersome or oxygen carrier has a diameter of about 50 nm to about 60 nm. In some embodiments, the polymersome or oxygen carrier has a diameter of about 60 nm to about 70 nm. In some embodiments, the polymersome or oxygen carrier has a diameter of about 70 nm to about 80 nm. In some embodiments, the polymersome or oxygen carrier has a diameter of about 80 nm to about 90 nm. In some embodiments, the polymersome or oxygen carrier has a diameter of about 90 nm to about 100 nm.

In various embodiments, the oxygen carrier, nanoparticle and/or polymersome includes a roughly spherical shape and has a diameter of about 50 nm to about 1 µm. In various embodiments, the oxygen carrier, nanoparticle and/or polymersome has a diameter of about 50 nm to about 250 nm. In various embodiments, the oxygen carrier, nanoparticle and/or polymersome has a diameter of about 100 nm to about 200 nm. In various embodiments, the oxygen carrier, nanoparticle and/or polymersome has a diameter of about 200 nm to about 300 nm. In various embodiments, the oxygen carrier, nanoparticle and/or polymersome has a diameter of about 300 nm to about 400 nm. In various embodiments, the oxygen carrier, nanoparticle and/or polymersome has a diameter of about 400 nm to about 500 nm. In various embodiments, the oxygen carrier, nanoparticle and/or polymersome has a diameter of about 500 nm to about 600 nm. In various embodiments, the oxygen carrier, nanoparticle and/or polymersome has a diameter of about 600 nm to about 700 nm. In various embodiments, the oxygen carrier, nanoparticle and/or polymersome has a diameter of about 700 nm to about 800 nm. In various embodiments, the oxygen carrier, nanoparticle and/or polymersome has a diameter of about 800 nm to about 900 nm. In various embodiments, the polymersome or oxygen carrier has a diameter of about 900 nm to about 1 µm.

In various embodiments, the oxygen carrier includes a nanoparticle that has a diameter of about 5 nm to about 100 nm. In various embodiments, the oxygen carrier includes a nanoparticle that has a diameter of about 5 nm to about 10 nm. In various embodiments, the oxygen carrier includes a nanoparticle that has a diameter of about 10 nm to about 50 nm. In various embodiments, the oxygen carrier includes a nanoparticle that has a diameter of about 50 nm to about 100 nm. In various embodiments, the oxygen carrier includes a nanoparticle that has a diameter of about 100 nm to about 300 nm. In various embodiments, the oxygen carrier includes a nanoparticle that has a diameter of about 300 nm to about 500 nm. In various embodiments, the oxygen carrier includes a nanoparticle that has a diameter of about 500 nm to about 1 µm.

In various embodiments, the oxygen carrier has a diameter of about 5 nm to about 100 nm. In various embodiments, the oxygen carrier has a diameter of about 5 nm to about 10 nm. In various embodiments, the oxygen carrier has a diameter of about 10 nm to about 50 nm. In various embodiments, the oxygen carrier has a diameter of about 50 nm to about 100 nm. In various embodiments, the oxygen carrier has a diameter of about 100 nm to about 300 nm. In various embodiments, the oxygen carrier has a diameter of about 300 nm to about 500 nm. In various embodiments, the oxygen carrier has a diameter of about 500 nm to about 1 µm.

In a further embodiment, the oxygen carriers or polymersomes may be formed with a range of varying membrane thicknesses. The thickness of the membrane may depend upon the molecular weight of the polymers and the types of polymers used in the preparation of the oxygen carriers or polymersomes. In some embodiments, the membrane may be a single, double, triple, quadruple, or more layers of polymers. In some embodiments, the oxygen carriers or polymersomes have a polymer membrane thickness from about 5 nm to about 35 nm. In some embodiments, the oxygen carriers or polymersomes have a membrane thickness from about 5 nm to about 10 nm. In some embodiments, the oxygen carriers or polymersomes have a membrane thickness from about 10 nm to about 15 nm. In some embodiments, the oxygen carriers or polymersomes have a membrane thickness from about 15 nm to about 20 nm. In some embodiments, the oxygen carriers or polymersomes have a membrane thickness from about 20 nm to about 25 nm. In some embodiments, the oxygen carriers or polymersomes have a membrane thickness from about 25 nm to about 30 nm. In some embodiments, the oxygen carriers or polymersomes have a membrane thickness from about 30 nm to about 35 nm. In some embodiments, the oxygen carriers or polymersomes have a polymer membrane that is no more than about 5 nm in thickness. In some embodiments, the oxygen carriers or polymersomes have a polymer membrane that is no more than about 10 nm in thickness. In some embodiments, the oxygen carriers or polymersomes have a polymer membrane that is no more than about 15 nm in thickness. In some embodiments, the oxygen carriers or polymersomes have has a polymer membrane that is no more than about 20 nm in thickness. In some embodiments, the oxygen carriers or polymersomes have a polymer membrane that is no more than about 25 nm in thickness. In some embodiments, the oxygen carriers or polymersomes have a polymer membrane that is no more than about 30 nm in thickness. In some embodiments, the oxygen carriers or polymersomes have a polymer membrane that is no more than about 35 nm in thickness.

Clinical studies have shown that circulation times of spherical carriers may be generally extended threefold in humans over rats. As proposed for clinically used drug formulations of PEG-liposomes, oxygen carriers and polymersomes with long circulating lifetime may increase the drug exposure to cancer cells, low oxygenated tissues, or healing wounds, and thereby increase the time-integrated dose, commonly referred to in drug delivery as 'the area under the curve. Additionally, the enhanced permeation and retention effect that allows small solutes and micelles to permeate the leaky blood vessels of a rapidly expanding tumor might also allow oxygen carriers and polymersomes to transport into the tumor stroma. Persistent circulation of the oxygen carriers and polymersomes has many practical applications because these vehicles can increase exposure of drugs to cancer cells, low or poor oxygenated tissues, or healing wounds.

The compositions of the various embodiments may comprise polymersomes or oxygen carriers that have increased circulatory half-lives. In some embodiments, the compositions have a certain percent mass composition of polymer designed to have a circulatory half-life from about 12 hours to about 36 hours, and a degradative half-life from about 38 to about 60 hours. In some embodiments, the compositions have a certain percent mass composition of polymer designed to have circulatory half-life about 12 hours less than the degradative half-life of the oxygen-carrier or polymersome. This delay in degradation may vary depending upon the route of administration and/or the targeted micro-compartment or subcellular microenvironment where the polymersome or oxygen carrier deploys its contents for treatment or prevention of the disease states or disorders disclosed herein. In some embodiments, the compositions comprising polymersomes or oxygen carriers have circulatory half-life about 11 hours less than the degradative half-life of the oxygen-carrier or polymersome. In some embodiments, the compositions comprising polymersomes or oxygen carriers have circulatory half-life about 10 hours less than the degradative half-life of the oxygen-carrier or polymersome. In some embodiments, the compositions comprising polymersomes or oxygen carriers have circulatory half-life about 9 hours less than the degradative half-life of the oxygen-carrier or polymersome. In some embodiments, the compositions comprising polymersomes or oxygen carriers have circulatory half-life about 8 hours less than the degradative half-life of the oxygen-carrier or polymersome. In some embodiments, the compositions comprising polymersomes or oxygen carriers have circulatory half-life about 7 hours less than the degradative half-life of the oxygen-carrier or polymersome. In some embodiments, the compositions comprising polymersomes or oxygen carriers have circulatory half-life about 6 hours less than the degradative half-life of the oxygen-carrier or polymersome. In some embodiments, the compositions comprising polymersomes or oxygen carriers have circulatory half-life about 5 hours less than the degradative half-life of the oxygen-carrier or polymersome. In some embodiments, the compositions comprising polymersomes or oxygen carriers have circulatory half-life about 4 hours less than the degradative half-life of the oxygen-carrier or polymersome. In some embodiments, the compositions comprising polymersomes or oxygen carriers have circulatory half-life about 3 hours less than the degradative half-life of the oxygen-carrier or polymersome. In some embodiments, the compositions comprising polymersomes or oxygen carriers have circulatory half-life about 2 hours less than the degradative half-life of the oxygen-carrier or polymersome. In some embodiments, the compositions comprising polymersomes or oxygen carriers have circulatory half-life about 1 hours less than the degradative half-life of the oxygen-carrier or polymersome. In some embodiments, the compositions comprising polymersomes or oxygen carriers have circulatory half-life about 14 hours less than the degradative half-life of the oxygen-carrier or polymersome. In some embodiments, the compositions comprising polymersomes or oxygen carriers have circulatory half-life from about 1 hour to about 20 hours less than the degradative half-life of the oxygen-carrier or polymersome. In some embodiments, the compositions comprising polymersomes or oxygen carriers have a certain percent mass composition of polymer designed to have a circulatory half-life of about 36 hours, and a degradative half-life greater than about 48 hours. In some embodiments, the compositions comprising polymersomes or oxygen carriers have a certain percent mass composition of polymer designed to have a circulatory half-life from about 24 hours to about 36 hours, and a degradative half-life from about 38 to about 60 hours. In some embodiments, the compositions comprising polymersomes or oxygen carriers have a certain percent mass composition of polymer designed to have a circulatory half-life from about 28 hours to about 36 hours, and a degradative half-life from about 38 to about 60 hours. In some embodiments, the compositions comprising polymersomes or oxygen carriers have a certain percent mass composition of polymer designed to have a circulatory half-life from about 30 hours to about 36 hours, and a degradative half-life from about 38 to about 60 hours. In some embodiments, the compositions comprising polymersomes or oxygen carriers have a certain percent mass composition of polymer designed to have a circulatory half-life of no more than 36 hours, and a degradative half-life from about 38 to about 60 hours.

In some embodiments, in vivo delivery to a subject is achieved by intravenous, inhalational, transmucosal (e.g. buccal) or transcutaneous routes of administration. Dosages for a given host may be determined using conventional considerations (e.g., by customary comparison of the differential activities of the subject preparations and a known appropriate, conventional pharmacological protocol).

The pharmaceutical composition of the various embodiments may be loaded with different concentrations of oxygen binding molecule per gram of polymer. In some embodiments, the pharmaceutical composition comprises from about 10 to about 40 mg oxygen binding compound/mg polymer. In some embodiments, the pharmaceutical composition comprises from about 20 to about 40 mg oxygen binding compound/mg polymer. In some embodiments, the pharmaceutical composition comprises from about 30 to about 40 mg oxygen binding compound/mg polymer. In some embodiments, the pharmaceutical composition comprises from about 35 to about 40 mg oxygen binding compound/mg polymer. In some embodiments, the pharmaceutical composition comprises from about 25 to about 40 mg oxygen binding compound/mg polymer. In some embodiments, the pharmaceutical composition comprises from about 25 to about 35 mg oxygen binding compound/mg polymer. In some embodiments, the pharmaceutical composition comprises from about 25 to about 30 mg oxygen binding compound/mg polymer. In some embodiments, the pharmaceutical composition comprises from about 20 to about 25 mg oxygen binding compound/mg polymer. In some embodiments, the pharmaceutical composition comprises from about 10 to about 15 mg oxygen binding compound/mg polymer.

In some embodiments, the pharmaceutical composition comprises from about 10 to about 40 mg hemoglobin/mg polymer. In some embodiments, the pharmaceutical composition comprises from about 20 to about 40 mg hemoglobin/mg polymer. In some embodiments, the pharmaceutical composition comprises from about 30 to about 40 mg hemoglobin/mg polymer. In some embodiments, the pharmaceutical composition comprises from about 35 to about 40 mg hemoglobin/mg polymer. In some embodiments, the pharmaceutical composition comprises from about 25 to about 40 mg hemoglobin/mg polymer. In some embodiments, the pharmaceutical composition comprises from about 25 to about 35 mg hemoglobin/mg polymer. In some embodiments, the pharmaceutical composition comprises from about 25 to about 30 mg hemoglobin/mg polymer. In some embodiments, the pharmaceutical composition comprises from about 20 to about 25 mg hemoglobin/mg polymer. In some embodiments, the pharmaceutical composition comprise from about 10 to about 15 mg hemoglobin/mg polymer. In some embodiments the hemoglobin dosages may be replaced by the same weight of myoglobin.

In some embodiments, the pharmaceutical composition is a liquid formulation, wherein the dosage may be from about 1 unit of compositions to about 50 units of solution, wherein a unit of solution comprises from about 60 g of hemoglobin to about 70 g of hemoglobin. In some embodiments, a unit of a liquid formulation comprising the pharmaceutical composition comprises about 61 grams of hemoglobin. In some embodiments, a unit of a liquid formulation comprising the pharmaceutical composition comprises about 62 grams of hemoglobin. In some embodiments, a unit of a liquid formulation comprising the pharmaceutical composition comprises about 63 grams of hemoglobin. In some embodiments, a unit of a liquid formulation comprising the pharmaceutical composition comprises about 64 grams of hemoglobin. In some embodiments, a unit of a liquid formulation comprising the pharmaceutical composition comprises about 65 grams of hemoglobin. In some embodiments, a unit of a liquid formulation comprising the pharmaceutical composition comprises about 66 grams of hemoglobin. In some embodiments, a unit of a liquid formulation comprising the pharmaceutical composition comprises about 67 grams of hemoglobin. In some embodiments, a unit of a liquid formulation comprising the pharmaceutical composition comprises about 68 grams of hemoglobin. In some embodiments, a unit of a liquid formulation comprising the pharmaceutical composition comprises about 69 grams of hemoglobin. In some embodiments, a unit of a liquid formulation comprising the pharmaceutical composition comprises about 70 grams of hemoglobin.

Generally, a pharmaceutical composition according to the various embodiments may comprise a dose of hemoglobin that is suspended within a solution and administered in units, where a unit is equal to 67.5 grams of hemoglobin. If a subject undergoes surgery or experiences blood loss, the pharmaceutical composition may be administered to the subject according to the following dosing regimen, where blood is replaced with units of liquid formulation. In some embodiments, the pharmaceutical composition comprises from about 30 g of hemoglobin/unit of solution administered to about 80 g of hemoglobin/unit of solution administered.

| Examples Of Blood Use | Average # Units Required per Patient |
|---|---|
| Automobile Accident | 50 units of blood |
| Heart Surgery | 6 units of blood |
|  | 6 units of platelets |
| Organ Transplant | 40 units of blood |
|  | 30 units of platelets |
|  | 20 bags of cryoprocipitate |
|  | 25 units of fresh frozen plasma |
| Bone Marrow Transplant | 120 units of platelets |
|  | 20 units of blood |

In some embodiments, the pharmaceutical composition comprises a dose from about 40 g of hemoglobin/unit of solution administered to about 80 g of hemoglobin/unit of solution administered. In some embodiments, the pharmaceutical composition comprises a dose from about 50 g of hemoglobin/unit of solution administered to about 80 g of hemoglobin/unit of solution administered. In some embodiments, the pharmaceutical composition comprises a dose from about 60 g of hemoglobin/unit of solution administered to about 80 g of hemoglobin/unit of solution administered. In some embodiments, the pharmaceutical composition comprises a dose from about 70 g of hemoglobin/unit of solution administered to about 80 g of hemoglobin/unit of solution administered. In some embodiments, the pharmaceutical composition comprises a dose from about 60 g of hemoglobin/unit of solution administered to about 70 g of hemoglobin/unit of solution administered.

The dose of the pharmaceutical composition of the various embodiments may also be measured in grams of polymersome administered per kg of a subject. In some embodiments, the total dose administered comprises from about 25 mg of polymer to about 35 mg of polymer per kg of a subject. In some embodiments, the total dose administered comprises from about 26 mg of polymer to about 35 mg of polymer per kg of a subject. In some embodiments, the total dose administered comprises from about 27 mg of polymer to about 35 mg of polymer per kg of a subject. In some embodiments, the total dose administered comprises from about 28 mg of polymer to about 35 mg of polymer per kg of a subject. In some embodiments, the total dose administered comprises from about 29 mg of polymer to about 35 mg of polymer per kg of a subject. In some embodiments, the total dose administered comprises from about 30 mg of polymer to about 35 mg of polymer per kg of a subject. In some embodiments, the total dose administered comprises from about 31 mg of polymer to about 35 mg of polymer per kg of a subject. In some embodiments, the total dose administered comprises from about 32 mg of polymer to about 35 mg of polymer per kg of a subject. In some embodiments, the total dose administered comprises from about 33 mg of polymer to about 35 mg of polymer per kg of a subject. In some embodiments, the total dose administered comprises from about 34 mg of polymer to about 35 mg of polymer per kg of a subject.

In some embodiments, the pharmaceutical composition is a liquid formulation that comprises an allosteric effector such as 2,3-Bisphosphoglycerate, wherein the formulation comprises from about 1 to about 100 mmol/L of formulation. In some embodiments, the formulation comprises from about 1 to about 100 mmol of a isomer of 2,3-Bisphosphoglycerate per L of formulation. In some embodiments, the formulation comprises from about 1 to about 10 mmol of a isomer of 2,3Bisphosphoglycerate per L of formulation. In some embodiments, the formulation comprises about 5 mmol of 2,3-Bisphosphoglycerate or isomer derived thereof per L of formulation. In some embodiments, the formulation comprises about 2.25 mmol of 2,3-Bisphosphoglycerate or isomer derived thereof per Unit (450 mL) of formulation.

The pharmaceutical compositions may be prepared, packaged, or sold in the form of a sterile, injectable, aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non toxic parenterally acceptable diluent or solvent, such as water or 1,3 butane diol, for example. Other acceptable diluents and solvents include, but are not limited to, Ringer's solution, isotonic sodium chloride solution, and fixed oils such as synthetic mono or di-glycerides. Other parentally-administrable formulations which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt. The formulations described herein, are also useful for pulmonary delivery and the treatment of such cancers of the respiratory system or lung, are also useful for intranasal delivery of a pharmaceutical composition of the various embodiments. Such formulation suitable for intranasal administration is a coarse powder comprising the active ingredient and having an average particle from about 0.2 to 500 micrometers, administered by rapid inhalation through the nasal passage from a container of the powder held close to the nares.

The various embodiment pharmaceutical compositions may be administered to deliver a dose of from about 0.1 g/kg/day to about 100 g/kg/day, where the gram measurement is equal to the total weight of hemoglobin and polymer in the pharmaceutical composition. In some embodiments, the dosage is from about 0.1 to 1 g/kg/day. In another embodiment, the dosage is from about 0.5 g/kg/day to about 1.0 g/kg/day. In another embodiment, the dosage is from about 1.0 g/kg/day to about 1.5 g/kg/day. In another embodiment, the dosage is from about 1.5 g/kg/day to about 2.0 g/kg/day. In another embodiment, the dosage is from about 2.5 g/kg/day to about 3.0 g/kg/day. In another embodiment, the dosage is 1.0, 2.0, 5.0, 10, 15, 20, 25, 30, 35, 40, 45, or 50 g/kg/day, where the gram measurement is equal to the total weight of hemoglobin and polymer in the pharmaceutical composition. In one embodiment, administration of a dose may result in a therapeutically effective concentration of the drug, protein, active agent, etc., between 1 μM and 10 μM in a diseased or cancer-affected tissue, or tumor of a mammal when analyzed in vivo.

In an embodiment, a pharmaceutical composition, especially one used for prophylactic purposes, can comprise, in addition, a pharmaceutically acceptable adjuvant filler or the like. Suitable pharmaceutically acceptable carriers are well known in the art. Examples of typical carriers include saline, buffered saline and other salts, lipids, and surfactants. The oxygen carrier or polymersome may also be lyophilized and administered in the forms of a powder. Taking appropriate precautions not to denature any protein component of the claimed invention, the preparations can be sterilized and if desired mixed with auxiliary agents, e.g., lubricants, preservatives, stabilizers, wetting agents, emulsifiers, salts for influencing osmotic pressure, buffers, and the like that do not deleteriously react with the oxygen carrier or polymersome of the claimed invention. They also can be combined where desired with other biologically active agents, e.g., antisense DNA or mRNA.

A pharmaceutical composition of the various embodiments may be prepared, packaged, or sold in bulk, as a single unit dose, or as a plurality of single unit doses. The amount of the active ingredient is generally equal to the dosage of the active ingredient which would be administered to a subject, or a convenient fraction of such a dosage, such as, for example, one-half or one-third of such a dosage, as would be known in the art.

The relative amounts of the active ingredient, the pharmaceutically acceptable carrier, and any additional ingredients in a pharmaceutical composition of the various embodiments may vary, depending upon the identity, size, and condition of the subject treated and further depending upon the route by which the composition is to be administered. By way of example, the composition may comprise from about 0.1% to about 100% (w/w) active ingredient.

The compositions and methods described herein can be useful for preventing or treating any blood disorder including but not necessarily limited to anemia, wherein a blood disorder causes low or poor oxygenation of tissues in a subject. In some embodiment the subject is need of a prevention or treatment for the blood disorder.

The compositions and methods described herein can be useful for preventing or treating cancers including leukemias, lymphomas, meningiomas, mixed tumors of salivary glands, adenomas, carcinomas, adenocarcinomas, sarcomas, dysgerminomas, retinoblastomas, Wilms' tumors, neuroblastomas, melanomas, and mesotheliomas; as represented by a number of types of cancers, including but not limited to breast cancer, sarcomas and other neoplasms, bladder cancer, colon cancer, lung cancer, pancreatic cancer, gastric cancer, cervical cancer, ovarian cancer, brain cancers, various leukemias and lymphomas. One would expect that any other human tumor cell, regardless of expression of functional p53, would be subject to treatment or prevention by the methods of the present invention, although the particular emphasis is on mammary cells and mammary tumors. The various embodiments may also encompass a method of treatment, according to which a therapeutically effective amount of the drug, protein, active agent, etc., or a vector comprising same according to the various embodiments may be administered to a patient requiring such treatment. The various embodiments should not be construed as being limited solely to these examples, as other cancer-associated diseases which are at present unknown, once known, may also be treatable using the methods of the various embodiments.

Also useful in conjunction with the methods provided in the various embodiments may be chemotherapy, phototherapy, anti-angiogenic or irradiation therapies, separately or combined, which maybe used before, contemporaneously, or after the enhanced treatments of the present invention, but will be most effectively used after the cells have been sensitized by the present methods. As used herein, the phrase "chemotherapeutic agent" means any chemical agent or drug used in chemotherapy treatment, which selectively affects tumor cells, including but not limited to, such agents as adriamycin, actinomycin D, camptothecin, colchicine, taxol, cis-platinum, vincristine, vinblastine, and methotrexate. Other such agents are well known in the art.

The compositions and methods described herein can be useful for preventing or treating anemia including but not necessarily limited to hemolytic anemia caused by viral infection such as Hepatitis C virus.

Methods of treating and/or ameloriating genetic blood disorders, such as thalassemia or sickle cell anemia, or delaying or ameliorating at least one symptom thereof, are contemplated herein, comprising administering to a patient in need thereof an effective amount of an oxygen carrier or polymersome of the claimed invention. All compositions disclosed herein are considered useful for incorporation into a pharmaceutical composition. In some embodiments, pharmaceutical composition of the claimed invention is used to treat or prevent an enlarged spleen and/or anemia. In some embodiments, pharmaceutical composition of the claimed invention is used to treat or prevent an enlarged spleen and/or anemia, excessive iron absorption, and those resulting from ineffective erythropoiesis due to excessive iron absorption, including osteoporosis, e.g. secondary osteoporosis.

In an embodiment, a method is provided to ameloriate or delay the onset of an enlarged spleen in a patient suffering from thalassemia, comprising administering a pharmaceutically effective amount of the oxygen carrier or polymersome of the claimed invention. For example, transfusion independent beta-thalassemia intermedia patients.

In some embodiments, the spleen size of a patient suffering from thalassemia and receiving a polymersome may be reduced by 10%, 20%, 30%, 40%, or even 50% or more as compared to a patient with a similar spleen size suffering from thalassemia and not being administered the oxygen carrier or polymersome of the claimed invention.

The various embodiments may include methods for treating, or amelioriating or delaying onset of at least one symptom of genetic blood disorders. Some embodiments methods may provide treatment or prevention of sickle cell disease, alpha-thalassemia, delta-thalassemia, and beta-thalassemia. Contemplated treatments herein include treatment of patients suffering from thalassemia minor, thalassemia intermedia, thalassemia major (Cooley's disease), e-β thalassemia, and sickle-β-thalassemia. Some embodiments methods may provide reducing the frequency of chelation therapy in a patient, e.g., suffering from thalessemia, that includes administering a disclosed compound is provided herein.

The various embodiments may include methods for stimulating wound healing in a subject in need thereof comprising administering the oxygen carrier or polymersome of the various embodiments to a subject in need thereof. Some embodiments may include methods for treating or preventing diseases, illnesses or conditions in mammals. In some embodiments, the compositions of the various embodiments may be used for canine anemia. In some embodiments, the compositions of the various embodiments may be useful to treat or prevent symptoms associated with iron deficiency. Some embodiments may provide methods for treating a blood disorder or low oxygenation of tissues in patients susceptible to, symptomatic of, or at elevated risk for developing hypertension.

The various embodiments may also include kits comprising any of the aforementioned compositions or pharmaceutical compositions comprising an oxygen carrier or a polymersome, wherein the oxygen carrier or a polymersome comprises at least one biocompatible polymer and at least one biodegradable polymer. According to some embodiments, the formulation may be supplied as part of a kit. The kit may comprise the pharmaceutical composition comprising an oxygen carrier or a polymersome. In another embodiment, the kit may comprise a lyophilized oxygen carrier or polymersome with an aqueous rehydration mixture. In another embodiment, the oxygen carrier or polymersome may be in one container while the rehydration mixture is in a second container. The rehydration mixture may be supplied in dry form, to which water may be added to form an rehydration solution prior to administration by mouth, venous puncture, injection, or any other mode of delivery. In some embodiments, the kit may further comprise a vehicle for administration of the composition such as tubing, a catheter, syringe, needle, and/or combination of any of the foregoing.

Any reference (patent, patent application, or journal article) disclosed in this application is herein incorporated by reference. The various embodiments may be illustrated, but are not limited to, the following examples:

Example I

Methods and Materials to Construct Biodegradable PEH Dispersions with Varying Physicochemical Properties Poly(ethyleneoxide)-block-poly(ε-caprolactone) (PEO-b-PCL) possessing a PEO block size of ~1.5-4 kDa and with a PEO block fraction of ~10-15% by weight may be utilized to form biodegradable PEH dispersions. Poly(ethyleneoxide)-block-poly(γ-methyl ε-caprolactone) (PEO-b-PMCL) copolymers of varying molecular weight, hydrophobic-to-hydrophilic block fraction, and resulting polymersome membrane-core thickness may be further incorporated to generate PEH constructs that are not only slowly biodegradable but also uniquely deformable, enabling passage through compromised capillary beds, via infra. PMCL, as a derivative of PCL, is a similarly fully bioresorbable polymer that degrades via non-enzymatic cleavage of its ester linkages. Polymersomes composed from PEO-b-PMCL are spontaneously formed at lower temperatures, in greater yields, and possess more deformable and viscoelastic membranes as compared to those composed from PEO-b-PCL. They also similarly degrade much more slowly than vesicles formed from PEO-b-PGA, PEO-b-PLA, or PEO-b-PLGA. As such, PEO-b-PCL and PEO-b-PMCL-derived PEH dispersions (e.g. PEO(2 kilo-Daltons)-b-PCL(12 kiloDaltons) and PEO(2 kiloDaltons)-b-PMCL(9.4 kiloDaltons)) demonstrate larger hemoglobin-encapsulation efficiencies, smaller average particle diameters, and lower levels of metHb generation as compared to biodegradable cellular HBOCs claimed in the literature.

Synthesis of PEH Dispersions:

To synthesize PEH dispersions, bovine and human hemoglobin may be used as starting materials. Well-established hemoglobin extraction and purification procedures may be utilized to harvest hemoglobin with >97% purity and of <3% metHb level. Briefly, bovine erythrocytes may be extracted, centrifuged and collected in 3.8% sodium citrate by Animal Technologies, Inc. (Tyler, Tex., USA). Packed bovine erythrocytes may be centrifuged at 6000 rpm for 20 minutes (2-3° C.), and the supernatant removed. The cell pellet may be washed with three volumes of ice-cold isotonic saline solution (0.95 gNaCl per 100 mL) to one volume of sedimented erythrocytes, which may be followed by gentle mixing and swirling for 2-3 minutes. The mixture may be centrifuged again at 6000 rpm for 19-20 minutes (2-3° C.) and the supernatant discarded. The washing step may be repeated twice. Erythrocytes may be lyzed by adding two volumes of hypotonic, 15 mOsm phosphate buffer (PB) at pH 7.4 to one volume of washed erythrocytes, followed by gentle mixing and swirling for 2-3 minutes. The mixture may be left to stand for one hour in an ice bath. Lyzed erythrocytes may then be filtered through a 0.05 μm Minikros Sampler hollow fiber cartridge (Spectrum Laboratories, Inc., Rancho Dominguez, Calif., USA) at 4° C. The retained fluid may be recycled and the filtrate (hemoglobin solution) collected. The extracted hemoglobin solution may then be filtered through a 50 kDa hollow fiber cartridge (Spectrum Laboratories, Inc.) at 4° C. to concentrate the hemoglobin solution. The concentrated hemoglobin solution may be diluted with phosphate buffer (PB) or phosphate buffered saline (PBS) at physiological pH of 7.3 to the desired hemoglobin concentration.

PEO(2k)-b-PCL(12k), and at least four different PEO-b-PMCL copolymers with PEO molecular weight ranging from about 1.1 kiloDaltons to about 3.5 kiloDaltons and PMCL molecular weight ranging from about 4.5 kiloDaltons-12 kiloDaltons, have previously been shown to give a stable and high yield of polymersomes. By varying the initial amounts of polymer (from 1 mg-10 mg per sample), as well as the initial aqueous hemoglobin concentrations used in polymersome formation (from 50 mg/ml to 300 mg/ml), PEH dispersions that differ in the degree of hemoglobin encapsulation may be generated.

PEH dispersions may be formed by using two well-established methodologies: 1) "thin-film rehydration" which involves the generation of giant (micron-sized) polymersomes by immersion of a dry thin-film of polymer in an aqueous solution of dissolved Hb (at 40° C. for 48 hours) followed by serial extrusion through membranes of progressively decreasing pore diameters to generate uniform PEH dispersions of nanometric dimensions (e.g. 100 nm); and, 2) "sonication rehydration" which is based on immersion of the same dry thin-film of polymer in an aqueous hemoglobin solution followed by high-frequency sonication at ambient temperature followed by extrusion through a single pore-size membrane to yield the desired nanometric PEH dispersion. Each of these methods produces a high yield of stable polymersomes that may be effectively controlled through membrane extrusion to yield unilamellar, mono-dispersed suspensions of PEHs that vary from 100 nm-1 μm diameter in average size. Although thin-film rehydration yields a very narrow PEH size distribution, and higher Hb encapsulation % due to larger core volumes available for encapsulation, the stability of hemoglobin and the resultant PEO-b-PCL-based PEH dispersions has been demonstrably less. This result may be due to the fact that the hydration temperature for PEO-b-PCL is close to the denaturation temperature of free hemoglobin.[54] PEO-b-PMCL polymersomes may be formed by thin-film or sonication rehydration at room temperature and expectedly enable a higher yield of cellular HBOCs with greater Hb encapsulation efficiency. Variants of each described PEH formulation may be produced by co-encapsulating N-acetyl-L-cysteine (NAC) in order to suppress hemoglobin oxidation during PEH synthesis. NAC helps limit metHb generation during PEH formation. Unencapsulated hemoglobin may be separated from PEH dispersions using dialysis, ultrafiltration and/or, and/or size exclusion chromatography.

Example II

Characterization of Physicochemical Properties of PEH Dispersions

To verify PEH generation, each Hb/polymer formulation may be characterized for particle size distribution using dynamic light scattering (DLS). The PEH structure and morphology may be directly visualized in their native physiological environments using cryogenic transmission electron microscopy (cryo-TEM). The viscosities of the various PEO-b-PCL and PEO-b-PMCL-based PEH dispersions may be measured using a microviscometer. Hb encapsulation %, defined as the weight ratio of hemoglobin in the resultant PEH suspension compared to that in the initial solution, is a significant parameter that determines the ultimate utility of that particular PEH formulation as a potential synthetic oxygen carrier.

Multiple PEO-b-PCL and PEO-b-PMCL-based PEH dispersions may be systematically generated, varying in initial polymer composition, polymer-to-Hb weight ratios, particle sizes and production strategies. Subsequent measurements of the Hb encapsulation % may be conducted in order to determine the best formulation construct for future in vivo application. To measure Hb encapsulation %, two independent methods may be used. In the first method, PEH dispersions may be initially lysed with a detergent (e.g. triton X-100) and the UV absorbance of the resulting lysate may be measured in order to determine the mass of Hb and subsequent Hb encapsulation % of the original PEH composition. While this calculation method is relatively straight forward, it may overestimate the encapsulation % through some assumptions on total Hb dispersion volume. As such, an asymmetric flow field-flow fractionator coupled with a differential interferometric refractometer may be used to measure the concentration of eluting, unencapsulated Hb from which the encapsulation % may be determined. From these measurements, the weight ratio of Hb:polymer in the various PEH dispersions may be further calculated. The percentage of metHb in each of the PEH dispersions may be determined by analogous methodology to the well-established cyanometMb assay.

Example III

Characterization of the Oxygen-Carrying Properties of Biodegradable PEH Dispersions The oxygen binding properties of PEO-b-PCL and PEO-b-PMCL-based PEH dispersions may be measured using established techniques. The equilibrium oxygen binding properties are thoroughly characterized as well as the diffusion kinetics of oxygen across polymersome membranes. With the aid of these measurements, oxygen permeabilities and oxygen-membrane diffusion coefficients for these various PEH dispersions may be determined. These very fundamental parameters have, hitherto, been uncharacterized for any synthetic oxygen carrier but are critical for the optimal design of a successful cellular HBOC. Nitric oxide (NO) binding profiles of various PEO-b-PCL and PEO-bPMCL-based PEH dispersions may be further studied.

A physiologically important function of the red blood cell membrane is its management of the transport of endogenous gaseous messenger-molecules such as NO. As described above, acellular HBOCs are observed to induce vasoconstriction, hypertension, reduced blood flow, and vascular damage in animals due to their entrapment of endothelium-derived NO. Hb encapsulated in liposomes, however, is not been observed to be similarly "vasoactive"; analogous to those of natural red blood cells, liposome membranes effectively retard NO binding through effective Hb sequestration from the surrounding vascular environment. PEH dispersions may likely exhibit more resistance to NO scavenging owing to their thicker membranes and lower permeabilities. Finally, different measurements on PEO-b-PCL and PEO-b-PMCL-based PEH dispersions may be performed in order to test their stability and integrity under physiological conditions for extended durations of time.

Experimental:

Characterization of Oxygen Binding Properties:

Equilibrium oxygen binding properties such as P50 and n of PEO-b-PCL and PEO-b-PMCL-based PEH dispersions may be measured using a Hemox-analyzer[51, 52]. Dependence of these properties on the composition of PEH dispersions may depend on different Hb-loading sources (animal vs. human), a series of Hb-loading concentrations, as well as an allosteric effector (such as inositol hexaphosphate) in the aqueous phase of the polymersomes.

In addition to these equilibrium measurements, the kinetics of oxygen diffusion across PEH membranes and binding to/release of Hb for different PEO-b-PCL and PEO-b-PMCL-based PEH dispersions may also be determined using a highly sensitive oxygen microelectrode. Measurements of various PEHs may be compared to those from free Hb and empty polymersome dispersions (without Hb) in order to delineate the roles of diffusion and binding in O2 take-up. A diffusion-reaction transport model may be used to determine oxygen permeability of different polymersome membranes. A correlation between diffusive properties of various diblock copolymer membranes and measured oxygen binding properties of PEH formulations may be used.

Characterization of NO Binding Properties:

NO binding of PEO-b-PCL and PEO-b-PMCL-based PEH dispersions under oxygenated and deoxygenated conditions may be systematically studied using stopped flow spectroscopy. The time-course of binding may be measured by taking rapid absorbance scans of the various oxygenated or deoxygenated PEH dispersions rapidly mixed with NO-containing solution. A range of Hb loading concentrations, PEH dispersion concentrations, and PEH sizes may be used. Similarly, the roles of NO diffusion and binding in NO uptake by PEO-b-PCL and PEO-b-PMCL-based PEH constructs may be further characterized by conducting experiments comparing PEH, free Hb, and empty polymersomes using a NO microelectrode. The NO binding rate constants for PEO-b-PCL and PEO-b-PMCL-based PEH dispersions under different conditions may be established and compared with the results for free Hb solution, liposome encapsulated Hb (LEH), and Oxyglobin®.

Characterization of the Stability and Integrity of PEH Dispersions:

To test the stability of various PEO-b-PCL and PEO-b-PMCL-based PEH dispersions, they may be stored in saline solution and in blood plasma at 4° C. and at 37° C. for several days; changes in PEH morphology and size distribution may be assessed using cryo-TEM and DLS, respectively. Similarly, changes in Hb concentration, metHb level, and Hb leakage over time may be tested using techniques described herein. The effects of physiological shear rates on the stability and integrity of PEH dispersions may be determined by passing them through a parallel-plate flow chamber apparatus, as described in S. Usami, et al, Ann. Biomed. Eng., 21, 77-83 (1993); and D. K. Brunk, D. A. Hammer, Biophys J. 72: 2820-2833 (1997); which are incorporated herein by reference. The outlet PEH dispersions may be characterized using cryo-TEM and DLS.

Measurement of Critical Lysis Tension, Critical Areal Strain Using Micropipette Aspiration:

Micropipet aspiration of hemoglobin-encapsulating polymersomes follows analogous procedures to those described above and in the previous references. Briefly, micropipets made of borosilicate glass tubing (Friedrich and Dimmock, Milville, N.J.) may be prepared using a needle/pipette puller (model 730, David Kopf Instruments, Tujunga, Calif.) and microforged using a glass bead to give the tip a smooth and flat edge. The inner diameters of the micropipets may range from 1 um to 6 um and may be measured using computer imaging software. The pipettes may then used to pick up the hemoglobin-loaded and unloaded polymersomes and apply tension to their membranes. Micropipets may be filled with PBS solution and connected to an aspiration station mounted on the side of a Zeiss inverted microscope, equipped with a manometer, Validyne pressure transducer (models DP 15-32 and DP 103-14, Validyne Engineering Corp., Northridge, Calif.), digital pressure read-outs, micromanipulators (model WR-6, Narishige, Tokyo, Japan), and MellesGriot millimanipulators (course x,y,z control). Suction pressure may be applied via a syringe connected to the manometer. PBS solutions that have osmolalities of 310-320 mOsm may be used in order to make the polymersomes flaccid (internal vesicle solution is typically 290-300 mOsm sucrose). The osmolalities of the solutions may be measured using an osmometer. Since sucrose and PBS have different densities and refractive indices, the polymersomes may settle in solution and may be readily visible under phasecontrast or DIC optics.

Example IV

Development of PEO-b-PCL and PEO-b-PMCL-based PEH Dispersions that are Capable of Dry Storage, Point-of-Care Rehydration, and In Vivo Delivery Polymer Synthesis:

Acrylate-modified PEO-b-PCL (PEO-b-PCL-acryl) may be synthesized according to standard procedures using stannous octoate as the catalyst. The resulting polymer may be found to have a number average molecular weight of 14 kDa (12 and 2 kDa for the PCL and PEO blocks, respectively), which can be determined by calibrating the NMR peaks to the terminal methoxy group on the PEO at approximately 3.4 ppm. The polydispersity of the polymer is <1.5. Acrylation of the OH terminus of the PCL block does not lead to a significant change in the polymer size or distribution following the second purification. The acrylation efficiency is found to be 99%.

Formation of PEH Dispersions:

To synthesize PEO-b-PCL-acryl-based PEH dispersions, bovine and human Hb may be used as starting materials. Well-established Hb extraction and purification procedures may be utilized to harvest Hb with >97% purity and of <3% metHb level. PEO(2k)-b-PCL(12k)-acryl polymer and 2,2-dimethoxy-2-phenylacetophenone (DMPA) may be dried on roughened Teflon via dissolution in methylene chloride at a molar ratio of 1:1, deposition on Teflon, and evaporation of the organic solvent. Varying the amount of PEO(2k)-b-PCL (12k)-acryl polymer (from 1 mg-10 mg per sample), as well as the initial aqueous Hb concentrations used in polymersome formation (from 50 mg/ml to 300 mg/ml), PEH dispersions that compartmentalize DMPA in their membranes and that differ in the degree of aqueous Hb encapsulation are generated. PEH dispersions may be formed by using two well-established methodologies: 1) "thin-film rehydration" which involves the generation of giant (micron-sized) polymersomes by immersion of a dry thin-film of polymer in an aqueous solution of dissolved Hb (at 60° C. for 48 hours) followed by serial extrusion through membranes of progressively decreasing pore diameters to generate uniform PEH dispersions of nanometric dimensions (e.g. 100 nm); and, 2) "sonication rehydration" which is based on immersion of the same dry thin-film of polymer in an aqueous Hb solution followed by high-frequency sonication at ambient temperature followed by extrusion through a single pore-size membrane to yield the desired nanometric PEH dispersion. Each of these methods produces a high yield of stable polymersomes that can be effectively controlled through membrane extrusion to yield unilamellar, mono-dispersed suspensions of PEHs that vary from 100 nm-1 µm diameter in average size. In some embodiments, a variant of each described PEH formulation is produced by co-encapsulating N-acetyl-L-cysteine (NAC) in order to suppress Hb oxidation during PEH synthesis. NAC helps limit metHb generation during PEH formation. Unencapsulated Hb may be separated from PEH dispersions using dialysis, ultrafiltration and/or size exclusion chromatography.

Stabilization of PEH Membranes After Formation:

Once assembled into PEO-PMC-acryl-based PEH dispersions, UV light exposure induces a radical polymerization of the acryl groups via activation of the photoinitator DMPA incorporated in the polymersome membranes. This approach does not hinder hydrolysis of the PCL chain and yields oligocaprolactone units, PEG, and kinetic chains of poly(acrylic acid) as the degradation products. Hemoglobin is protected from photo-induced degradation of metHb formation by co-ecapsulation of NAC within Hb in the polymersomes's aqueous phase. Polymerization of the vescicles' membranes proceeds by exposure of the DMPA-incorporated PEO-b-PCL-acryl PEH dispersions to UV light using an OmniCure Series 1000 spot-curing lamp with a collimating lens (Exfo, Ontario, Canada; 365 nm, 55 mW/cm2) for 10-30 min.

Lyophilization and Dry-Phase Storage:

Lyophilization proceeds by free-drying the PEO-b-PCL acryl PEH dispersions after UV light exposure by placement in liquid nitrogen until bubbling ceases. The frozen PEH dispersions may then placed on a benchtop lyophilizer (FreeZone 4.5 L Benchtop Freeze Dry System, Labconco, Kansas City, Mo.; Model 77500) for 24 h until samples are dry. The dry, collapsed PEH dispersions are then stored in a dessicator under argon gas and placed at 4° C.

Point-of-Care Hydration:

The dried PEH dispersions are taken out of the dessicator and placed in a vial. The same original volume of aqueous solution may added back to the samples to hydrate the vesicles. Polymersome rehydration may be further augmented by gentle vortexing for 10 minutes to achieve full vesicle resuspension, intact polymersomes are verified by DLS, which shows minimal vesicle aggregation and no destruction into micelles. Hemoglobin retention may verified by running the PEH dispersion over an aqueous size-exclusion column and taking aliquots of the running bands for UV-vis analysis. Bands corresponding to polymersomes, as verified further by DLS of the elution aliquots, contain hemoglobin as assessed by UV-vis spectroscopy. The stability of the retained hemoglobin may be further verified by the UV-vis spectra that show no bands corresponding to metMb generation or any further hemoglobin breakdown products.

Development of Molecularly-Targeted PEO-b-PCL and PEO-b-PMCL-Based PEH Dispersions:

Through well-established chemical conjugation methods, polymersome surfaces may be modified with various biological ligands to impart specific multi-avidity biological adhesion. Similar methodology may be adopted to generate molecularly- and cellular-targeted polymersome-encapsulated PEH dispersions that are able to promote, amongst other things, wound healing and improved efficacy of radiation therapy to hypoxia tissues. Biological ligands may be conjugated to these nanoparticles via a carbodiimide-mediated aqueous phase reaction. The degree of polymersome-surface coverage with ligand may be systematically varied (from 1% to >10% of the total surface area of the polymersomes) by using ligands of different concentrations and PEH dispersions that are synthesized from mixtures containing different ratios of functionalized to unfunctionalized polymers. After verifying peptide conjugation to polymersome surfaces, the kinetic binding of the resultant PEH formulations to recombinant molecular targets/receptors may be characterized via surface plasmon resonance (Biacore SPR) measurements. Dose-dependent curves may analyzed in a manner similar to that described for the free biological ligand. These processes reveal kinetic parameters of the interaction between PEH dispersions and molecular targets (on-rate, kon and off-rate, koff) and the change in affinity of ligands (dissociation constant, K) as affected by their conjugation to polymersomes.

Experimental:

Established chemical modification procedures may be used to functionalize the PEO terminus of PEO-b-PCL diblock copolymers with carboxyl groups and verify the reactions by 1H NMR spectroscopy. PEH dispersions may be created and purified from various combinations of functionalized and unfunctionalized copolymers using standard separation methods to yield mono-dispersed suspensions of unilamellar vesicles that are stable for several months. PEH size distributions may be determined by dynamic light scattering (DLS). Ligand identity and purity may be confirmed by reverse phase high performance liquid chromatography and MALDI mass spectrometry. Ligand conjugation to carboxyl-terminated PEO groups on the polymersome surface may be carried in an aqueous reaction mediated by 1-ethyl-3-(3-dimethylaminopropyl)carbodiimide (EDC) and Nhydroxysuccinimide (NHS). The extent of ligand conjugation may be determined using a micro-BCA assay. The resultant targeted PEH dispersions may be extensively imaged by cryogenic transmission electron microscopy (cryo-TEM) to verify their stability after ligand conjugation. Their size distributions may again be measured by DLS. The degree of ligand conjugation may be verified using flow cytometry. SPR measurements may be carried out on biosensor instruments Biacore X and Biacore 2000 (Biacore AG, Uppsala, Sweden) at 25° C. Recombinant purified Her2/neu receptors composed of the ectodomain of Her2/neu fused to the Fc of human IgG (which may be purchased from Xcyte Therapeutics (Seattle, Wash.)) and immobilized by attachment to the dextran hydrogel on the sensor surface. Targeted PEH constructs may be injected in various concentrations and their binding may be monitored in real time. The kinetic rate constants (kon and koff) and the equilibrium binding constant (KD) for receptor/PEH binding may be estimated from kinetic analysis of the sensorgrams. PEHs without targeting ligands or irrelevant ligand-conjugated PEHs may be used as controls.

Alternative ligand conjugation chemistries can also be employed. For example, organic phase reactions where the diblock polymer may be chemically functionalized and conjugated with select ligands (small molecules, peptides that have organic-phase solubility) prior to forming PEH dispersions are possible. This organic coupling method ensures that the PEO terminus is conjugated with ligand before it is exposed to aqueous solution where it might lose many of its modified surface reactive groups via competing hydrolysis. Also, as an alternative method to vary the degree of ligand surface conjugation, PEH dispersions composed of PEO-b-PCL copolymers may be created that vary with respect to PEO and PCL block sizes. This approach may control the kinetics of ligand conjugation to polymersome surfaces as well as the degree of ligand surface coverage for a given PEH formulation. It is possible that targeted PEH formulations may bind to the sensor surface in a non-specific manner during SPR measurements, thereby affecting its regeneration and signal-to-background ratio. If a reliable measurement cannot be performed, ligand-conjugated PEH binding characteristics may be studied using ELISA or isothermal titration calorimetry, which are other established techniques for studying nanoparticle binding.

The foregoing method descriptions and the process flow diagrams are provided merely as illustrative examples and are not intended to require or imply that the steps of the various embodiments must be performed in the order presented. As will be appreciated by one of skill in the art the order of steps in the foregoing embodiments may be performed in any order. Words such as "thereafter," "then," "next," etc. are not intended to limit the order of the steps; these words are simply used to guide the reader through the description of the methods. Further, any reference to claim elements in the singular, for example, using the articles "a," "an" or "the" is not to be construed as limiting the element to the singular.

Skilled artisans may implement the above-described methods, processes and/or functionality in varying ways for each particular application, but such implementation decisions should not be interpreted as causing a departure from the scope of the present invention.

The preceding description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the following claims and the principles and novel features disclosed herein.

What is claimed:

1. An oxygen carrier composition comprising:
  a polymersome comprising a plurality of cross-linked block copolymer chains, wherein each block copolymer chain comprises:
    at least one hydrophilic polymer block;
    at least one hydrophobic polymer block; and
    at least one polymerizable group conjugated to the at least one hydrophobic polymer block or hydrophilic polymer block;
  an initiator molecule, wherein the initiator molecule activates a polymerization reaction between the polymerizable groups and the polymer blocks of different copolymer chains to create cross links; and
  an oxygen-binding compound containing a heme group.

2. The composition of claim 1, wherein the oxygen-binding compound is within the polymersome.

3. The composition of claim 1, wherein the oxygen-binding compound is a naturally occurring protein, a recombinant protein, a recombinant polypeptide, a synthetic polypeptide, a chemical synthesized by an animal, a synthetic small molecule, a carbohydrate, a nucleic acid, a lipid or a polymer.

4. The composition of claim 1, wherein the oxygen-binding compound is a compound derived from one or more of a naturally occurring protein, a recombinant protein, a recombinant polypeptide, a synthetic polypeptide, a chemical synthesized by an animal, a synthetic small molecule, a carbohydrate, a nucleic acid, a lipid and a polymer.

5. The composition of claim 1, wherein the oxygen-binding compound is hemoglobin.

6. The composition of claim 1, wherein the oxygen-binding compound is a derivative of hemoglobin.

7. The composition of claim 1, wherein at least one polymer block in each of the plurality of block copolymer chains is a biodegradable polymer and at least one polymer block of each of the plurality of block copolymer chains is a biocompatible polymer.

8. The composition of claim 7, wherein at least one hydrophilic polymer block in each of the plurality of block copolymer chains is poly(ethylene oxide) or poly(ethylene glycol).

9. The composition of claim 8, wherein at least one hydrophobic polymer block in each of the plurality of block copolymer chains is poly($\epsilon$-caprolactone), and wherein the at least one polymerizable group is attached to a poly($\epsilon$-caprolactone) terminus.

10. The composition of claim 8, further comprising one of a poly(peptide), a poly(saccharide) or a poly(nucleic acid).

11. The composition of claim 8, wherein each block copolymer chain comprises a biodegradable diblock copolymer of poly(ethylene oxide) and poly($\epsilon$-caprolactone).

12. The composition of claim 11, wherein the poly(ethylene oxide) has a number-average molecular weight from about 1.5 kiloDalton to about 4.0 kiloDalton.

13. The composition of claim 11, wherein a weight fraction of the poly(ethylene oxide) is from about 11 to about 20 percent of the total weight of the block copolymer.

14. The composition of claim 11, wherein the poly(ethylene oxide) has a number-average molecular weight from about 1.5 to about 3.8 kiloDalton and a weight fraction from about 10 to about 30 percent of the total weight of the block copolymer.

15. The composition of claim 1, wherein at least one hydrophilic polymer block in each of the plurality of block copolymer chains is poly(ethylene oxide) or poly(ethylene glycol) having a weight fraction from about 30 to about 50 percent of the total weight of the block copolymer chain.

16. The composition of claim 1, wherein at least one hydrophobic polymer block in each of the plurality of block copolymer chains is poly($\epsilon$-caprolactone) having a weight fraction from about 50 to about 70 percent of the total weight of the block copolymer chain.

17. The composition of claim 1, wherein at least one hydrophobic polymer block in each of the plurality of block copolymer chains comprises poly($\epsilon$-caprolactone) with a number-average molecular weight from about 9 kiloDalton to about 23 kiloDalton.

18. The composition of claim 1, wherein the number-average molecular weight is from about 9.5 kiloDalton to about 22.2 kiloDalton.

19. The composition of claim 1, wherein:
the at least one hydrophilic polymer block of each of the plurality of block copolymer chains comprises poly(ethylene oxide) having a number-average molecular weight of about 2 kiloDalton; and
the at least one hydrophobic polymer block of each of the plurality of block copolymer chains comprises poly($\epsilon$-caprolactone) having a number-average molecular weight of about 12 kiloDalton.

20. The composition of claim 19, wherein the poly(ethylene oxide) has a number average molecular weight that is from about 1.8 kiloDalton to about 1.9 kiloDalton and the poly($\epsilon$-caprolactone) has a number average molecular weight that is from about 8 kiloDalton to about 9.5 kiloDalton.

21. The composition of claim 2, wherein the polymersome has an aqueous interior.

22. The composition of claim 2, wherein the polymersome has a hydrophobic polymersome membrane.

23. The composition of claim 2, wherein the polymersome has a hydrophilic surface.

24. The composition of claim 1, wherein the polymersome has a diameter from about 50 nm to about 5 $\mu$m.

25. The composition of claim 1, wherein the polymersome has a membrane thickness from about 5 nm to about 30 nm.

26. The composition of claim 1, wherein the polymersome is biodegradable.

27. The composition of claim 7, wherein each block copolymer chain further comprises at least one additional hydrophilic polymer chosen from poly(ethylene oxide), poly(acrylic acid), poly(ethylene glycol), or any combination thereof.

28. The composition of claim 7, wherein the at least one hydrophobic polymer block further comprises at least one additional hydrophobic polymer chosen from poly(caprolactone), poly(methylcaprolactone), poly(menthide), poly(lactide), poly(glycolide), poly(methylglycolide), poly(dimethylsiloxane), poly(isobutylene), poly(styrene), poly(ethylene), poly(propylene oxide), or any combination thereof.

29. A kit, comprising:
(i) a pharmaceutical composition comprising an oxygen carrier, wherein the oxygen carrier comprises:
a plurality of cross-linked block copolymer chains, wherein each block copolymer chain comprises:
at least one hydrophilic polymer block;
at least one hydrophobic polymer block; and
at least one polymerizable group conjugated to the at least one hydrophobic polymer block or hydrophilic polymer block;
an initiator molecule, wherein the initiator molecule activates a polymerization reaction between the polymerizable groups and the polymer blocks of different copolymer chains to create cross links; and
an oxygen-binding compound containing a heme group; and
(ii) an implement for administering the oxygen carrier intravenously, via inhalation, topically, per rectum, per the vagina, transdermally, subcutaneously, intraperitoneally, intrathecally, intramuscularly, or orally.

30. A kit comprising a first container and a second container, wherein the first container comprises an oxygen carrier and wherein the second container comprises a rehydration mixture, wherein the oxygen carrier is lyophilized or dried, and comprises:
a plurality of cross-linked block copolymer chains, wherein each block copolymer chain comprises:
at least one hydrophilic polymer block;
at least one hydrophobic polymer block; and
at least one polymerizable group conjugated to the at least one hydrophobic polymer block or hydrophilic polymer block;

an initiator molecule, wherein the initiator molecule activates a polymerization reaction between the polymerizable groups and the polymer blocks of different copolymer chains to create cross links; and an oxygen-binding compound containing a heme group.

* * * * *